US006258559B1

(12) United States Patent
Zamost

(10) Patent No.: US 6,258,559 B1
(45) Date of Patent: Jul. 10, 2001

(54) METHOD FOR PRODUCING PROTEINS IN TRANSFORMED PICHIA

(75) Inventor: Bruce L. Zamost, Seattle, WA (US)

(73) Assignee: ZymoGenetics, Inc., Seattle, WA (US)

( * ) Notice: Subject to any disclaimer, the term of this patent is extended or adjusted under 35 U.S.C. 154(b) by 0 days.

(21) Appl. No.: 09/532,803

(22) Filed: Mar. 21, 2000

Related U.S. Application Data

(60) Provisional application No. 60/125,540, filed on Mar. 22, 1999.

(51) Int. Cl.$^7$ .................................................. C12P 21/06
(52) U.S. Cl. ............................................................ 435/69.1
(58) Field of Search ................................... 435/69.1, 71.1

(56) References Cited

U.S. PATENT DOCUMENTS

| | | | |
|---|---|---|---|
| 5,002,876 | * 3/1991 | Sreekrishna et al. | 435/69.5 |
| 5,716,808 | 2/1998 | Raymond | 435/69.1 |
| 5,736,383 | 4/1998 | Raymond | 435/255.7 |
| 5,783,183 | * 7/1998 | Langeveld et al. | 424/94.1 |
| 5,783,423 | * 7/1998 | Wood et al. | 435/69.6 |
| 5,854,039 | 12/1998 | Raymond | 435/490 |
| 5,888,768 | 3/1999 | Raymond | 435/69.1 |
| 6,001,597 | 12/1999 | Raymond et al. | 435/69.1 |

FOREIGN PATENT DOCUMENTS

| | | |
|---|---|---|
| 0 510 693 | 10/1992 | (EP) . |
| WO90/03431 | 4/1990 | (WO) . |
| WO95/21928 | 8/1995 | (WO) . |
| WO98/02565 | 1/1998 | (WO) . |

OTHER PUBLICATIONS

Stoll et al., in Deutscher, ed.,Guide to Protein Purification, Methods in Enzymology, vol. 182, 1990, pp. 29–32.*
Sherman, in Guthrie et al., eds, Guide to Yeast Genetics and Molecular Biology, Methods in Enzymology, vol. 194, 1991, p. 14.*
Camelbeeck et al. (1992, in IFAC Symp. Ser., Modeling and Control of Biotechnical Processes, pp. 199–202).*
International Search Report for application No. PCT/US00/07618.
Zamost et al., Production of recombinant leptin using a new yeast expression system: *Pichia methanolica* Abstract No. 075, 217$^{th}$ National Meeting of the American Chemical Society, Mar. 21–25, 1999.
Romanos, M., "Advances in the use of *Pichia pastoris* for high–level gene expression," *Curr. Opin. Biotechnol.* 6:527–533 (1995).
Hollenberg, C.P. and Gellissen, G., "Production of Recombinant Proteins by methylotrophic yeasts," *Curr. Opin. Biotechnol.* 8:554–560 (1997).
Raymond, C.K., Bukowski, T., Holderman, S.D., Ching, A.F.T., Vanaja, E., and Stamm, M.R., "Development of Methylotrophic Yeast *Pichia methanolica* for the Expression . . . ," *Yeast* 14:11–23 (1998).
Stratton, J., Chiruvolu, V., and Meagher, M., "High Cell–Density Fermentation," in *Pichia Protocols*, Higgins, D.R. and Cregg, J.M. (Eds.), pp. 107–120 (Humana Press, Inc. 1998).
Cregg, J.M.,"Expression in the Methylotrophic Yeast *Pichia pastoris,"* in *Gene Expression Systems: Using Nature for the Art of Expression,* Fernandez and Hoeffler (Eds.), pp. 157–191 (Academic Press, Inc. 1999).
Raymond, C.K., Pownder, T.A., and Sexson, S.L., "General Method for Plasmid Construction Using Homologous Recombination," *BioTechniques* 26(1):134–141 (Jan. 1999).

* cited by examiner

*Primary Examiner*—James Ketter
*Assistant Examiner*—Lisa Gansheroff
(74) *Attorney, Agent, or Firm*—Phillip B.C. Jones

(57) ABSTRACT

Methylotrophic yeasts are useful hosts for the production of commercially valuable recombinant proteins. However, the development of large-scale cultures of recombinant methylotrophic yeasts has been hindered by the formation of precipitation in culture media. A new soluble minimal medium overcomes this problem. Moreover, new feeding schemes provide cultures of high biomass, which produce biologically active recombinant protein.

41 Claims, 8 Drawing Sheets

METHOD FOR PRODUCING PROTEINS IN TRANSFORMED PICHIA

CROSS-REFERENCE TO RELATED APPLICATIONS

This application claims the benefit of U.S. Provisional application No. 60/125,540 (filed Mar. 22, 1999), the contents of which are incorporated by reference.

TECHNICAL FIELD

The present invention relates generally to methods for producing heterologous proteins in transformed cells. In particular, the present invention provides improved methods for culturing transformed methylotrophic yeast cells that express heterologous proteins.

BACKGROUND OF THE INVENTION

Certain yeasts are able to utilize methanol as a sole source of carbon and energy. Species of the so-called methylotrophic yeasts that have the biochemical pathways necessary for methanol utilization are classified into four genera, based upon cell morphology and growth characteristics: Hansenula, Pichia, Candida, and Torulopsis (Billon-Grand, Mycotaxon 35:201 (1989); Kurtzman, Mycologia 84:72 (1992)). Not all species within these genera are capable of utilizing methanol as a source of carbon and energy, and therefore, individual species of a genus may differ in physiology and metabolism.

Methylotrophic yeasts are attractive candidates for use in recombinant protein production systems. Some methylotrophic yeasts have been shown to grow rapidly to high biomass on minimal defined media. Certain genes of methylotrophic yeasts are tightly regulated and highly expressed under induced or de-repressed conditions, suggesting that promoters of these genes might be useful for producing polypeptides of commercial value. See, for example, Romanos et al., Yeast 8:423 (1992), Cregg et al., Bio/Technology 11:905 (1993), Faber et al., Yeast 11:1331 (1995), and Jong et al., SIM News 46:199 (1996).

Development of methylotrophic yeasts as hosts for use in recombinant production systems has been slow, due in part to a lack of efficient promoters, selectable markers, and mutant host cells, as well as suitable transformation techniques. The most highly developed methylotrophic host systems utilize Pichia pastoris (Komagataella pastoris) and Hansenula polymorpha (Pichia angusta) (Faber et al, Curr. Genet. 25:305–310 (1994); Cregg et al., ibid.; Romanos et al., Yeast 8:423 (1992); U.S. Pat. No. 4,855,242; U.S. Pat. No. 4,857,467; U.S. Pat. No. 4,879,231; and U.S. Pat. No. 4,929,555).

For example, numerous fermentation processes have been described for expression of heterologous proteins by Pichia pastorsis. Typically, these methods are based on a fermentation recipe developed by Brieley et al., international publication No. WO 90/03431, which uses an initial growth phase on glycerol, followed by a period of glycerol feeding to build up the biomass (see, for example, Stratton et al., "High Cell-Density Fermentation," in Methods in Molecular Biology, Vol. 103, Higgins and Cregg (eds.), pages 107–120 (Humana Press Inc. 1998)). To induce protein expression using the methanol-inducible alcohol oxidase 1 (AOX1) promoter, a slow feed of methanol is initiated along with glycerol feeding. After the cells have adapted to growth on methanol, the glycerol feed is stopped, and methanol is used as the sole carbon source for the remainder of the fermentation. The basal recipe includes a very high level of inorganic salts, including magnesium sulfate, potassium sulfate, calcium sulfate, phosphoric acid, and trace metals. The combination of these salts forms an insoluble precipitate that easily falls out of solution.

A new methylotrophic yeast species, designated Pichia methanolica, has recently been developed for a heterologous expression system (Raymond et al., Yeast 14:11 (1998)). The use of the expensive carbon source glycerol for Pichia methanolica is not practical due to the yeast's poor growth on this substrate. Moreover, the high level of inorganic salts, which precipitate from the medium developed for Pichia pastoris, indicated that a new fermentation recipe would be beneficial for growth and protein expression by Pichia methanolica.

Raymond et al., Yeast 14:11 (1998), described a new recipe for P. methanolica that uses a filtered sterilized solution of phosphate glass (sodium hexametaphosphate) for a phosphate source. The benefits of using phosphate glass were described for E. coli fermentation where it does not form precipitates with other inorganic salts and glucose (see, for example, (Giusez et al., Protein Express. Purif 12:249 (1998)). One of the main drawbacks in using phosphate glass is that this component must be added separately as a filter-sterilized solution to the fermentor, and the basal medium may form a precipitate before addition of the phosphate glass. The other major drawback is that phosphate glass can inhibit the growth of P. methanolica.

Accordingly, there remains a need in the art for techniques that will facilitate the large-scale culture of methylotrophic yeasts, including Pichia methanolica, to produce polypeptides of economic importance.

BRIEF SUMMARY OF TIE INVENTION

The present invention provides improved methods for producing a peptide or polypeptide by a recombinant methylotrophic yeast host.

DETAILED DESCRIPTION OF THE INVENTION

1. Overview

Figure 1:
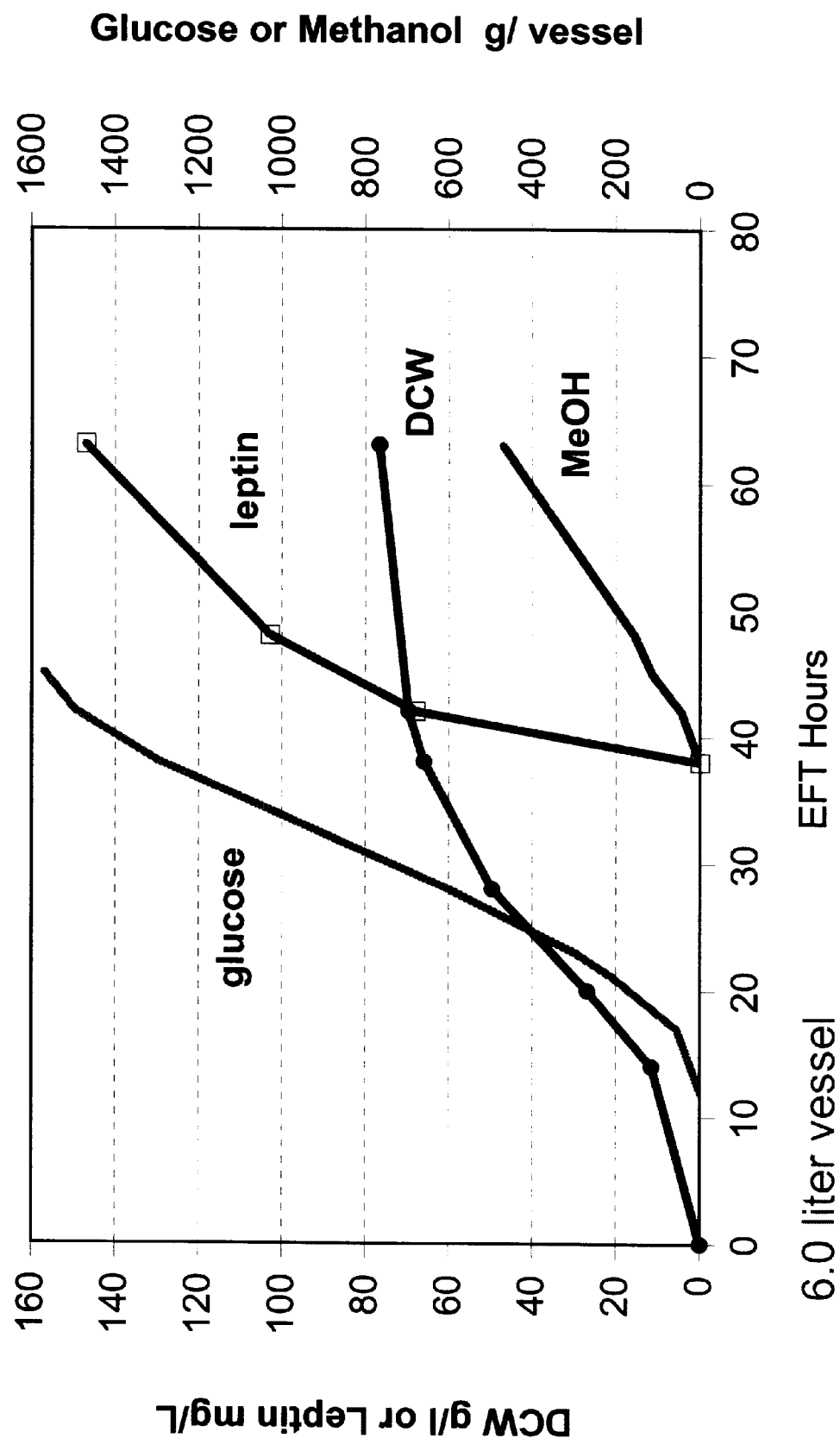
FIG. 1 shows a time course of leptin production by Pichia methanolica in a fed batch fermentation without co-feeding of alcohol and glucose. "DCW" refers to dry cell weight, while "EFT" refers to elapsed fermentation time.

To overcome the fermentation medium problems described above, a new balanced recipe was developed that was soluble after autoclaving. An exemplary new recipe contains ammonium sulfate, potassium phosphate, magnesium sulfate, citric acid, glucose, and trace metals. This recipe was found to support growth of *P. methanolica* in fed batch fermentations up to 125 grams/liter dry cell weight. Along with this new recipe, two feeding schemes were developed. One scheme utilizes a glucose feed batch followed by alcohol feeding, while the second scheme is a mixed-carbon feeding system designed for optimal growth and protein expression. The new system utilizes an initial batch growth phase on glucose followed by glucose feeding to build up cell mass. Once a high level of biomass is obtained, an alcohol feed is started for induction of a methanol-inducible promoter. At this point, the glucose feed rate is adjusted and co-fed along with the alcohol, or the glucose feed can be turned off with feeding proceeding with alcohol alone.

Previous studies have shown co-feeding glucose and methanol in chemostat cultures of the methylotrophic yeast *Hansenula polymorpha* to be a problem at high feed rates. Glucose has also been shown to repress the methanol-inducible AOX promoter in *Pichia pinus* fermentations treated with methanol. Yet the new feeding profiles described herein for *P. methanolica* show co-utilization of alcohol and glucose and no repression by glucose during methanol induction.

Surprisingly, a third variation of a feeding scheme that lacks alcohol addition provides for the production of a heterologous protein under the control of a methanol-inducible promoter. Additional new feeding schemes are described herein.

For example, the present invention provides methods for producing a peptide or polypeptide by a recombinant Pichia host, comprising the steps of:

(a) incubating, in a soluble minimal medium, a recombinant Pichia host to produce a Pichia culture, wherein the cultured Pichia expresses the peptide or polypeptide under the control of a methanol-inducible promoter, wherein the soluble minimal medium consists essentially of water, glucose, inorganic ammonia, potassium, phosphate, iron, biotin, and citric acid, and wherein the incubation period is sufficient to increase the density of viable Pichia in the Pichia culture, (b) feeding the cultured Pichia a limiting amount of glucose for a period of time sufficient to derepress the methanolic pathway of the Pichia, and (c) supplementing the medium of the cultured Pichia with an alcohol feed, wherein the alcohol feed stimulates the production of the peptide or polypeptide by the cultured Pichia cells, and wherein the cultured Pichia cells receive the alcohol feed either with a limiting amount of glucose or in the absence of a glucose feed.

The present invention also provides methods that further comprise the step of (d) isolating peptide or polypeptide from the medium or from the cultured yeast cells. The isolation step can be performed following an incubation of 72 to 96 hours elapsed fermentation time.

In variations of these methods, the minimal medium does not contain sodium hexametaphosphate. Moreover, the minimal medium can be prepared with deionized water and the minimal medium does not contain calcium sulfate. Suitable minimal medium does not contain polypeptides or peptides.

According to these methods, the alcohol can be selected from the group consisting of methanol, ethanol, propanol, isopropanol, butanol, and isobutanol. The alcohol feed can maintain the medium alcohol level at a concentration that is less than 1 gram/liter, such as a concentration of 0.05 gram/liter. Moreover, the alcohol feed can be initiated when the cultured Pichia reach a density of 30 to 80 grams of dry cell weight per liter.

These methods can be performed with Pichia, including *Pichia pastoris* and *Pichia methanolica*. Suitable *Pichia methanolica* can have a defect in expression of a functional methanol utilization gene, such as the AUG1 gene or the AUG2 gene. Moreover, suitable *Pichia methanolica* can have a defect in the expression of AUG1 and AUG2 gene products. In addition, suitable *Pichia methanolica* can have a functional deficiency in at least one vacuolar protease. The functional deficiency can be the result of a genetic defect, wherein the defect is an insertion, deletion, or substitution of one or more base pairs in a parent gene that encodes proteinase A or proteinase B. Alternatively, the *Pichia methanolica* can have a genetic defect in the parent gene encoding proteinase A and in the parent gene encoding proteinase B. An exemplary parent proteinase A gene comprises the nucleotide sequence of SEQ ID NO:4, while an exemplary parent proteinase B gene comprises the nucleotide sequence of SEQ ID NO:5.

According to the methods described herein, the recombinant Pichia host can comprise an expression vector that comprises a nucleic acid molecule encoding the peptide or polypeptide of interest, the methanol-inducible promoter, and a transcription terminator, wherein the promoter is operably linked with the nucleic acid molecule, and wherein the nucleic acid molecule is operably linked with the transcription terminator. Illustrative methanol inducible promoters include a *Pichia pastoris* alcohol oxidase 1 (AOX1) promoter, a *Candida boidinii* alcohol oxidase promoter, a *Pichia methanolica* alcohol utilization gene 1 (AUG1) promoter, a *Pichia methanolica* alcohol utilization gene 2 (AUG2) promoter, a *Pichia methanolica* dihydroxyacetone synthase gene promoter, a *Pichia methanolica* formate dehydrogenase gene promoter, and a *Pichia methanolica* catalase gene promoter. An illustrative *Pichia methanolica* AUG1 promoter comprises nucleotides 24–1354 of SEQ ID NO:2, and an illustrative *Pichia methanolica* AUG2 promoter comprises nucleotides 91–169 of SEQ ID NO:3.

Such expression vectors can further comprise a selectable marker gene that complements a mutation in *Pichia methanolica*, wherein the selectable marker gene is a *Pichia methanolica* gene, such as a *Pichia methanolica* ADE2 gene. An illustrative ADE2 gene comprises nucleotides 407–2851 of SEQ ID NO: 1.

Exemplary polypeptides encoded by such expression vectors include heterologous polypeptides such as an antibody, an antibody fragment, Factor VIIa, proinsulin, insulin, follicle stimulating hormone, tissue type plasminogen activator, tumor necrosis factor, interleukin, granulocyte-colony stimulating factor, granulocyte macrophage-colony stimulating factor, interferon, leptin, stem cell growth factor, erythropoietin, and thrombopoietin. Illustrative interleukins include interleukin-1, interleukin-2, interleukin-3, interleukin-4, interleukin-5, interleukin-6, interleukin-7, interleukin-8, interleukin-9, interleukin-10, interleukin-11, interleukin-12, interleukin-13, interleukin-14, interleukin-15, interleukin-16, interleukin-17, and interleukin-18. Exemplary interferons include interferon-α, interferon-β, interferon-γ, interferon-ω, interferon-δ, interferon-τ, and interferon-ε. Other heterologous proteins include antibody fusion proteins, chimeric antibodies, humanized antibodies, and anti-idiotype antibodies.

In a variation of the above methods, the present invention contemplates methods for producing a peptide or polypeptide in transformed Pichia, comprising the steps of:

(a) incubating, in a soluble minimal medium, transformed Pichia to produce a Pichia culture, wherein the cultured Pichia express the peptide or polypeptide under the control of a methanol-inducible promoter, wherein the soluble minimal medium consists essentially of water, glucose as a carbon source, inorganic ammonia, potassium, phosphate, iron, biotin, and citric acid, (b) initiating a glucose feed at 8 to 12 hours elapsed fermentation time, wherein the glucose feed is sufficient to increase the density of viable Pichia in the culture, and (c) initiating an alcohol feed at about 36 hours to about 48 hours elapsed fermentation time, wherein the alcohol of the alcohol feed is selected from the group consisting of methanol, ethanol, propanol, isopropanol, butanol, and isobutanol, and wherein the alcohol feed stimulates the production of the peptide or polypeptide by the cultured Pichia.

In another variation of the above methods, the present invention provides methods for producing a peptide or polypeptide in transformed Pichia, comprising the steps of:

(a) incubating, in a soluble minimal medium, transformed Pichia that express the peptide or polypeptide under the control of a methanol-inducible promoter to produce a Pichia culture, wherein the minimal medium is a soluble medium consisting essentially of water, glucose as a carbon source, inorganic ammonia, potassium, phosphate, iron, biotin, and citric acid, (b) initiating a glucose feed at 8 to 12 hours elapsed fermentation time, wherein the glucose feed is sufficient to increase the density of viable Pichia in the culture, (c) initiating an alcohol feed at about 36 hours to about 48 hours elapsed fermentation time, wherein the alcohol of the alcohol feed is selected from the group consisting of methanol, ethanol, propanol, isopropanol, butanol, and isobutanol, and wherein the alcohol feed stimulates the production of the peptide or polypeptide by the cultured Pichia, and (d) stopping the glucose feed at about 66 hours to about 96 hours elapsed fermentation time.

In yet another variation, the present invention provides methods for producing a peptide or polypeptide by a recombinant methylotrophic yeast host, comprising the step of incubating the recombinant methylotrophic yeast host to produce a yeast culture, wherein the cultured recombinant yeast cells express the peptide or polypeptide under the control of an alcohol-inducible promoter (e.g., a methanol-inducible promoter), wherein the medium is formulated to comprise sugar but not alcohol, and wherein the incubated yeast cells produce the peptide or polypeptide. Suitable methylotrophic yeast hosts include Pichia recombinant host cells, such as *Pichia methanolica* host cells. Illustrative sugars include glucose, mannose, fructose, and the like. Suitable media include the soluble minimal medium described below, or a rich medium. Media can initially contain the sugar in an amount ranging from about 0.5% to about 6%, about 1% to about 5%, and about 2% to about 4%. For example, media can initially contain sugar in the amount of about 0.5%, about 1%, about 2%, about 3%, about 4%, about 5%, or about 6%. To derepress the promoter, the sugar concentration is subsequently maintained at less than 0.5%, usually less than 0.1%, and often at levels undetectable by enzymatic or colorimetric assays known in the art. Appropriate fermentation methods include batch fermentation, fed-batch fermentation, and continuous fermentation, wherein sugar is supplied at levels sufficient to maintain the viability of the culture but in limiting amounts as disclosed above. These methods can also be performed when the expression of a peptide or polypeptide of interest is controlled by a constitutive promoter.

The present invention also includes methods for producing a peptide or polypeptide by a recombinant methylotrophic yeast host, comprising the step of incubating the recombinant methylotrophic yeast host in a medium to produce a yeast culture, wherein the cultured yeast cells express the peptide or polypeptide under the control of an alcohol-inducible promoter, wherein the medium is formulated to comprise alcohol as the sole carbon source for the yeast, and wherein the incubated yeast produce the peptide or polypeptide. Suitable methylotrophic yeast hosts include Pichia recombinant host cells, such as *Pichia methanolica* host cells. Illustrative alcohols include methanol, ethanol, propanol, isopropanol, butanol, isobutanol, and the like. Suitable media include the soluble minimal medium described below. Media can contain the alcohol in an amount ranging from about 0.1% to about 3%, about 0.5% to about 3%, about 1% to about 3%, and about 1% to about 2%. For example, medium can contain alcohol in the amount of about 0.5%, about 1%, about 2%, or about 3%. Appropriate fermentation methods include batch fermentation, fed-batch fermentation, and continuous fermentation. These methods can also be performed when the expression of a peptide or polypeptide of interest is controlled by a constitutive promoter.

The present invention also contemplates methods of producing leptin, comprising the steps of: obtaining a culture of recombinant methylotrophic yeast cells that comprise a leptin expression vector, culturing the yeast cells in a culture medium, wherein the yeast cells synthesize biologically active leptin, and optionally, isolating the biologically active leptin from the cultured yeast cells or from the culture medium. Leptin can also be produced by methods comprising the steps of (a) culturing transformed Pichia cells that comprise a leptin expression vector and that synthesize leptin, and (b) isolating biologically active leptin from the cultured Pichia cells or from the culture medium. The biologically active leptin can also be isolated from the medium of the cultured Pichia cells. An illustrative leptin is human leptin.

The present invention also provides leptin expression vectors, comprising a nucleic acid molecule encoding leptin, a methanol-inducible promoter, and a transcription terminator, wherein the promoter is operably linked with the nucleic acid molecule, and wherein the nucleic acid molecule is operably linked with the transcription terminator. Suitable methanol inducible promoters include a *Pichia pastoris* alcohol oxidase 1 (AOX1) promoter, a *Candida boidinii* alcohol oxidase promoter, a *Pichia methanolica* alcohol utilization gene 1 (AUG1) promoter, a *Pichia*

*methanolica* alcohol utilization gene 2 (AUG2) promoter, a *Pichia methanolica* dihydroxyacetone synthase gene promoter, a *Pichia methanolica* formate dehydrogenase gene promoter, and a *Pichia methanolica* catalase gene promoter. An illustrative *Pichia methanolica* AUG1 promoter comprises nucleotides 24–1354 of SEQ ID NO:2, and an illustrative *Pichia methanolica* AUG2 promoter comprises nucleotides 91–169 of SEQ ID NO:3. Such leptin expression vectors can further comprise a selectable marker gene that complements a mutation in *Pichia methanolica*, wherein the selectable marker gene is a *Pichia methanolica* gene, such as a *Pichia methanolica* ADE2 gene. An illustrative ADE2 gene comprises nucleotides 407–2851 of SEQ ID NO: 1. An exemplary leptin is human leptin.

The present invention further contemplates a recombinant methylotrophic yeast cell, wherein the cell comprises such expression vectors. A suitable yeast cell is a *Pichia methanolica* yeast cell. Such *Pichia methanolica* can have a functional deficiency in at least one vacuolar protease. The functional deficiency can be the result of a genetic defect, wherein the defect is an insertion, deletion, or substitution of one or more base pairs in a parent gene that encodes proteinase A or proteinase B. Alternatively, the *Pichia methanolica* can have a genetic defect in the parent gene encoding proteinase A and in the parent gene encoding proteinase B. An exemplary parent proteinase A gene comprises the nucleotide sequence of SEQ ID NO:4, while an exemplary parent proteinase B gene comprises the nucleotide sequence of SEQ ID NO:5.

These and other aspects of the invention will become evident upon reference to the following detailed description and attached drawings. In addition, various references are identified below and are incorporated by reference in their entirety.

2. Definitions

In the description that follows, a number of terms are used extensively.

The following definitions are provided to facilitate understanding of the invention.

As used herein, "nucleic acid" or "nucleic acid molecule" refers to polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., α-enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be finctionalized as ethers or esters.

Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid molecule" also includes so-called "peptide nucleic acids," which comprise naturally-occurring or modified nucleic acid bases attached to a polyamide backbone. Nucleic acids can be either single stranded or double stranded.

The term "structural gene" refers to a nucleic acid molecule that is transcribed into messenger RNA (mRNA), which is then translated into a sequence of amino acids characteristic of a specific polypeptide.

An "isolated nucleic acid molecule" is a nucleic acid molecule that is not integrated in the genomic DNA of an organism. For example, a DNA molecule that encodes a growth factor that has been separated from the genomic DNA of a cell is an isolated DNA molecule. Another example of an isolated nucleic acid molecule is a chemically-synthesized nucleic acid molecule that is not integrated in the genome of an organism. A nucleic acid molecule that has been isolated from a chromosome of a particular species is smaller than the complete DNA molecule of that chromosome.

A "nucleic acid molecule construct" is a nucleic acid molecule, either single- or double-stranded, that has been modified through human intervention to contain segments of nucleic acid combined and juxtaposed in an arrangement not existing in nature.

"Linear DNA" denotes non-circular DNA molecules having free 5' and 3' ends. Linear DNA can be prepared from closed circular DNA molecules, such as plasmids, by enzymatic digestion or physical disruption.

"Complementary DNA (cDNA)" is a single-stranded DNA molecule that is formed from an MRNA template by the enzyme reverse transcriptase. Typically, a primer complementary to portions of MRNA is employed for the initiation of reverse transcription. Those skilled in the art also use the term "CDNA" to refer to a double-stranded DNA molecule consisting of such a single-stranded DNA molecule and its complementary DNA strand. The term "CDNA" also refers to a clone of a cDNA molecule synthesized from an RNA template.

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes. Sequences within promoters that function in the initiation of transcription are often characterized by consensus nucleotide sequences. These promoter elements include RNA polymerase binding sites, TATA sequences, and transcription factor binding sites. As an illustration, a suitable promoter may contain Gcr1p binding sites, characterized by the consensus sequences CTTCC or GGAAG, and Rap1p binding sites (see, in general, Watson et al. (eds.), *Molecular Biology of the Gene*, 4th Edition, (The Benjamin/Cummings Publishing Company, Inc., 1987). If a promoter is an inducible promoter, then the rate of transcription increases in response to an inducing agent. In contrast, the rate of transcription is not regulated by an inducing agent if the promoter is a constitutive promoter. Repressible promoters are also known.

A "core promoter" contains essential nucleotide sequences for promoter function, including the TATA box and start of transcription. By this definition, a core promoter may or may not have detectable activity in the absence of specific sequences that may enhance activity.

A "regulatory element" is a nucleotide sequence that modulates the activity of a core promoter. For example, a regulatory element may contain a nucleotide sequence that binds with cellular factors enabling transcription exclusively or preferentially in particular cells, tissues, or organelles. These types of regulatory elements are normally associated with genes that are expressed in a "cell-specific," "tissue-specific," or "organelle-specific" manner.

"Heterologous DNA" refers to a DNA molecule, or a population of DNA molecules, that does not exist naturally within a given host cell. DNA molecules heterologous to a particular host cell may contain DNA derived from the host cell species (i.e., endogenous DNA) as long as that host DNA is combined with non-host DNA (ie., exogenous DNA). For example, a DNA molecule containing a non-host DNA segment encoding a polypeptide operably linked to a host DNA segment comprising a transcription promoter is considered to be a heterologous DNA molecule. Conversely, a heterologous DNA molecule can comprise an endogenous gene operably linked with an exogenous promoter. As another illustration, a DNA molecule comprising a gene derived from a wild-type cell is considered to be heterologous DNA if that DNA molecule is introduced into a mutant cell that lacks the wild-type gene.

A peptide or polypeptide encoded by a non-host DNA molecule is a "heterologous" peptide or polypeptide.

The term "secretory signal sequence" refers to a nucleotide sequence that encodes a peptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

An "integrated genetic element" is a segment of DNA that has been incorporated into a chromosome of a host cell after that element is introduced into the cell through human manipulation. Within the present invention, integrated genetic elements are most commonly derived from linearized plasmids that are introduced into the cells by electroporation or other techniques. Integrated genetic elements are passed from the original host cell to its progeny.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

A "cloning vector" is a nucleic acid molecule, such as a plasmid, cosmid, or bacteriophage, that has the capability of replicating autonomously in a host cell. Cloning vectors typically contain one or a small number of restriction endonuclease recognition sites that allow insertion of a nucleic acid molecule in a determinable fashion without loss of an essential biological function of the vector, as well as nucleotide sequences encoding a marker gene that is suitable for use in the identification and selection of cells transformed with the cloning vector. Marker genes typically include genes that provide tetracycline resistance or ampicillin resistance.

An "expression vector" is a nucleic acid molecule encoding a gene that is expressed in a host cell. Typically, an expression vector comprises a transcription promoter, a gene, and a transcription terminator. Gene expression is usually placed under the control of a promoter, and such a gene is said to be "operably linked to" the promoter. Similarly, a regulatory element and a core promoter are operably linked if the regulatory element modulates the activity of the core promoter.

A "recombinant host" is a cell that contains a heterologous nucleic acid molecule, such as a cloning vector or expression vector.

"Integrative transformants" are recombinant host cells, in which heterologous DNA has become integrated into the genomic DNA of the cells.

A "fusion protein" is a hybrid protein expressed by a nucleic acid molecule comprising nucleotide sequences of at least two genes. For example, a fusion protein can comprise at least part of a protein of interest fused with a polypeptide that binds an affinity matrix. Such a fusion protein provides a means to isolate large quantities of the protein of interest using affinity chromatography.

An "isolated polypeptide" is a polypeptide that is essentially free from contaminating cellular components, such as carbohydrate, lipid, or other proteinaceous impurities associated with the polypeptide in nature. Typically, a preparation of isolated polypeptide contains the polypeptide in a highly purified form, i.e., at least about 80% pure, at least about 90% pure, at least about 95% pure, greater than 95% pure, or greater than 99% pure. One way to show that a particular protein preparation contains an isolated polypeptide is by the appearance of a single band following sodium dodecyl sulfate (SDS)-polyacrylamide gel electrophoresis of the protein preparation and Coomassie Brilliant Blue staining of the gel. However, the term "isolated" does not exclude the presence of the same polypeptide in alternative physical forms, such as dimers or alternatively glycosylated or derivatized forms.

The term "expression" refers to the biosynthesis of a gene product. For example, in the case of a structural gene, expression involves transcription of the structural gene into mRNA and the translation of MRNA into one or more polypeptides.

An "anti-idiotype antibody" is an antibody that binds with the variable region domain of an immunoglobulin. As a result, an anti-idiotype antibody can mimic the epitope that binds with the variable region of the immunoglobulin.

An "antibody fragment" is a portion of an antibody such as F(ab')$_2$, F(ab)$_2$, Fab', Fab, and the like. Regardless of structure, an antibody fragment binds with the same antigen that is recognized by the intact antibody. The term "antibody fragment" also includes any synthetic or genetically engineered protein that acts like an antibody by binding to a specific antigen to form a complex. For example, antibody fragments include isolated fragments consisting of the light chain variable region, "Fv" fragments consisting of the variable regions of the heavy and light chains, recombinant single chain polypeptide molecules in which light and heavy variable regions are connected by a peptide linker ("sFv proteins"), and minimal recognition units consisting of the amino acid residues that mimic the hypervariable region.

A "chimeric antibody" is a recombinant protein that contains the variable domains and complementary determining regions derived from a rodent antibody, while the remainder of the antibody molecule is derived from a human antibody.

"Humanized antibodies" are recombinant proteins in which murine complementarity determining regions of a monoclonal antibody have been transferred from heavy and light variable chains of the murine immunoglobulin into a human variable domain.

As used herein, the term "immunomodulator" includes cytokines, stem cell growth factors, lymphotoxins, co-stimulatory molecules, hematopoietic factors, and synthetic analogs of these molecules. Examples of immunomodulators include tumor necrosis factor, interleukins (e.g., interleukin-1 (IL-1), IL-2, IL-3, IL4, IL-5, IL-6, IL-7, IL-8, IL-9, IL-10, IL-11, IL-12, IL-13, IL-14, IL-15, IL-16, IL-17, and IL-18), colony stimulating factors (e.g., granulocyte-colony stimulating factor (G-CSF) and granulocyte macrophage-colony stimulating factor (GM-CSF)), interferons (e.g., interferons-$\alpha$, $\beta$, -$\gamma$, -$\omega$, -$\tau$, and -$\epsilon$), the stem cell growth factor designated "S1 factor," erythropoietin, and thrombopoietin.

The term "antibody fusion protein" refers to a recombinant molecule that comprises an antibody, or antibody fragment, and a therapeutic agent. Examples of therapeutic agents suitable for such fusion proteins include immunomodulators ("antibody-immunomodulator fusion protein") and toxins ("antibody-toxin fusion protein"). Illustrative toxin components include a Pseudomonas exotoxin moiety, a diphtheria toxin moiety, an RNase moiety, a DNase I moiety, a gelonin moiety, and a Staphylococcal enterotoxin-A moiety.

"Early log phase growth" is that phase of cellular growth in culture when the cell concentration is from $2 \times 10^6$ cells/ml to $8 \times 10^6$ cells/ml.

A "repressing carbon source" is a metabolizable, carbon-containing compound that, when not limited, suppresses the expression in an organism of genes required for the catabolism of other carbon sources. By "limited" is meant that the carbon source is unavailable or becomes available at such a rate that it is immediately consumed and therefore the prevailing concentration of that carbon source in an organism's environment is effectively zero. Repressing carbon sources that can be used within the present invention include hexoses and ethanol. Glucose is particularly preferred.

"Rich" culture media are those culture media that are based on complex sources of nutrients, typically cell or tissue extracts or protein hydrolysates. Rich media will vary in composition from batch to batch due to variations in the composition of the nutrient sources.

"YEPD" medium contains 2% D-glucose, 2% BACTO Peptone (Difco Laboratories, Detroit, MI), 1% BACTO yeast extract (Difco), 0.004% adenine, and 0.006% L-leucine.

The term "200× tryptophan, threonine solution" refers to a solution of 3.0% L-threonine, 0.8% L-tryptophan in water.

"ADE D" medium contains 0.056%-Ade-Trp-Thr powder, 0.67% yeast nitrogen base without amino acids, 2% D-glucose, and 0.5% 200× tryptophan, threonine solution.

"ADE DS" medium contains 0.056%-Ade-Trp-Thr powder, 0.67% yeast nitrogen base without amino acids, 2% D-glucose, 0.5% 200× tryptophan, threonine solution, and 18.22% D-sorbitol "LEU D" medium contains 0.052%-Leu-Trp-Thr powder, 0.67% yeast nitrogen base without amino acids, 2% D-glucose, and 0.5% 200× tryptophan, threonine solution. "HIS D" medium contains 0.052%-His-Trp-Thr powder, 0.67% yeast nitrogen base without amino acids, 2% D-glucose, and 0.5% 200× tryptophan, threonine solution. "URA D" medium contains 0.056%-Ura-Trp-Thr powder, 0.67% yeast nitrogen base without amino acids, 2% D-glucose, and 0.5% 200× tryptophan, threonine solution.

"URA DS" medium contains 0.056%-Ura-Trp-Thr powder, 0.67% yeast nitrogen base without amino acids, 2% D-glucose, 0.5% 200× tryptophan, threonine solution, and 18.22% D-sorbitol.

"-Leu-Trp-Thr powder" is made by combining 4.0 grams adenine, 3.0 grams arginine, 5.0 grams aspartic acid, 2.0 grams histidine, 6.0 grams isoleucine, 4.0 grams lysine, 2.0 grams methionine, 6.0 grams phenylalanine, 5.0 grams serine, 5.0 grams tyrosine, 4.0 grams uracil, and 6.0 grams valine (all L-amino acids).

"-His-Trp-Thr powder" is made by combining 4.0 grams adenine, 3.0 grams arginine, 5.0 grams aspartic acid, 6.0 grams isoleucine, 8.0 grams leucine, 4.0 grams lysine, 2.0 grams methionine, 6.0 grams phenylalanine, 5.0 grams serine, 5.0 grams tyrosine, 4.0 grams uracil, and 6.0 grams valine (all L-amino acids).

"-Ura-Trp-Thr powder" is made by combining 4.0 grams adenine, 3.0 grams arginine, 5.0 grams aspartic acid, 2.0 grams histidine, 6.0 grams isoleucine, 8.0 grams leucine, 4.0 grams lysine, 2.0 grams methionine, 6.0 grams phenylalanine, 5.0 grams serine, 5.0 grams tyrosine, and 6.0 grams valine (all L-amino acids).

"-Ade-Trp-Thr powder" is made by combining 3.0 grams arginine, 5.0 grams aspartic acid, 2.0 grams histidine, 6.0 grams isoleucine, 8.0 grams leucine, 4.0 grams lysine, 2.0 g methionine, 6.0 g phenylalanine, 5.0 grams serine, 5.0 grams tyrosine, 4.0 grams uracil, and 6.0 grams valine (all L-amino acids).

A "functionally deficient mutated gene" is a mutated gene which, as a result of a mutation, encodes for the expression of less than 10% of the activity of the expression product of its wild-type counterpart. For example, the functionally deficient gene can encode for less than 1% of the activity of its wild-type counterpart, or less than 0.01% as determined by appropriate assays. In certain embodiments, the activity can be essentially undetectable (ie., not significantly above background). Functionally deficient genes can be generated by mutations in either coding or non-coding regions.

"Vacuolar proteases" are defined by their function as those proteases that directly or indirectly provide the proteolytic activity present in the vacuole of a cell. The term is applied to proteases that are present in the vacuole, as well as to proteases that, through their proteolytic activity, cause the activation of proteases present in the vacuole.

The phrase "batch method" of fermentation refers to a type of fermentation that is performed with a closed system, in which the composition of the medium is determined at the beginning of the fermentation and is not subject to artificial alterations during the fermentation. That is, medium is inoculated with one or more yeast cells at the start of fermentation, and fermentation is allowed to proceed. Often, a batch fermentation is "batch" with respect to the addition of carbon source, and attempts are made during fermentation to control factors such as pH and oxygen concentration. In batch systems, the metabolite and biomass compositions of the system change constantly up to the time the fermentation is stopped. Within batch cultures, yeast cells pass through a static lag phase to a high growth log phase, and, finally, to a stationary phase, in which the growth rate is diminished or stopped. If untreated, yeast cells in the stationary phase will eventually die. In a batch method, yeast cells in log phase generally are responsible for the bulk of synthesis of end product.

A "fed-batch" method of fermentation is similar to typical batch method, except that the substrate is added in increments as the fermentation progresses. Fed-batch fermentation is useful when catabolite repression may inhibit yeast cell metabolism, and when it is desirable to have limited amounts of substrate in the medium. Typically, the measurement of the substrate concentration in a fed-batch system is estimated on the basis of the changes of measurable factors reflecting metabolism, such as pH, dissolved oxygen, the partial pressure of waste gases (e.g., $CO_2$), and the like.

The term "continuous" method of fermentation refers to fermentation with an open system, in which a fermentation medium is added continuously to a bioreactor, and an approximately equal amount of conditioned medium is removed simultaneously for processing. Continuous fermentation generally maintains the cultures at a high density, in which yeast cells are primarily in log phase growth. Typically, continuous fermentation methods are performed to maintain steady state growth conditions, and yeast cell loss, due to medium withdrawal, should be balanced against the cell growth rate in the fermentation.

General methods for performing batch, fed-batch, and continuous methods of fermentation are well known to those of skill in the art. See, for example, Brock, T. D., *Biotechnology: A Textbook of Industrial Microbiology, 2$^{nd}$ Edition* (Sinauer Associates, Inc. 1989), Demain, A. L. and Davies, J. E. (1999). *Manual of Industrial Microbiology and Biotechnology, 2$^{nd}$ Edition* (ASM Press 1999), and Hewitt et al., *J. Biotechnol.* 75:251(1999).

3. Transformation of Pichia

The methods detailed herein highlight the use of *Pichia methanolica* as a model methylotrophic yeast. Methods for transforming other species of Pichia, such as *Pichia pastoris*, are known to those in the art (see, for example, Faber et al., *Yeast* 11:1331 (1995), Sudbery, *Curr. Opin. Biotech.* 7:517 (1996), Hollenberg and Gellissen, *Curr. Opin. Biotech.* 8:554 (1997), Higgens and Cregg (eds.), *Pichia Protocols,* pages 249–261 (Humana Press, Inc. 1998), Cregg, "Expression in the Methylotrophic Yeast *Pichia pastoris*," in *Gene Expression Systems: Using Nature for the Art of Expression*, Fernandez and Hoeffler (eds.), pages 157–191 (Academic Press, Inc. 1999)).

(a) Methods for Selecting Pichia Transformants

Strains of *Pichia methanolica* are available from the American Type Culture Collection (Manassas, Va., USA) and other repositories. Cells to be transformed with heterologous DNA may have a mutation that can be complemented by a gene (a "selectable marker") on the heterologous DNA molecule. This selectable marker allows the transformed cells to grow under conditions in which untransformed cells cannot multiply ("selective conditions"). The general principles of selection are well known in the art. Commonly used selectable markers are genes that encode enzymes required for the synthesis of amino acids or nucleotides. Auxotrophic mutants having mutations in these genes cannot grow in media lacking the specific amino acid or nucleotide unless the mutation is complemented by the selectable marker. Use of such selective culture media ensures the stable maintenance of the heterologous DNA within the host cell.

A suitable selectable marker of this type for use in *Pichia methanolica* is a *P. methanolica* ADE2 gene, which encodes phosphoribosyl-5-aminoimidazole carboxylase (AIRC; EC 4.1.1.21). The ADE2 gene, when transformed into an ade2 host cell, allows the cell to grow in the absence of adenine. The coding strand of a representative *P. methanolica* ADE2 gene sequence is disclosed as SEQ ID NO:1 by Raymond, U.S. Pat. No. 5,716,808. The ADE2 gene sequence includes 1006 nucleotides of 5' non-coding sequence and 442 nucleotides of 3' non-coding sequence, with the initiation ATG codon at nucleotides 1007–1009 (see SEQ ID NO:1, herein). Any functional ADE2 allele can be used as a selectable marker. For example, a DNA segment comprising nucleotides 407–2851 can be used as a selectable marker, although longer or shorter segments can be used as long as the coding portion is operably linked to promoter and terminator sequences.

Other nutritional markers that can be used within the present invention include the *P. methanolica* ADE1, HIS3, and LEU2 genes, which allow for selection in the absence of adenine, histidine, and leucine, respectively. *P. methanolica* genes can be cloned on the basis of homology with their counterpart *Saccharomyces cerevisiae* genes. Heterologous genes, such as genes from other fungi, can also be used as selectable markers.

To prepare auxotrophic mutants of *P. methanolica*, cells are first exposed to environmental conditions that cause genetic mutations in the cells. Methods for mutagenizing cells are well known in the art and include chemical treatment, exposure to ultraviolet light, exposure to x-rays, and retroviral insertional mutagenesis. Chemical mutagens include ethylmethane sulfonate (EMS), N-methyl-M-nitro-N-nitrosoguanidine, 2-methoxy-6-chloro-9-(3-(ethyl-2-chloroethyl)aminopropylarnino) acridine 2HCl, 5-bromouracil, acridine, and aflatoxin (see, for example, Lawrence, *Methods Enzymol.* 194:273 (1991)). The proportion of mutagenized cells obtained is a function of the strength or amount of mutagenizing agent to which the cells are exposed. That is, a low level of mutagen produces a small proportion of mutant cells, while higher levels of mutagen produce a higher proportion of mutant cells, but also kill more cells. It is therefore necessary to balance mutagenesis with killing so that a reasonable number of mutant cells is obtained. This balance is typically determined empirically by exposing cells to different conditions to establish a killing curve. In general, the cells are exposed to mutagenizing conditions and cultured for one day, after which they are tested for viability according to standard assay methods. For example, it is possible to use a level of mutagenesis that results in 20–50% mortality, although one skilled in the art will recognize that this value can be adjusted as necessary, for example if working with a very large number of cells.

Mutagenized cells are then cultured in a rich medium to allow mutations to become established and replicated in at least a portion of the cell population. This step allows cells in which the genome has been altered to replicate the mutation and pass it on to their progeny, thereby establishing the mutation within the population.

The cells are then transferred to a culture medium deficient in assimilable nitrogen so that cellular nitrogen stores are depleted. By "deficient in assimilable nitrogen" it is meant that the medium lacks an amount of nitrogen sufficient to support growth of the cells. Depletion of cellular nitrogen stores will generally require about 12 to 24 hours of incubation, with 16 hours being sufficient under common conditions. Following depletion of nitrogen stores, the cells are cultured in a defined culture medium comprising an inorganic nitrogen source and an amount of an antifungal antibiotic sufficient to kill growing *P. methanolica* cells. The antibiotic nystatin (mycostatin) is useful for this procedure. Preferred inorganic nitrogen sources are those comprising ammonium ions, such as ammonium sulfate. In general, the medium will contain 10–200 mM ammonium, preferably about 60 mM ammonium. Nystatin is included at a concentration of 0.1 to 100 milligrams/liter, preferably 0.5 to milligrams/liter, more preferably about 2 milligrams/liter (10 units/liter). Treatment with nystatin is carried out for ten minutes to six hours, preferably about one hour. Those skilled in the art will recognize that the actual antibiotic concentration and exposure time required to kill prototrophic cells can be readily determined empirically, and certain adjustments may be necessary to compensate for variations in specific activity between individual batches of antibiotic. By depleting cellular nitrogen stores and then culturing the cells in a defined medium containing an inorganic nitrogen source and antibiotic, cells that are auxotrophic for amino acid or nucleotide biosynthesis remain alive because they cannot grow in the defined medium. Growing cells are killed by the antibiotic. Following the antibiotic treatment, the cells are transferred to a rich culture medium.

Auxotrophic mutations are confirmed and characterized by determining the nutrient requirements of the treated cells. Replica plating is commonly used for this determination. Cells are plated on both rich medium and media lacking specific nutrients. Cells that do not grow on particular plates are auxotrophic for the missing nutrient. Complementation analysis can be used for further characterization. Methods for preparing auxotrophic mutants of *P. methanolica* are described, for example, by Raymond, U.S. Pat. No. 5,736,383, and by Raymond et al., *Yeast* 14:11 (1998).

In the alternative, a dominant selectable marker is used, thereby obviating the need for mutant host cells. Dominant selectable markers are those that are able to provide a growth advantage to wild-type cells. Typical dominant selectable markers are genes that provide resistance to antibiotics, such as G418 and other neomycin-type antibiotics (kanamycin resistance gene), hygromycin B (hygromycin B-phosphotransferase gene), aureobasidin A (AUR1 gene), and bleomycin/phleomycin-type antibiotics such as ZEOCIN (ble genes), as well as ampicillin resistance genes. A particularly useful dominant selectable marker for use in *P. methanolica* is the Sh ble gene, which inhibits the activity of ZEOCIN. Genes encoding dominant selectable markers are known to those of skill in the art (see, for example, Srivastava and Schlessinger, *Gene* 103:53 (1991); Romanos et al., "Expression of Cloned Genes in Yeast," in *DNA Cloning* 2: Expression Systems, $2^{nd}$ Edition, pages 123–167 (IRL Press 1995); Markie, *Methods Mol. Biol.* 54:359 (1996); Pfeifer et al., *Gene* 188:183 (1997); Tucker and Burke, *Gene* 199:25 (1997); Hashida-Okado et al., *FEBS Letters* 425:117 (1998)).

(b) Methods for Inhibiting In Vivo Proteolysis of Heterologous Proteins

Minimization of spurious proteolysis of recombinant peptides or polypeptides generated under high cell density fermentation conditions is highly desirable. In yeast, the major store of proteolytic activity is located within the lumen of the vacuolar compartment (Jones, *Methods Enzymol.* 194:428 (1991)). These proteases are released into the fermentation broth by spontaneous and inevitable cell lysis and are further liberated during cell breakage that is required to release intracellularly produced proteins in laboratory or industrial production. Although vacuolar proteases are required for several developmental transitions in the life cycle of yeast cells (e.g., sporulation), they are dispensable for vegetative growth.

The majority of vacuolar proteases are synthesized and transported through the secretory pathway as enzymatically inactive zymogens (Klionsky et al., *Microbiol. Rev.* 54:266 (1990); Raymond et al., *Int. Rev. Cytol.* 139:59 (1992)). These zymogens are proteolytically activated by the combined action of proteinase A, the product of the PEP4 gene, and proteinase B, the product of the PRB1 gene. Therefore, suitable protease deficient strains have functional deficiencies in the vacuolar proteases proteinase A, which is encoded by the PEP4 gene (pep4 mutant), and proteinase B, which is encoded by the PRB1 gene (prb1 mutant). Fragments of the *Pichia methanolica* PRB1 and PEP4 genes are disclosed in SEQ ID NOs: 4 and 5, respectively, while SEQ ID NO:6 presents the corresponding PEP4 amino acid sequence.

PEP4 and PRB1 gene deficiencies are created by mutations causing partial or complete loss of gene function. Preferably, the mutation results in structural change in one or more regions of the encoded protein that are required for activity. Mutations can be point mutations, more preferably insertions, and most preferably deletions of up to the entire open reading frame of the target gene. Mutations spanning small regions (including point mutations, small insertions, and small deletions) will generally be directed to coding regions for structural motifs required for activity or will create frame shifts that eliminate protein activity. Those skilled in the art will recognize that, in addition to mutations within the open reading frame, mutations in untranslated regions of the gene can also reduce or negate gene function. When mutating untranslated sequences, it is preferred to target sequences within 1 kilobase of the open reading frame.

Vacuolar protease-deficient strains of *P. methanolica* can be constructed by a variety of genetic manipulations as disclosed above, any of which result in the reduction or lack of functional protease. See, for example, Raymond and Vanaje, U.S. Pat. No. 6,001,597. As an illustration, genetic defects can be generated by deleting a segment of the parent gene encoding the protease of interest. Such deletions will preferably eliminate one or more active site amino acid residues, thereby destroying proteolytic activity. Frameshift mutations, for example, can be generated by deleting a partial codon, thus deletion of a single nucleotide, and preferably at least four nucleotides, can produce the desired inactivating mutation. It is preferred, however, to delete most or all of the open reading frame of the parent gene, although in practice the actual extent of any deletion will be based on the locations of convenient restriction enzyme recognition sites. As noted above, vacuolar protease genes of particular interest in this regard include the PEP4 gene, which encodes proteinase A, and the PRB1 gene, which encodes proteinase B. Although other vacuolar proteases (e.g., carboxypeptidase Y) are present in *P. methanolica*, the PEP4 and PRB1 gene products activate the other vacuolar proteases, so that negation of PEP4 and PRB1 functions results in a strain that is effectively vacuolar protease negative.

In contrast to other yeasts, including *S. cerevisiae* and *Pichia pastoris*, the PEP4 gene product of *P. methanolica* is not the dominant vacuolar proteolytic enzyme within this organism. *P. methanolica* pep4 mutants were not functionally deficient in vacuolar activity, whereas pep4 prb1 double mutants were found to be functionally deficient in protease activity. The data indicate that proteinase A autoactivates within the vacuole or a pre-vacuolar compartment, probably in response to low pH and the presence of $Ca^{++}$ and/or other ions. The activated enzyme then activates proteinase B, a non-specific proteinase which activates other vacuolar proteolytic enzymes. The data further indicate that proteinase B can be activated via alternative pathways.

A suitable method for creating a deletion within a vacuolar protease gene employs a loop-in/loop-out mutagenesis technique, whereby a disrupted copy of the protease gene is used to replace the endogenous copy within the genome. A deletion is created in a cloned vacuolar protease gene, typically by restriction endonuclease digestion and re-ligation or by the polymerase chain reaction (PCR; Mullis, U.S. Pat. No. 4,683,202). The disrupted copy of the gene is then introduced into the cell. It is preferred to utilize a linearized plasmid comprising, in addition to the disrupted protease gene, a selectable marker as disclosed in more detail below. The presence of the selectable marker facilitates the identification and selection of integrative transformants. Transformants that have undergone the desired homologous integration event are identified by Southern blotting (see, e.g., Strathern and Higgins, *Methods Enzymol.* 194:319 (1991)). Genomic DNA is prepared from transformants and control cells, digested with one or more restriction enzymes, transferred to a blot, and probed to detect a change in the restriction pattern following transformation. Reagents, materials, equipment and protocols for preparing and probing blots are available from commercial suppliers.

Vacuolar protease activity (and therefore vacuolar protease deficiency) is measured using any of several known assays. Suitable assays include those developed for *Saccharomyces cerevisiae* and disclosed by Jones, *Methods Enzymol.* 194:428 (1991). For example, one assay is the APE overlay assay, which detects activity of carboxypeptidase Y (CpY). Briefly, the assay detects the carboxypeptidase Y-mediated release of β-naphthol from an ester, which results in the formation of an insoluble red dye by the reaction of the β-naphthol with the diazonium salt Fast Garnet GBC. Colonies are overlayed with a 0.6% agar solution of N-Acetyl-DL-phenylalanine β-naphthyl ester containing 1 mg/ml dimethylfomiamide. After the overlay hardens, the plates are flooded with a solution of Fast Garnet GBC (5 mg/ml in 0.1 M Tris-HCl, pH 7.3–7.5). Within a few minutes, Cpy$^+$ colonies turn red. Carboxypeptidase Y activity can also be detected by the well test, in which cells are distributed into wells of a microtiter test plate and incubated in the presence of N-benzoyl-L-tyrosine p-nitroanilide (BTPNA) and dimethylformamide. The cells are permeabilized by the dimethylformamide, and CpY in the cells cleaves the amide bond in the BTPNA to give the yellow product p-nitroaniline. Assays for CpY will detect any mutation that reduces protease activity so long as that activity ultimately results in the reduction of CpY activity. Proteinase B activity can be detected using an HPA overlay test, which detects the solubilization of Hide Powder Azure by proteinase B. Colonies producing the enzyme are surrounded by a clear halo, while deficient mutants remain covered. Carboxypeptidase S can be assayed using a well test that detects the release of leucine from carbobenzoxyglycyl-L-leucine. In the presence of L-amino-acid oxidase, $H_2O_2$ is produced by the oxidation of the free leucine. The $H_2O_2$ reacts with o-dianisidine dihydrochloride in the presence of peroxidase to produce oxidized dianisidine, which is dark brown. Additional assays are known and within the level of ordinary skill in the art to perform. Methods for producing protease-deficient *P. methanolica* are described, for example, by Raymond et al., *Yeast* 14:11 (1998).

Other strategies to minimize proteolytic degradation include saturating proteases by adding casamino acids or peptone to the culture medium, and counteracting neutral proteases by reducing the pH level of the culture medium to about 3.0 (see, for example, Gellissen et al., "Gene Expression in Methylotrophic Yeasts," in *Gene Expression in Recombinant Microorganisms,* Smith (ed.), pages 195–239 (Marcel Dekker Inc. 1994)).

(c) Methods for Producing Pichia With Decreased Methanol Metabolism

For large-scale, industrial processes where it is desirable to minimize the use of methanol, host cells may be used that have a genetic defect in a gene required for methanol utilization. Such genes include the alcohol oxidase genes AUG1 and AUG2, as well as genes encoding catalase, formaldehyde dehydrogenase, formate dehydrogenase, dihydroxyacetone synthase, dihydroxyacetone kinase, fructose 1,6-bisphosphate aldolase, and fructose 1,6-bisphosphatase. It is particularly advantageous to use cells in which both alcohol oxidase genes (AUG1 and AUG2) are deleted. Methods for producing *Pichia methanolica* strains that have a defect in AUG1, AUG2, or both AUG1 and AUG2 genes are described by Raymond et al., *Yeast* 14:11 (1998), by Raymond, U.S. Pat. No. 5,716,808, and by Raymond et al., U.S. Pat. No. 5,736,383.

(d) Transformation Vectors and Methods

Nucleic acid molecules for transforming *P. methanolica* will commonly be prepared as double-stranded, circular plasmids, which are preferably linearized prior to transformation. For polypeptide or protein production, the nucleic acid molecules will include, in addition to the selectable marker disclosed above, an expression cassette comprising a transcription promoter, a gene (e.g., a cDNA) encoding the polypeptide or protein of interest, and a transcription terminator (e.g., an AUG1 terminator, an AOX1 terminator, etc.). These elements are operably linked to provide for transcription of the gene of interest. Suitable promoters and terminators are derived from a *P. methanolica* gene. Useful promoters include those from constitutive and methanol-inducible promoters. Promoter sequences are generally contained within 1.5 kilobases upstream of the coding sequence of a gene, often within one kilobase or less. In general, regulated promoters are larger than constitutive promoters due the presence of regulatory elements. Methanol-inducible promoters, which include both positive and negative regulatory elements, may extend more than one kilobase upstream from the initiation ATG. Promoters are identified by function and can be cloned according to known methods.

Exmaples of suitable methanol-inducible promoters include promoters of the *Pichia pastoris* alcohol oxidase 1 (AOX1) gene and the promoter of the *Candida boidinji* alcohol oxidase gene (see, for example, Rodriguez et al., *Yeast* 12:815 (1996); Saki et al., U.S. Pat. No. 5,750,372). A particularly useful methanol-inducible promoter is that of a *P. methanolica* alcohol utilization gene. A representative coding strand sequence of one such gene, AUG1, is disclosed by Raymond et al., *Yeast* 14:11 (1998), and as SEQ ID NO:2 by Raymond, U.S. Pat. No. 5,716,808. In this nucleotide sequence, the initiation ATG codon is at nucleotides 1355–1357 (see SEQ ID NO:2, herein). Nucleotides 1–23 of SEQ ID NO:2 are a non-AUG1 polylinker sequence. An example of a usefuil AUG1 promoter is a segment comprising nucleotides 24–1354 of SEQ ID NO:2, although additional upstream sequence can be included.

*P. methanolica* contains a second alcohol utilization gene, AUG2, the promoter of which can also be used within the present invention. A partial DNA sequence of one AUG2 clone is shown in SEQ ID NO:9 of the Raymond '808 patent, which is included as SEQ ID NO:3, herein. AUG2 promoter segments generally comprise nucleotides 91–169 of SEQ ID NO:3, although small truncations at the 3' end would not be expected to negate promoter function.

Other useful promoters include those of the dihydroxyacetone synthase (DHAS), formate dehydrogenase (FMD), and catalase (CAT) genes. Genes encoding these enzymes from other species have been described, and their sequences are available (e.g., Janowicz et al., *Nucl. Acids Res.* 13:2043 (1985); Hollenberg and Janowicz, EPO publication 0 299 108; Didion and Roggenkamp, *FEBS Lett.* 303:113 (1992)). Genes encoding these proteins can be cloned by using the known sequences as probes, or by aligning known sequences, designing primers based on the alignment, and amplifying *P. methanolica* DNA by the polymerase chain reaction.

Suitable constitutive promoters for use within the present invention include those from glyceraldehyde-3-phosphate dehydrogenase, triose phosphate isomerase, and phosphoglycerate kinase genes of *P. methanolica*. These genes can be cloned as disclosed above or by complementation in a host cell, such as a *Saccharomyces cerevisiae* cell, having a mutation in the counterpart gene. Mutants of this type are well known in the art. See, for example, Kawasaki and Fraenkel, *Biochem. Biophys. Res. Comm.* 108:1107 (1982), McKnight et al., *Cell* 46:143 (1986), and Aguilera and Zimmermann, *Mol. Gen. Genet.* 202:83 (1986).

An illustrative glyceraldehyde-3-phosphate dehydrogenase ("GAP") promoter is the *Pichia pastoris* GAP promoter described by Waterham et al., *Gene* 186:37 (1997). Saccharomyces GAP promoters are also known to those of skill in the art (see, for example, Horii et al., U.S. Pat. No. 4,945,046; Mukai et al., U.S. Pat. No. 5,021,339; Rosenberg et al., U.S. Pat. No. 5,089,398).

Another suitable GAP promoter is a *Pichia methanolica* GAP promoter. The sequence of a DNA molecule comprising a *Pichia methanolica* GAP gene promoter, coding region, and terminator is shown in SEQ ID NO:8. The gene has been designated GAP1. Within SEQ ID NO:8, the open reading frame begins with the methionine codon (ATG) at nucleotides 1733 to 1735. The transcription promoter is located upstream of the ATG. Gene expression experiments showed that a functional promoter was contained within the approximate 900 nucleotide 5'-flanking region of the GAP1 gene. Analysis of this promoter sequence revealed the presence of a number of sequences homologous to *Saccharomyces cerevisiae* promoter elements. These sequences include a consensus TATAAA box at nucleotides 1584 to 1591, a consensus Rap1p binding site (Graham and Chambers, *Nucl. Acids Res.* 22:124 (1994)) at nucleotides 1355 to 1367, and potential Gcr1p binding sites (Shore, *Trends Genet.* 10:408 (1994)) at nucleotides 1225 to 1229, 1286 to 1290, 1295 to 1299, 1313 to 1317, 1351 to 1354, 1370 to 1374, 1389 to 1393, and 1457 to 1461. While not wishing to be bound by theory, it is believed that these sequences may perform functions similar to those of their counterparts in the *S. cerevisiae* TDH3 promoter (Bitter et al., *Mol. Gen. Genet.* 231:22 (1991)), and therefore, they may bind the homologous transcription regulatory elements. Mutation of the region around the consensus Gcr1p binding site in the *P. methanolica* GAP1 promoter has been found to destroy promoter activity.

SEQ ID NO:10 shows the nucleotide sequence for the GAP2 gene, which has an open reading frame that begins with the methionine codon (ATG) at nucleotides 1093 to 1095. The transcription promoter is located upstream of the ATG. Gene expression experiments showed that a functional promoter was contained within the approximate 1000 nucleotide 5'-flanking region of the GAP2 gene.

Suitable portions of the GAP1 and GAP2 sequences for use within the present invention as transcription promoters include segments comprising at least 900 contiguous nucleotides of the 5' non-coding region of SEQ ID NOs:8 and 10, and, preferably, comprising nucleotide 810 to nucleotide 1724 of the sequence shown in SEQ ID NO:8, or comprising nucleotide 93 to nucleotide 1080 of the sequence shown in SEQ ID NO: 10. Those skilled in the art will recognize that longer portions of the 5' non-coding region of the *P. methanolica* GAP1 and GAP2 genes can also be used. For example, promoter sequences can include the sequence of SEQ ID NO:8 through nucleotide 1732 in the 3' direction and can extend to or beyond nucleotide 232 in the 5' direction, or the sequence of SEQ ID NO:10 through nucleotide 1092 in the 3' direction and can extend to or beyond nucleotide 1 in the 5' direction. In general, the promoter used within an expression DNA construct will not exceed 1.5 kilobases in length, and certain embodiments do not exceed 1.0 kilobases in length.

Studies have shown that the sequence of SEQ ID NO:8 from nucleotide 810 to 1724, and SEQ ID NO:10 from nucleotide 93 to 1080 provides a functional transcription promoter. However, additional nucleotides can be removed from either or both ends of either sequence and the resulting sequence tested for promoter function by joining it to a nucleotide sequence encoding a protein, preferably a protein for which a convenient assay is readily available.

Within the present invention, it is preferred that the GAP1 promoter be substantially free of GAPI gene coding sequence, which begins with nucleotide 1733 in SEQ ID NO:8, and that that the GAP2 promoter be substantially free of GAP2 gene coding sequence, which begins with nucleotide 1093 in SEQ ID NO:10. As used herein, the term "substantially free of GAP1 gene coding sequence" means that the promoter DNA includes not more than 15 nucleotides of the GAP1 or GAP2 coding sequences, preferably not more than 10 nucleotides, and more preferably not more than 3 nucleotides. Within certain embodiments of the invention, a GAP promoter is provided free of coding sequence of the *P. methanolica* GAP1 or GAP2 genes.

However, those skilled in the art will recognize that a GAP1 or a GAP2 gene fragment that includes the initiation ATG can be operably linked to a heterologous coding sequence that lacks an ATG, with the GAP ATG providing for initiation of translation of the heterologous sequence. Those skilled in the art will further recognize that additional GAP1 or GAP2 coding sequences can also be included, whereby a fusion protein comprising GAP1 or GAP2 and heterologous amino acid sequences is produced.

Such a fusion protein may comprise a cleavage site to facilitate separation of the GAP1, or GAP2, and heterologous sequences subsequent to translation.

As noted above, the expression vectors can include a transcription terminator sequence. Such transcription terminators can be provided by nucleotide sequences of the *Pichia methanolica* GAP genes. For example, a consensus transcription termination sequence (Chen and Moore, *Mol. Cell. Biol.* 12:3470 (1992)) resides at nucleotides 2774 to 2787 of SEQ ID NO:8, and at nucleotides 2136 to 2145 of SEQ ID NO:10. Within the present invention, there are thus provided transcription terminator gene segments of at least about 50 base pairs, at least about 60 base pairs, at least 90 base pairs, or about 200 base pairs in length. These segments comprise the termination sequence disclosed above, and can have as their 5' termini nucleotide 2735 of SEQ ID NO:8, or 2095 of SEQ ID NO:10. Those skilled in the art will recognize, however, that the transcription terminator segment that is provided in an expression vector can include at its 5' terminus the TAA translation termination codon at nucleotides 2732 to 2734 of SEQ ID NO:8, or nucleotides 2092 to 2094 of SEQ ID NO:10, to permit the insertion of coding sequences that lack a termination codon.

The DNA constructs used within the present invention may further contain additional elements, such as an origin of replication and a selectable marker that allow amplification and maintenance of the DNA in an alternate host (e.g., *E. coli*). To facilitate integration of the DNA into the host chromosome, it is preferred to have the entire expression segment, comprising the promoter-gene of interest-terminator plus selectable marker, flanked at both ends by host DNA sequences. This is conveniently accomplished by including 3' untranslated DNA sequence at the downstream end of the expression segment and relying on the promoter sequence at the 5' end. When using linear DNA, the expression segment will be flanked by cleavage sites to allow for linearization of the molecule and separation of the expression segment from other sequences (e.g., a bacterial origin of replication and selectable marker). Preferred cleavage sites are those that are recognized by restriction endonucleases that cut infrequently within a DNA sequence, such as those that recognize eight-base target sequences (e.g., NotI).

An expression vector comprising a secretory signal sequence can be used to drive expression of secreted heterologous proteins. Since Pichia secretes very few of its own proteins, secretion of the heterologous protein provides a first step in purification of the heterologous protein. A secretory peptide typically consists of about 20 amino acids and has a hydrophobic core of 6 to 15 amino acids followed by hydrophilic amino acid residues. Suitable secretory signal sequences include derived from *Saccharomyces cerevisia* invertase gene (SUC2), acid phosphatase gene (PHO1 and PHO5), *Pichia pastoris* alkaline phosphatase gene, *Saccharomyces cerevisiae* α mating factor (MFα1), as well as a synthetic hybrid based on the PHO1 sequence with an additional 19 residues including a Kex2 cleavage site (see, for example, Laroche et al., *Biotechnology* 12:1119 (1994), Romanos, *Curr. Opin. Biotech.* 6:527 (1995), and Sbema et al., *Austalas. Biotechnol.* 6:82 (1996)).

Proteins that can be produced in *P. methanolica* include proteins of industrial and pharmaceutical interest. Such proteins include enzymes such as lipases, cellulases, and proteases; enzyme inhibitors, including protease inhibitors; growth factors such as platelet derived growth factor, fibroblast growth factors, and epidermal growth factor; immunomodulators such as erythropoietin and thrombopoietin; and hormones such as insulin, leptin, and glucagon. For example, Pichia has been used to produce labeled proteins for structural studies (e.g., polypeptides labeled with $^{13}C$, $^{15}N$, or double-labeled with both isotopes), vaccines (e.g., cattle tick antigen), coagulation inhibitors and fibrolytic compounds (e.g., hirudin, plasminogen activator), protease inhibitors, hormones, and cytokines, diagnostic compounds, allergens (e.g., cytomegalovirus antigenic protein), antibodies, receptors (e.g., $5HT_{5A}$ serotonin receptor and human μ-opioid receptor), receptor ligands, and various enzymes (e.g., enzymes for blood group conversion, spinach phosphoribulokinase, bovine enterokinase). See, for example, Romanos, *Curr. Opin. Biotech.* 6:527 (1995), Sberna et al., *Austalas. Biotechnol* 6:82 (1996); Sudbery, *Curr. Opin. Biotech.* 7:517 (1996), international publication No. WO 98/20035, and Higgens and Cregg (eds.), *Pichia Protocols*, pages 249–261 (Humana Press, Inc. 1998).

Pichia can produce heterologous proteins that remain within cells or that are secreted into the culture medium. For example, heterologous proteins that remain with Pichia cells include β-galactosidase, tumor necrosis factor, hepatitis B surface antigen, tetanus toxin fragment C, streptokinase, and HIV gp 20. On the other hand, heterologous proteins that have been secreted by Pichia include invertase, bovine lysozyme, human serum albumin, human epidermal growth factor, Kunitz protease inhibitor, rabbit monoclonal antibody, cathepsin E, α-amylase, HIV gp 120, enterokinase, α-galactosidase, single chain Fv antibody fragments, Factor XII, oncostatin M, antibody receptors, interferon-τ, and human growth hormone.

Heterologous DNA can be introduced into *P. methanolica* cells by any of several known methods, including lithium transformation (Hiep et al., *Yeast* 9:1189–1197 (1993); Tarutina and Tolstorukov, *Abst. of the 15th International Specialized Symposium on Yeasts*, Riga (USSR), 1991, 137; Ito et al., *J Bacteriol.* 153:163 (1983); Bogdanova et al., *Yeast* 11:343 (1995), spheroplast transformation (Beggs, *Nature* 275:104 (1978); Hinnen et al., *Proc. Natl. Acad. Sci. USA* 75:1929 (1978); Cregg et al., *Mol. Cell. Biol.* 5:3376 (1985)), freeze-thaw polyethylene glycol transformation (Pichia Expression Kit Instruction Manual; Invitrogen Corp., San Diego, Calif., Cat. No. K1710-01), or electroporation. Electroporation is the process of using a pulsed electric field to transiently permeabilize cell membranes, allowing macromolecules, such as DNA, to pass into cells. Electroporation has been described for use with mammalian (e.g., Neumann et al., *EMBO J* 1:841–845 (1982)) and fungal (e.g., Meilhoc et al., *Bio/Technology* 8:223–227 (1990)) host cells. Methods for transforming *P. methanolica* are described, for example, by Raymond, U.S. Pat. No. 5,716,808, Raymond, U.S. Pat. No. 5,736,383, and by Raymond et al., *Yeast* 14:11 (1998).

As an illustration, electroporation of *P. methanolica* is carried out on cells in early log phase growth. Cells are streaked to single colonies on solid media, such as solid YEPD. After about two days of growth at 30° C., single colonies from a fresh plate are used to inoculate the desired volume of rich culture media (e.g., YEPD) to a cell density of about 5 to 10×10$^5$ cells/ml. Cells are incubated at about 25–35° C., preferably 30° C., with vigorous shaking, until they are in early log phase. The cells are then harvested, such as by centrifugation at 3000×g for 2–3 minutes, and resuspended. Cells are made electrocompetent by reducing disulfide bonds in the cell walls, equilibrating them in an ionic solution that is compatible with the electroporation conditions, and chilling them. Cells are typically made electrocompetent by incubating them in a buffered solution at pH 6–8 containing a reducing agent, such as dithiothreitol (DTT) or β-mercaptoethanol (BME), to reduce cell wall proteins to facilitate subsequent uptake of DNA. A suitable incubation buffer in this regard is a fresh solution of 50 mM potassium phosphate buffer, pH 7.5, containing 25 mM DTT. The cells are incubated in this buffer (typically using one-fifth the original culture volume) at about 30° C. for about 5 to 30 minutes, preferably about 15 minutes. The cells are then harvested and washed in a suitable electroporation buffer, which is used ice-cold. Suitable buffers in this regard include pH 6–8 solutions containing a weak buffer, divalent cations (e.g., $Mg^{++}$, $Ca^{++}$) and an osmotic stabilizer (e.g., a sugar). After washing, the cells are resuspended in a small volume of the buffer, at which time they are electrocompetent and can be used directly or aliquotted and stored frozen (preferably at −70° C.). A preferred electroporation buffer is STM (270 mM sucrose, 10 mM Tris, pH 7.5, 1 mM $MgCl_2$). Within a preferred protocol, the cells are subjected to two washes, first in the original culture volume of ice-cold buffer, then in one-half the original volume. Following the second wash, the cells are harvested and resuspended, typically using about 3–5 milliliters of buffer for an original culture volume of 200 ml.

Electroporation is performed using a small volume of electrocompetent cells (typically about 100 μl) and up to one-tenth volume of linear DNA molecules.

For example, 0.1 ml of cell suspension in a buffer not exceeding 50 mM in ionic strength is combined with 0.1–10 μg of DNA (vol. ≦10 μl). This mixture is placed in an ice-cold electroporation cuvette and subjected to a pulsed electric field of from 2.5 to 4.5 kV/cm, preferably about 3.75 kV/cm, and a time constant of from 1 to 40 milliseconds, preferably 10–30 milliseconds, more preferably 15–25 milliseconds, most preferably about 20 milliseconds, with exponential decay. The actual equipment settings used to achieve the desired pulse parameters will be determined by the equipment used. When using a Bio-Rad Laboratories, Inc. (Hercules, Calif.) GENE PULSER electroporator with a 2 mm electroporation cuvette, resistance is set at 600 ohms or greater, preferably "infinite" resistance, and capacitance is set at 25 µF to obtain the desired field characteristics. After being pulsed, the cells are diluted approximately 10× into one milliliter of YEPD broth and incubated at 30° C. for one hour.

The cells are then harvested and plated on selective media. Within a preferred embodiment, the cells are washed once with a small volume (equal to the diluted volume of the electroporated cells) of 1× yeast nitrogen base (6.7 grams/liter yeast nitrogen base without amino acids; Difco Laboratories, Detroit, Mich.), and plated on minimal selective media. Cells having an ade2 mutation that have been transformed with an ADE2 selectable marker can be plated on a minimal medium that lacks adenine, such as ADE D or ADE DS. In a typical procedure, 250 µl aliquots of cells are plated on 4 separate ADE D or ADE DS plates to select for Ade$^+$ cells. Methods for transforming P. methanolica are described, for example, by Raymond et al., U.S. Pat. No. 5,854,039, and Raymond et al., Yeast 14:11 (1998).

P. methanolica recognizes certain infrequently occurring sequences, termed autonomously replicating sequences (ARS), as origins of DNA replication, and these sequences may fortuitously occur within a DNA molecule used for transformation, allowing the transforming DNA to be maintained extrachromosomally. However, integrative transformants are generally preferred for use in protein production systems. Integrative transformants have a profound growth advantage over ARS transformants on selective media containing sorbitol as a carbon source, thereby providing a method for selecting integrative transformants from among a population of transformed cells. ARS sequences have been found to exist in the ADE2 gene and, possibly, the AUG1 gene of P. methanolic. Ade2 host cells of Pichia methanolica transformed with an ADE2 gene can thus become Ade$^+$ by at least two different modes. The ARS within the ADE2 gene allows unstable extrachromosomal maintenance of the transforming DNA (Hiep et al., Yeast 9:1189 (1993)). Colonies of such transformants are characterized by slower growth rates and pink color due to prolific generation of progeny that are Ade$^-$. Transforming DNA can also integrate into the host genome, giving rise to stable transformants that grow rapidly, are white, and that fail to give rise to detectable numbers of Ade$^-$ progeny. ADE D plates allow the most rapid growth of transformed cells, and unstable and stable transformants grow at roughly the same rates. After 3–5 days of incubation on ADE D plates at 30° C. stable transformant colonies are white and roughly twice the size of unstable, pink transformants. ADE DS plates are more selective for stable transformants, which form large (about 5 mm) colonies in 5–7 days, while unstable (ARS-maintained) colonies are much smaller (about 1 mm). The more selective ADE DS media is therefore preferred for the identification and selection of stable transformants. For some applications, such as the screening of genetically diverse libraries for rare combinations of genetic elements, it is sometimes desirable to screen large numbers of unstable transformants, which have been observed to outnumber stable transformants by a factor of roughly 100. In such cases, those skilled in the art will recognize the utility of plating transformant cells on less selective media, such as ADE D.

Integrative transformants are preferred for use in protein production processes. Such cells can be propagated without continuous selective pressure because DNA is rarely lost from the genome. Integration of DNA into the host chromosome can be confirmed by Southern blot analysis. Briefly, transformed and untransformed host DNA is digested with restriction endonucleases, separated by electrophoresis, blotted to a support membrane, and probed with appropriate host DNA segments. Differences in the patterns of fragments seen in untransformed and transformed cells are indicative of integrative transformation. Restriction enzymes and probes can be selected to identify transforming DNA segments (e.g., promoter, terminator, heterologous DNA, and selectable marker sequences) from among the genomic fragments.

Differences in expression levels of heterologous proteins can result from such factors as the site of integration and copy number of the expression cassette and differences in promoter activity among individual isolates. It is therefore advantageous to screen a number of isolates for expression level prior to selecting a production strain. A variety of suitable screening methods are available. For example, transformant colonies are grown on plates that are overlayed with membranes (e.g., nitrocellulose) that bind protein. Proteins are released from the cells by secretion or following lysis, and bind to the membrane. Bound protein can then be assayed using known methods, including immunoassays. More accurate analysis of expression levels can be obtained by culturing cells in liquid media and analyzing conditioned media or cell lysates, as appropriate. Methods for concentrating and purifying proteins from media and lysates will be determined in part by the protein of interest. Such methods are readily selected and practiced by the skilled practitioner.

4. Culture of Transformed Pichia

For small-scale protein production (e.g. plate or shake flask production), Pichia transformants that carry an expression cassette comprising a methanol-regulated promoter (such as the AUG1 promoter) are grown in the presence of methanol and the absence of interfering amounts of other carbon sources (e.g., glucose). For small-scale experiments, including preliminary screening of expression levels, transformants, such as Pichia methanolica, may be grown at 30° C. on solid media containing, for example, 20 grams/liter Bacto-agar (Difco), 6.7 grams/liter yeast nitrogen base without amino acids (Difco), 10 grams/liter methanol, 0.4 jg/liter biotin, and 0.56 gram/liter of-Ade-Thr -Trp powder. Because methanol is a volatile carbon source it is readily lost on prolonged incubation. A continuous supply of methanol can be provided by placing a solution of 50% methanol in water in the lids of inverted plates, whereby the methanol is transferred to the growing cells by evaporative transfer. In general, not more than one milliliter of methanol is used per 100-nun plate. Slightly larger scale experiments can be carried out using cultures grown in shaker flasks. In a typical procedure, cells are cultivated for two days on minimal methanol plates, as disclosed above, at 30° C., and then colonies are used to inoculate a small volume of minimal methanol media (6.7 grams/liter yeast nitrogen base without amino acids, 10 grams/liter methanol, 0.4 µg/liter biotin) at a cell density of about 1×10$^6$ cells/ml. Cells are grown at 30° C. Cells growing on methanol have a high oxygen requirement, necessitating vigorous shaking during cultivation. Methanol is replenished daily (typically 1/100 volume of 50% methanol per day).

For protein production, Pichia cells are cultured in a medium comprising adequate sources of carbon, nitrogen and trace nutrients at a temperature of about 25° C. to 35° C. Liquid cultures are provided with sufficient aeration by conventional means, such as shaking of small flasks or sparging of fermentors. A preferred culture medium is YEPD. The components of YEPD and other media are described above. Typically, plates containing these media are produced by adding 1.8% BACTO agar (Difco Laboratories, Inc.; Detroit, Mich.).

The cells may be passaged by dilution into fresh culture medium or stored for short periods on plates under refrigeration. For long-term storage, the cells are preferably kept in a 50% glycerol solution at −70° C.

As an illustration, one to two colonies of a *P. methanolica* strain can be picked from a fresh agar plate (e.g, YEPD agar) and suspended in 250 ml of YEPD broth contained in a two liter baffled shake flask. The culture is grown for 16 to 24 hours at 30° C. and 250 rpm shaking speed. Approximately 50 to 80 milliliters of inoculum are used per liter starting fernentor volume (5–8% v/v inoculum).

A BIOFLO 3000 fermentor system (New Brunswick Scientific Company, Inc.; Edison, N.J.) can be used for fermentation development. This fermentor system can handle either a six liter or a fourteen liter fermentor vessel. Fermentations performed with the six liter vessel are prepared with three liters of medium, whereas fermentations performed with the fourteen liter vessel are prepared with six liters of medium.

A suitable medium of the present invention is a soluble, minimal medium comprising glucose as a carbon source, inorganic ammonia, potassium, phosphate, iron, biotin, and citric acid. As used herein, a "soluble medium" is a medium that does not contain visible precipitation. Preferably, the medium lacks phosphate glass (sodium hexametaphosphate). In certain embodiments, the medium is prepared in deionized water and does not contain calcium sulfate. As a minimal medium, it is preferred that the medium is not prepared by adding polypeptides or peptides, such as yeast extracts. A soluble minimal medium that "consists essentially of" certain recited components (e.g., water, glucose, inorganic ammonia, potassium, phosphate, iron, citric acid, and the like) is a medium was not prepared by adding polypeptides or proteins, such as yeast extracts. Nevertheless, minimal medium can be supplemented with acid hydrolyzed casein (e.g., casamino acids or amicase) if desired to provide an enriched medium.

An illustrative fermentation minimal medium is prepared by mixing the following compounds to make "solution 1": $(NH_4)_2SO_4$ (11.5 grams/liter), $K_2HPO_4$ (2.60 grams/liter), $KH_2PO_4$ (9.50 grams/liter), $FeSO_4.7H_2O$ (0.40 grams/liter), and citric acid (1.00 gram/liter). After adding distilled, deionized water to one liter, solution 1 is sterilized by autoclaving, allowed to cool, and then supplemented with the following: 60% (w/v) glucose solution (47.5 milliliters/liter), 10× trace metals solution (20.0 milliliters/liter), 1 M $MgSO_4$ (20.0 milliliters/liter), and vitamin stock solution (2.00 milliliters/liter). The 10x trace metals solution contains $FeSO_4.7H_2O$ (100 mM), $CuSO_4.5H_2O$ (2 mM), $ZnSO_4.7H_2O$ (8 mM), $MnSO_4.H_2O$ (8 mM), $CoCl_2.6H_2O$ (2 mM), $NaMoO_4.2H_2O$ (1 mM), $H_3BO_3$ (8 mM), KI (0.5 mM), $NiSO_4.6H_2O$ (1 MM), thiamine (0.50 grams/liter), and biotin (5.00 milligrams/liter). The vitamin stock solution contains inositol (47.00 grams/liter), pantothenic acid (23.00 grams/liter), pyrodoxine (1.20 grams/liter), thiamine (5.00 grams/liter), and biotin (0.10 gram/liter).

Those of skill in the art can vary these particular ingredients and amounts. For example, ammonium sulfate can be substituted with ammonium chloride, or the amount of ammonium sulfate can be varied, for example, from about 11 to about 22 grams/liter. Additional variations are shown in Examples 9 and 10, in which the concentrations of the solution 1 salts were halved or increased by 50%, compared with the concentrations provided in the illustrative minimal medium. These particular variations are summarized in Table 1.

TABLE 1

| | Concentrations of Solution 1 Salts (grams/liter) | | |
|---|---|---|---|
| Salt | Illustrative Medium | Example 9 Medium | Example 10 Medium |
| $(NH_4)_2SO_4$ | 11.5 | 5.75 | 23.0 |
| $K_2HPO_4$ | 2.60 | 1.30 | 5.20 |
| $KH_2PO_4$ | 9.50 | 4.75 | 19.0 |
| $FeSO_4.7H_2O$ | 0.40 | 0.20 | 0.80 |
| citric acid | 1.00 | 0.50 | 2.00 |

In a fed-batch approach, approximately two liters of glucose feed are required per six liters fermentation, while about four liters of glucose feed are required for the fermentation in the 14 liter vessel. An illustrative glucose feed contains 900 milliliters of 60% (w/v) glucose, 60 milliliters of 50% (w/v) $(NH_4)_2SO_4$, 60 milliliters of 10× trace metals solution, and 30 milliliters of 1 M $MgSO_4$. Although this glucose feed contains 53% glucose, the amount of glucose can be varied, for example, between 50% to 60%. In addition, the rate of glucose feed delivery can be varied, for example, between 25 to 50 grams of feed per hour per six liter vessel. Moreover, a suitable glucose feed can lack components of the illustrative glucose feed, such as ammonium sulfate, trace metals, and magnesium sulfate, as shown in Example 11. The fermentor vessel operating temperature is typically set to 30° C. for the course of the fermentation. The temperature can range between 27–31° C. depending on the protein expressed.

After addition of trace metals and vitamins, the pH of the medium is typically adjusted to pH 4.5 by addition of 10% $H_3PO_4$. Generally, about 10 milliliters/liter are added, and no additional acid addition will be required. During fermentation, the pH is maintained between about 3.5 to about 5.5, or about 4.0 to about 5.0, depending on protein produced, by addition of 5 N $NH_4OH$.

The BIOFLO 3000 fermentation system has a built-in, three-level cascade loop for controlling dissolved oxygen concentrations during fermentation. The Pichia fermentation is robust and requires high agitation, aeration, and oxygen sparging to maintain the percentage dissolved oxygen saturation above 30%. The percentage dissolved oxygen should not drop below 15% for optimal expression and growth. For dissolved oxygen control with the BIOFLO 3000, typical initial settings are: agitation=350 rpm; aeration=0.5 vvm (i.e., air flow rate divided by the volume of the fermentor), and % $O_2$ addition=0. No back pressure is used. Maximum settings are: agitation=900 rpm, aeration=1.5 wm and % $O_2$=15% to 35%. If oxygen sparging is not available, then aeration can be set to 2 vvm and 0.5 bar back pressure applied to maintain a positive dissolved oxygen concentration.

The fermentation is typically initiated in a batch mode in minimal medium containing about 25 grams/liter glucose. This initial glucose is often used by approximately 10 hours elapsed fermentation time (EFT). A glucose feed can be initiated at 10 hours EFT to increase the cell mass. For *Pichia methanolica*, the biomass typically reaches about 30 to about 80, or about 40 to about 60, grams dry cell weight per liter at 48 hours EFT. The glucose feed typically provides a glucose level in the fermentation culture that is less than three grams of glucose per liter, or about one to about two grams of glucose per liter, or even less than one gram of glucose per liter. A "limiting amount of glucose" is considered to be 0.05 grams per liter, or lower than 0.05 grams per liter. Usually, there is little or no expression of the protein of interest during this stage of the incubation if the expression of the protein is controlled by an alcohol-inducible promoter.

As an illustration, a glucose feed can be started at 10 hours EFT and provided at pre-determined rates for 30 hours. At 40 hours EFT, the glucose rate is typically decreased to derepress the methanolic pathway of the yeast cells, and a slow feed of 100% alcohol is initiated. At 48 hours EFT, the glucose feed rate is typically decreased by 50% and the alcohol feed rate is doubled.

This co-feeding rate is maintained until the end of the fermentation (generally, about 70–92 hours EFT). The alcohol can be selected from the group consisting of methanol, ethanol, propanol, isopropanol, butanol, and isobutanol. Typically, the level of alcohol in the fermentation culture is less than one gram of alcohol per liter. Exemplary feeding rates are provided in Table 2 with methanol as the alcohol.

TABLE 2

| Time-FET | 6 liter vessel (grams/hour) | 14 liter vessel (grams/hour) |
| --- | --- | --- |
| Glucose Feed | | |
| 10:00 | 28.0 | 56.0 |
| 18:00 | 37.0 | 74.0 |
| 30:00 | 48.0 | 96.0 |
| 40:00 | 37.0 | 74.0 |
| 48:00 | 28.0 | 56.0 |
| Methanol Feed | | |
| 40:00 | 9.0 | 18.0 |
| 48:00 | 18.0 | 36.0 |

These illustrative feed rates have been optimized for a fermentation running in a 72–96 hour time frame. An average fermentation run for about 70 hours to about 75 hours EFT often produces a dry cell weight of about 75 grams to about 84 grams/liter, although the cell mass can vary between about 50 to about 125 grams/liter. For example, at about 72 hours EFT, the cell mass will typically reach a dry cell weight of about 80 grams/liter. The amount of expressed protein can vary between about 50 to about 350 milligrams of protein per liter of fermentation culture. If the feed rates are too fast to maintain the percentage dissolved oxygen over 15%, then the feed rates should be lowered by 25% and the fermentation run for an additional 24 hours. With full mixing and aeration, the fermentor level will rise and some volume may need to be removed from the fermentor sometime after 50 to 60 hours EFT.

In a variation of the basic method, the fermentation is run for about 40 to about 48 hours EFT as described above. Then, the glucose feed is stopped and the culture is supplemented by the alcohol feed without a co-feeding of glucose.

Surprisingly, it was found that recombinant yeast cell hosts can express a protein of interest when that expression is under the control of an alcohol-inducible promoter, and alcohol is not added to the medium. This is illustrated by Examples 7, and 12, in which the culture medium contained glucose, but not added alcohol. Accordingly, the present invention includes methods for producing polypeptides or peptides by recombinant Pichia, in which the cultured yeast cells are incubated in medium prepared with a sugar, but not alcohol. An illustrative medium consists essentially of water, sugar, inorganic ammonia, potassium, phosphate, iron, biotin, and citric acid, but is not supplemented with an alcohol (e.g., methanol, ethanol, propanol, isopropanol, butanol, and isobutanol). Suitable sugars include glucose, mannose, fructose, and the like. On the other hand, sucrose, lactose, maltose, and glycerol are not preferred carbon sources. Fermentation can be performed as batch, fed-batch, or continuous fermentation methods. These methods can be performed with either alcohol-inducible promoters or constitutive promoters.

The present inventor also discovered that recombinant yeast cell hosts can express a protein of interest when an alcohol is used as the carbon source. This is illustrated by Examples 14 and 15, in which the culture medium contained an alcohol as the carbon source. Accordingly, the present invention includes methods for producing polypeptides or peptides by recombinant Pichia, in which the cultured yeast cells are incubated in medium prepared with an alcohol as the carbon source. An illustrative medium for these methods consists essentially of water, alcohol, inorganic ammonia, potassium, phosphate, iron, biotin, and citric acid. Suitable alcohols include methanol, ethanol, propanol, isopropanol, butanol, isobutanol, and the like. Fermentation such media can be performed as batch, fed-batch, or continuous fermentation methods.

As described in the examples below, the production of the 16 kD protein leptin ("OB") by the methylotrophic yeast *Pichia methanolica* was studied in six liter fed batch fermentations as a model system for protein expression. Efficient expression of leptin has been described using *E. coli* and baculovirus expression systems, but expression in yeast has not been documented (see, for example, Fawzi et al., *Horm. Metab. Res.* 28:694 (1996), Churgay et al., *Gene* 190:131 (1997), and Au et al., *Biochem. Biophys. Res. Commun.* 248:200 (1998)).

In the studies described herein, leptin was produced in *Pichia methanolica* as a secreted protein that was under the control of the methanol-inducible AUG1 promoter, and the leptin included either a FLAG tag (Hopp et al., *Biotechnology* 6:1204 (1988)) or Glu:Glu affinity tag (Grussenmeyer et al., *Proc. Nati. Acad. Sci. USA* 82:7952 (1985)) on the N-terminus of the protein to aid in analysis and purification. Although leptin has been produced in *E. coli* with a FLAG tag, expression using the Glu:Glu tag has not been described. Proteins comprising a Glu:Glu tag were isolated with an antibody affinity column. The activity of recovered leptin was measured by observing the dose-dependent growth response of Baf3 cells to leptin (see, for example, Verploegen et al., *FEBS Lett.* 405:237 (1997); Raver et al., *Protein Expression and Purification* 14:403 (1998)). These cells are recombinant hosts that express a human leptin receptor. The results showed that the human leptin produced by Pichia has the same activity as a standard preparation of human leptin produced by *Saccharomyces cerevisiae*.

5. Isolation of Heterologous Protein From Transformed Pichia

Transformed methylotrophic yeast can be used to produce heterologous polypeptides that are biologically active. Illustrative biologically active polypeptides include Factor VIIa, proinsulin, insulin, follicle stimulating hormone, tissue type plasminogen activator, tumor necrosis factor, interleukin (e.g., interleukin-1 (IL-1), IL-2, IL-3, IL-4, IL-5, IL-6, IL-7, IL-8, IL-9, IL-10, IL-11, IL-12, IL-13, IL-14, IL-15, IL-16, IL-17, and IL-18), colony stimulating factor (e.g., granulocyte-colony stimulating factor (G-CSF) and granulocyte macrophage-colony stimulating factor (GM-CSF)), interferon (e.g., interferons-α, -β, -γ, -ω, -δ, -τ, and -ε), stem cell growth factor designated "S1 factor," erythropoietin, and thrombopoietin. Additional exemplary polypeptides that have been expressed in methylotrophic yeast are discussed above. Those of skill in the art are able to identify further examples of polypeptides suitable for expression.

Moreover, transformed methylotrophic yeast can be used to produced quantities of protein normally synthesized by the yeast host. For example, transformed Pichia can be used to produce quantities of Pichia protein. Illustrative Pichia proteins include alcohol oxidase AUG1 and AUG2, catalase, formaldehyde dehydrogenase, formate dehydrogenase, dihydroxyacetone synthase, dihydroxyacetone kinase, fructose 1,6-bisphosphate aldolase, and fructose 1,6-bisphosphatase.

Typically, secreted proteins are already 30–80% pure, prior to any chromatographic purification steps. Expressed polypeptides can be further purified to at least about 90% purity, to at least about 95% purity, or even greater than 95% purity with respect to contaminating macromolecules, particularly other proteins and nucleic acids, and free of infectious and pyrogenic agents. Polypeptides expressed by methylotrophic yeast may also be purified to a pharmaceutically pure state, which is greater than 99.9% pure.

Methods for isolating recombinant proteins from transformed yeast cells are described, for example, by Ausubel et al. (eds.), *Short Protocols in Molecular Biology, 3rd Edition*, pages 13–49 to 13–61 (John Wiley & Sons, Inc. 1995), and by Romanos et al., "Expression of Cloned Genes in Yeast," in *DNA Cloning* 2: A Practical Approach, 2nd Edition, Glover and Hames (eds.), pages 123–167 (IRL Press, Inc. 1995). More generally, a protein of interest can be isolated from yeast cells using standard techniques, such as affinity chromatography, size exclusion chromatography, ion exchange chromatography, HPLC and the like.

Fractionation and/or conventional purification methods can be used to obtain preparations of heterologous polypeptides expressed by transformed methylotrophic yeast. In general, ammonium sulfate precipitation and acid or chaotrope extraction may be used for fractionation of samples. Exemplary purification steps may include hydroxyapatite, size exclusion, FPLC and reverse-phase high performance liquid chromatography. Suitable chromatographic media include derivatized dextrans, agarose, cellulose, polyacrylamide, specialty silicas, and the like, including PEI, DEAE, QAE, and Q derivatives. Exemplary chromatographic media include those media derivatized with phenyl, butyl, or octyl groups, such as Phenyl-Sepharose FF (Pharmacia), Toyopearl butyl 650 (Toso Haas, Montgomeryville, Pa.), Octyl-Sepharose (Pharmacia) and the like, or polyacrylic resins, such as Amberchrom CG 71 (Toso Haas) and the like. Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of proteins by amino groups, carboxyl groups, sulfhydryl groups, hydroxyl groups and/or carbohydrate moieties.

Examples of coupling chemistries include cyanogen bromide activation, N-hydroxysuccinimide activation, epoxide activation, sulfhydryl activation, hydrazide activation, and carboxyl and amino derivatives for carbodiimide coupling chemistries.

These and other solid media are well known and widely used in the art, and are available from commercial suppliers. Selection of a particular method for polypeptide isolation and purification is a matter of routine design and is determined in part by the properties of the chosen support. See, for example, *Affinity Chromatography: Principles & Methods* (Pharmacia LKB Biotechnology 1988), and Doonan, *Protein Purification Protocols* (The Humana Press 1996).

Additional variations in heterologous polypeptide isolation and purification can be devised by those of skill in the art. For example, antibodies can be used to isolate large quantities of protein by immunoaffinity purification.

It is also possible to engineer a tag onto the amino- or carboxyl-terminus of the recombinant protein to allow purification by affinity chromatography. Examples of commonly used tags include polyHistidine tags (which have an affinity for metal-chelating resin), c-myc tags, calmodulin binding protein (isolated with calmodulin affinity chromatography), substance P, the RYIRS tag (which binds with anti-RYIRS antibodies), maltose-binding protein, an immunoglobulin domain, and the FLAG tag (which binds with anti-FLAG antibodies). See, for example, Luo et al., *Arch. Biochem. Biophys.* 329:215 (1996), Morganti et al., *Biotechnol. Appl. Biochem.* 23:67 (1996), and Zheng et al., *Gene* 186:55 (1997). Nucleic acid molecules encoding such peptide tags are available, for example, from Sigma-Aldrich Corporation (St. Louis, Mo.).

The present invention, thus generally described, will be understood more readily by reference to the following examples, which are provided by way of illustration and are not intended to be limiting of the present invention.

EXAMPLES

To improve yields of recombinantly produced leptin, the feed rates or timing of glucose and methanol feeds were varied to optimize the feeding strategy. The new soluble minimal medium recipe was used in these studies. Moreover, the effects of the addition of typical fermentation growth enhancers, such as yeast extract and casamino acids, were also examined with regard to yield improvements. The fermentation was often initiated in a batch mode on a glucose/ammonium sulfate medium. A mixed feed of glucose/trace metals/ammonium sulfate was started at 10 hours into the run and ramped up for the next 30 hours to produce a high biomass. In certain studies, the glucose rate was decreased or stopped at 40 hours into the fermentation, and a feed of methanol was initiated. Typically, the feed(s) were then delivered for an additional 30 to 40 hours before harvesting the fermentation.

In the following examples, *Pichia methanolica* strain PMAD16 was used as a host strain. This strain is derived from type strain CBS 6515 and is described by Raymond et al., *Yeast* 14:11 (1998), and by Raymond, "Recombinant Protein Expression in *Pichia methanolica*," in *Gene Expression Systems: Using Nature for the Art of Expression*, Fernandez and Hoeffler (eds.), pages 193–209 (Academic Press, Inc. 1999). The host strain carries both alcohol utilization genes AUG1 and AUG2 and is deleted for PEP4 and PRB1 proteases. For these studies, the Pichia contained an expression vector derived from pCZR1 34, which comprises an AUG1 promoter, AUG1 terminator, and ADE2 as a selectable marker (Raymond et al., *Yeast* 14:11 (1998)). A chimeric gene comprising the following elements was inserted between the AUG1 promoter and terminator: a *S. cerevisiae* a-factor prepro sequence, a Glu:Glu tag or a FLAG tag, and a human leptin gene. The human leptin gene has been described by Zhang et al., *Nature* 372:425 (1994). An illustrative method for constructing a plasmid that comprises a human leptin gene is described by Raymond et al., *BioTechniques* 26:134 (1999), and an exemplary human leptin amino acid sequence is provided by SEQ ID NO:7 (GenBank accession No. 4139908).

Example 1

Fed Batch Fermentation without Co-feeding

In this example, *P. methanolica* PMAD16-OBNEE was grown in a fed batch fermentation in a non co-feeding mode.

The fermentation was run in a 6.0 liter vessel with a 3.0 liter starting volume. The fermentation was started in a batch mode on 2.5% glucose using a 250 ml inoculum from a 16 hour shake flask culture grown in YEPD broth (Difco Laboratories, Inc.). The fermentation culture was grown at 30° C. with pH controlled at 5.0 by the addition of 5 N NH$_4$OH. Dissolved oxygen was maintained above 30% through the use of an agitation speed increase/oxygen sparging cascade. At approximately 12 hours into the run, a glucose feed ("feed 1") was initiated and supplied to the fermentor using stepped rate increases for the next 33 hours (45 hours elapsed fermentation time (EFT)). At 38 hours EFT, a slow feed of 100% methanol was introduced to the fermentation culture. The glucose feed was stopped at 45 hours EFT with 1500 grams of glucose feed delivered to the fermentor, and the delivery of methanol was increased. The fermentation was run with methanol feeding for an additional 18 hours (63 hours EFT). A total of 470 grams of 100% methanol was delivered to the vessel. A final dry cell weight of 69.7 grams/liter was obtained. Leptin expression started upon the initiation of methanol dosing and was produced until the fermentation was ended. A leptin yield of 150 milligrams/liter was obtained. See FIG. 1.

Example 2

Fed Batch Fermentation with Co-feeding

Figure 2:
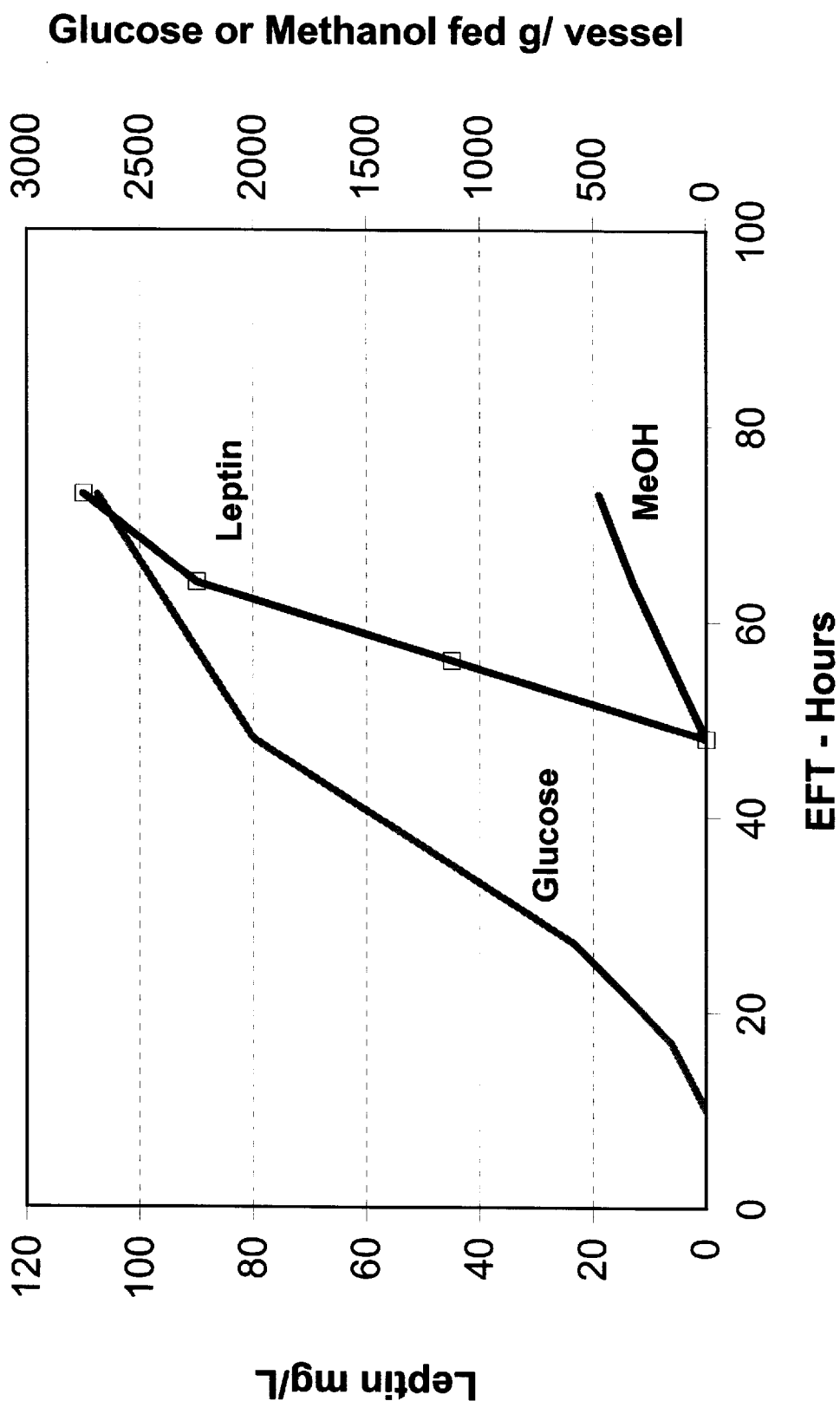
FIG. 2 shows a time course of leptin production by Pichia methanolica in a fed batch fermentation with co-feeding of an alcohol and glucose. "DCW" refers to dry cell weight, while "EFT" refers to elapsed fermentation time.

In this example, *P. methanolica* PMAD16-OBNEE was grown in a fed batch fermentation with glucose-methanol feeding. The fermentation was started in a batch mode on 2.5% glucose using a 250 ml inoculum from a 16 hour shake flask culture grown in YEPD broth (Difco). The fermentation was run in a 6.0 liter vessel with a 3.0 liter starting volume. The fermentation was performed at 30° C. with pH controlled at 5.0 by the addition of 5 N NH$_4$OH. Dissolved oxygen was maintained above 30% through the use of an agitation speed increase/oxygen sparging cascade. At 10 hours into the run, a glucose feed ("feed 1") was initiated and supplied to the fermentor using stepped rate increases for the next 18 hours (28 hours EFT). The glucose feed rate was then held constant for the next 20 hours. At 48 EFT hours, the glucose feed rate was lowered by 50% and the methanol feed was started. A total of 475 grams of 100% methanol and 2690 grams of feed 1 were delivered to the vessel. Leptin expression started upon the initiation of methanol dosing and was produced until the fermentation was ended at 78 hours EFT. A leptin yield of 110 milligrams/liter was obtained. See FIG. 2.

Example 3

Fed Batch Fermentation with Co-feeding and Additional Nitrogen

Figure 3:
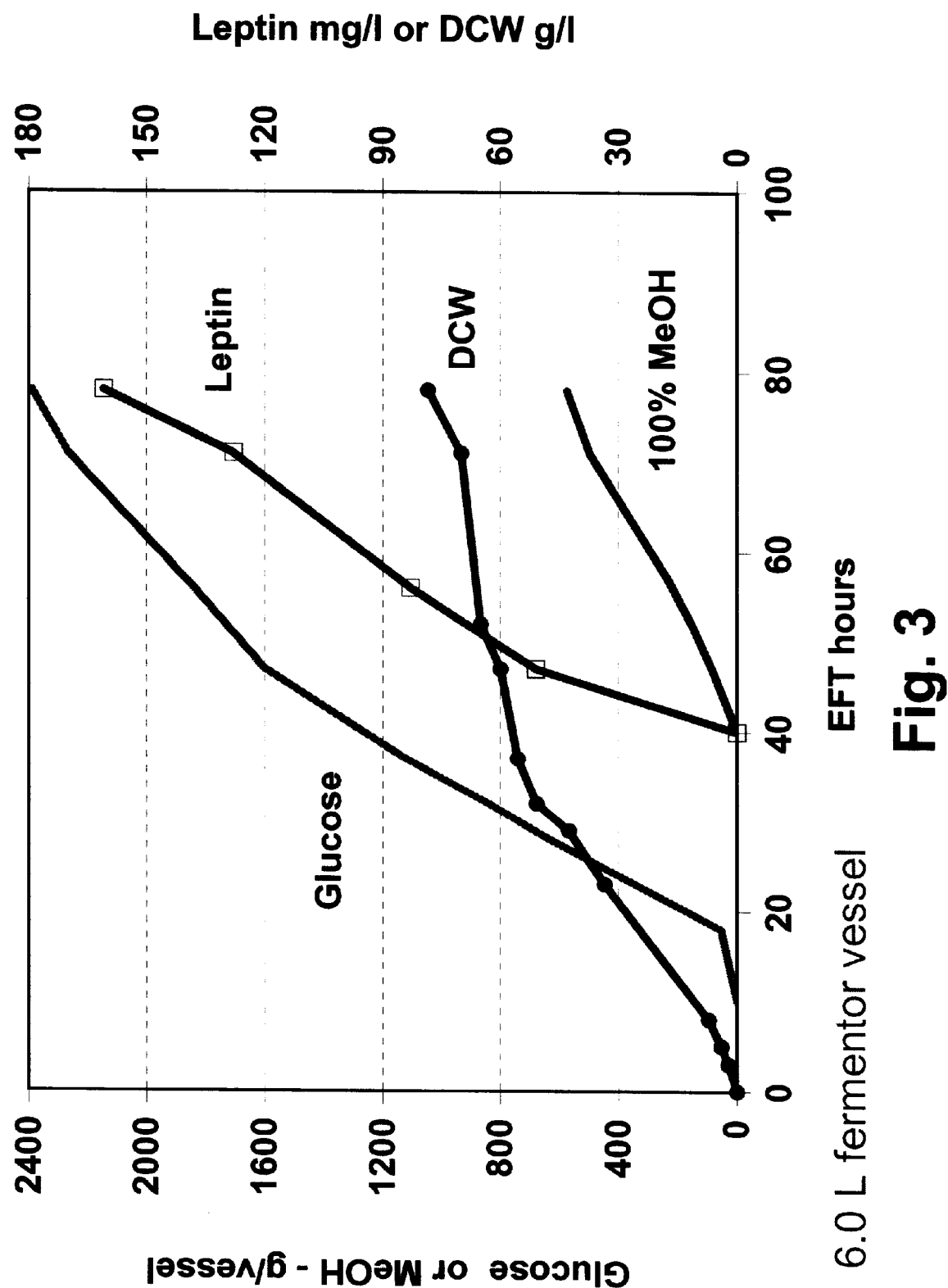
FIG. 3 shows a time course of leptin production by Pichia methanolica in a fed batch fermentation with co-feeding and additional nitrogen. "DCW" refers to dry cell weight, while "EFT" refers to elapsed fermentation time.

In this example, *P. methanolica* PMADI6-OBNEE was grown in a fed batch fermentation in a glucose methanol co-feeding mode. The fermentation was started in a batch mode on 2.5% glucose using a 250 ml inoculum from a 16 hour shake flask culture grown in YEPD broth (Difco). The illustrative minimal medium was supplemented with additional nitrogen by adding casamino acids (5.0 grams/liter) and ammonium sulfate (10.0 grams/liter). The fermentation was run in a 6.0 liter vessel with a 3.0 liter starting volume. The fermentation was performed at 30° C. with pH controlled at 4.0 by the addition of 5 N NH$_4$OH. Dissolved oxygen was maintained above 30% through the use of an agitation speed increase/oxygen sparging cascade. At approximately 10 hours into the run, a glucose feed ("feed 1") was initiated and supplied to the fermentor using stepped rate increases for the next 30 hours (40 hours EFT). At 40 hours EFT, a slow feed of 100% methanol was introduced to the fermentation culture. At 48 EFT hours, the glucose feed rate was lowered by 50% and the methanol feed rate was doubled for the remainder of the run, which ended at 71 hours EFT. A total of 575 grams of 100% methanol and 2400 grams of feed 1 were delivered to the vessel. Leptin expression started upon the initiation of methanol dosing and was produced until the fermentation was ended. A leptin yield of 150 milligrams/liter was obtained. See FIG. 3.

Example 4

Fed Batch Fermentation with Slower Glucose Feed

Figure 4:
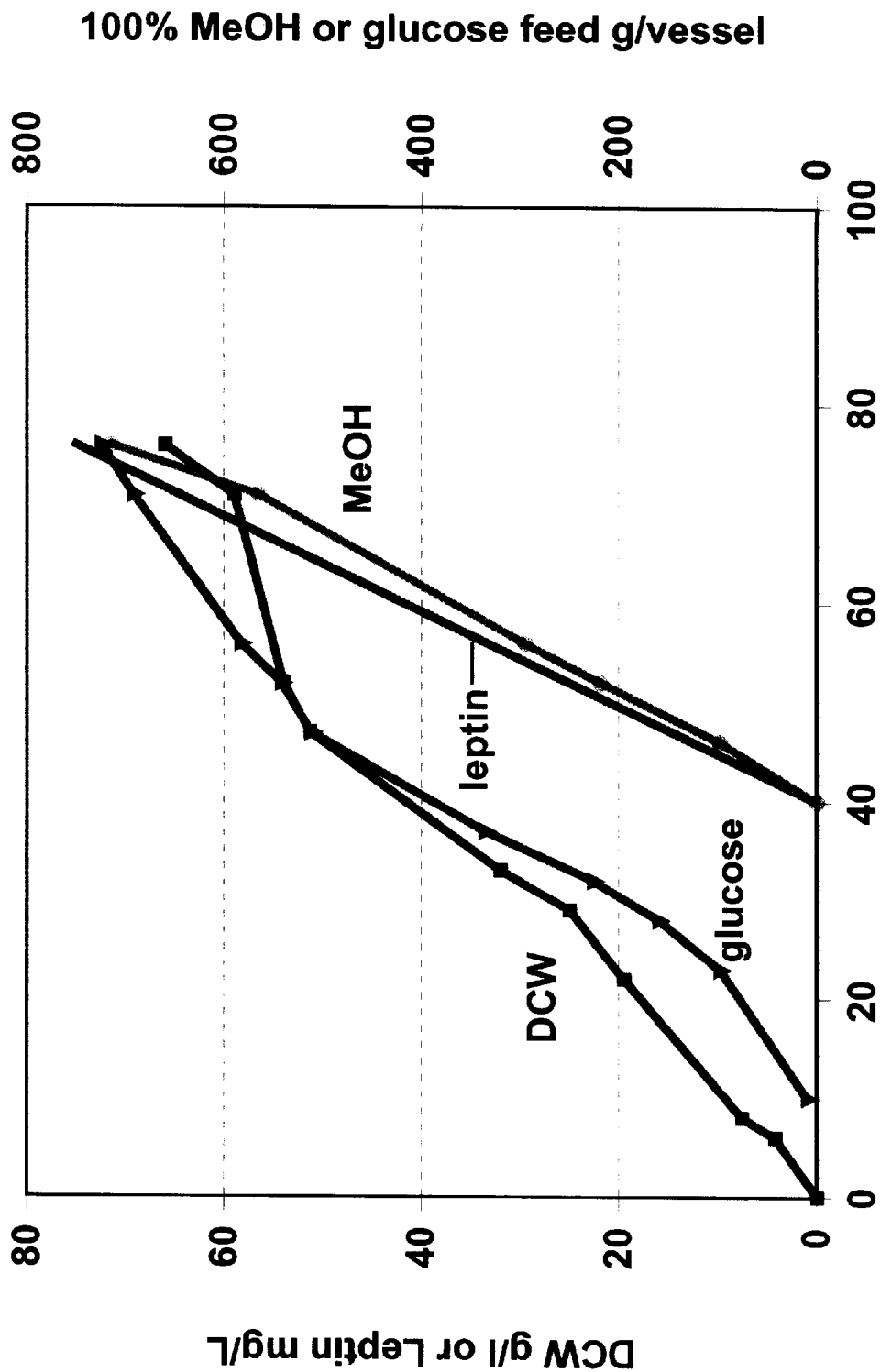
FIG. 4 shows a time course of leptin production by Pichia methanolica in a fed batch fermentation with slower glucose feed. "DCW" refers to dry cell weight, while "EFT" refers to elapsed fermentation time.

In this example, *P. methanolica* PMAD16-OBNEE was grown in a fed batch fermentation with glucose-methanol co-feeding and a decreased glucose feed rate. The fermentation was started in a batch mode on 2.5% glucose using a 250 ml inoculum from a 16 hour shake flask culture grown in YEPD broth (Difco). The illustrative minimal medium was supplemented with 10.0 grams/liter anunonium sulfate. The fermentation was run in a 6.0 liter vessel with a 3.0 liter starting volume. The fermentation was performed at 30° C. with pH controlled at 4.0 by the addition of 5 N NH$_4$OH. Dissolved oxygen was maintained above 30% through the use of an agitation speed increase/oxygen sparging cascade. At approximately 10 hours into the run, a glucose feed ("feed 1") was initiated and supplied to the fermentor using stepped rate increases for the next 30 hours (40 hours EFT). At 40 hours EFT, a slow feed of 100% methanol was introduced to the fermentation culture. At 48 EFT hours, the glucose feed rate was lowered and the methanol feed rate was slightly increased for the remainder of the run. A total of 714 grams of 100% methanol and 1350 grams of feed 1 were delivered to the vessel. Leptin expression started upon the initiation of methanol dosing and was produced until the fermentation was ended The fermentation ended at 66 hours EFT. A leptin yield of 75 milligrams/liter was obtained. The ratio of glucose (53% w/v) to methanol (100%) fed was 1:1. See FIG. 4.

Example 5

Fed Batch Fermentation with Co-feeding and Additional Glucose

Figure 5:
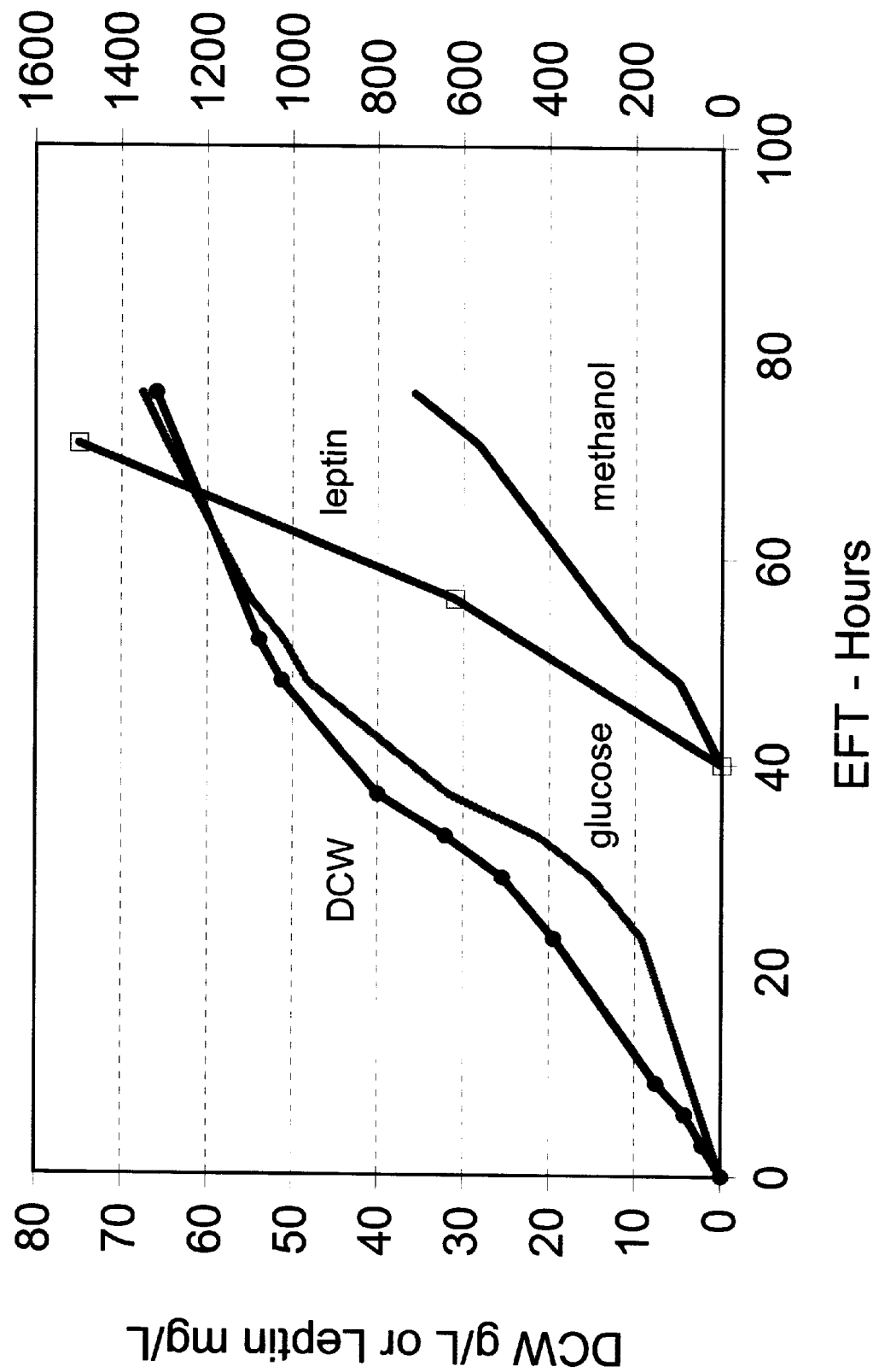
FIG. 5 shows a time course of leptin production by Pichia methanolica in a fed batch fermentation with co-feeding and additional glucose. "DCW" refers to dry cell weight, while "EFT" refers to elapsed fermentation time.

In this example, *P. methanolica* PMAD16-OBNEE was grown in a fed batch fermentation in a glucose-methanol co-feeding mode. The fermentation was started in a batch mode on 2.5% glucose using a 250 ml inoculum from a 16 hour shake flask culture grown in YEPD broth (Difco). The illustrative minimal medium was supplemented with additional nitrogen by adding ammonium sulfate (10.0 grains/liter). The fermentation was run in a 6.0 liter vessel with a 3.0 liter starting volume. The fermentation was performed at 30° C. with pH controlled at 4.0 by the addition of 5 N NH$_4$OH. Dissolved oxygen was maintained above 30% through the use of an agitation speed increase/oxygen sparging cascade. At 8 hours into the run, a glucose feed ("feed 1") was initiated and supplied to the fermentor. The feed rate was doubled at 18 hours and reduced by 50% at 30 hours EFT. At 48 hours EFT, a slow feed of 100% methanol was introduced to the fermentation culture and the glucose feed rate was lowered by 50%. A total of 635 grams of 100% methanol and 2525 grams of feed 1 were delivered to the vessel. The fermentation ended at 71 hours EFT. Leptin expression started upon the initiation of methanol dosing and was produced until the fermentation was ended. A leptin yield of 90 milligrams/liter was obtained. See FIG. 5.

Example 6

Fed Batch Fermentation with Glucose and Ethanol Co-feeding

Figure 6:
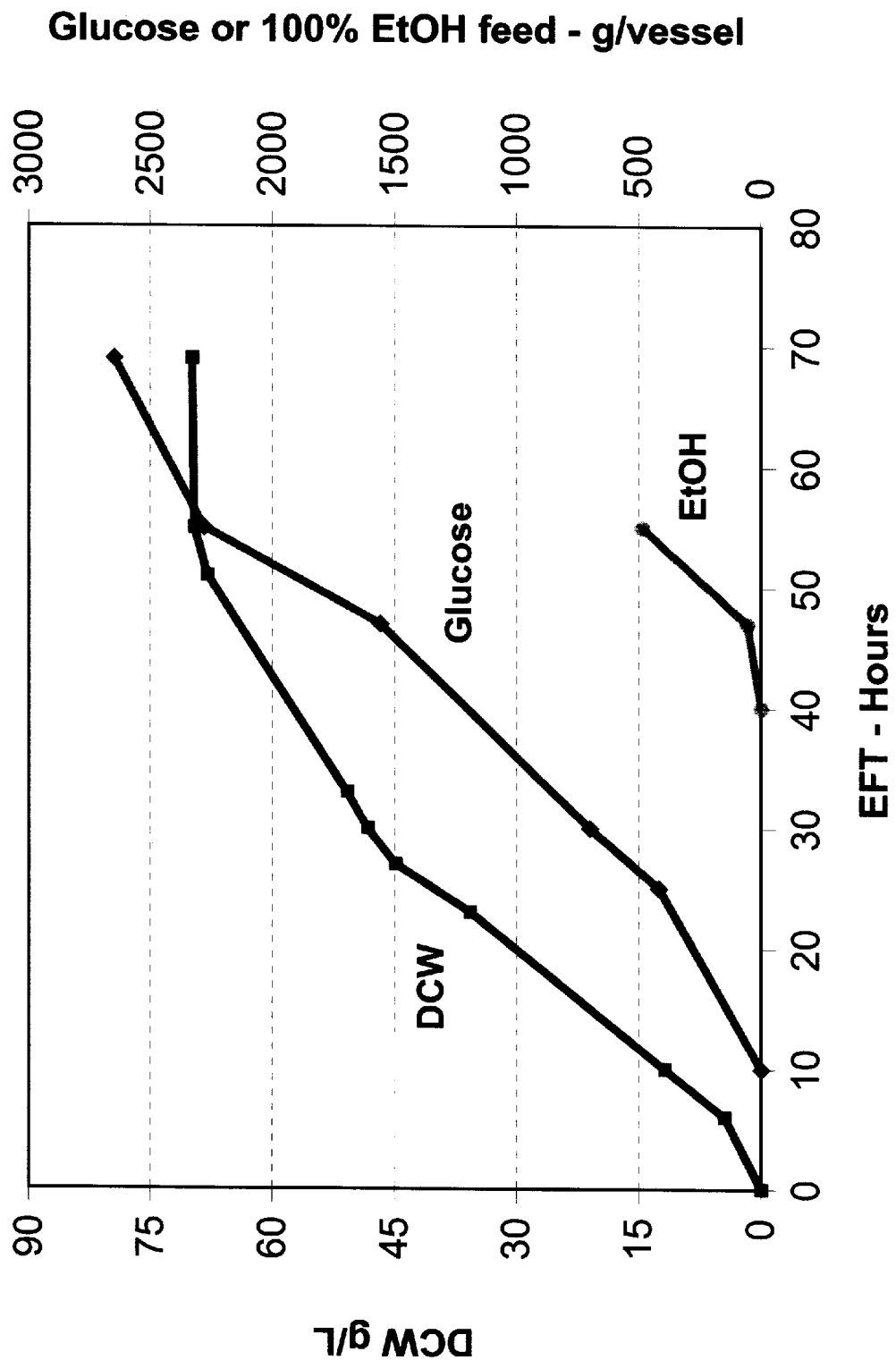
FIG. 6 shows a time course of Pichia methanolica fermentation with glucose and ethanol co-feeding. "DCW" refers to dry cell weight, while "EFT" refers to elapsed fermentation time.

P. methanolica PMAD16-OBNEE was grown in a fed batch fermentation in a glucose-ethanol co-feeding mode. The fermentation was started in a batch mode on 2.5% glucose using a 250 ml inoculum from a 16 hour shake flask culture grown in YEPD broth (Difco). The illustrative minimal medium, described above, was supplemented with additional nitrogen by adding ammonium sulfate to 21.5 grams/liter. The fermentation was run in a 6.0 liter vessel with a 3.0 liter starting volume. Fermentation was performed at 30° C. with pH controlled at 4.0 by the addition of 5 N $NH_4OH$. Dissolved oxygen was maintained above 30% though the use of an agitation speed increase/oxygen sparging cascade. At approximately 10 hours elapsed fermentation time, a glucose feed ("feed 1") was initiated and supplied to the fermentor using stepped rate increases for the next 30 hours (40 hours EFT). At 40 hours EFT, a slow feed of 100% ethanol was introduced to the fermentation culture. At 48 hours EFT, the glucose feed rate was lowered by 50%, and the ethanol feed rate was doubled for the remainder of the run. A total of 500 grams of 100% ethanol and 2600 grams of feed 1 were delivered to the vessel. Leptin expression started upon the initiation of ethanol dosing and was produced until the fermentation was ended. See FIG. 6.

Example 7

Figure 7:
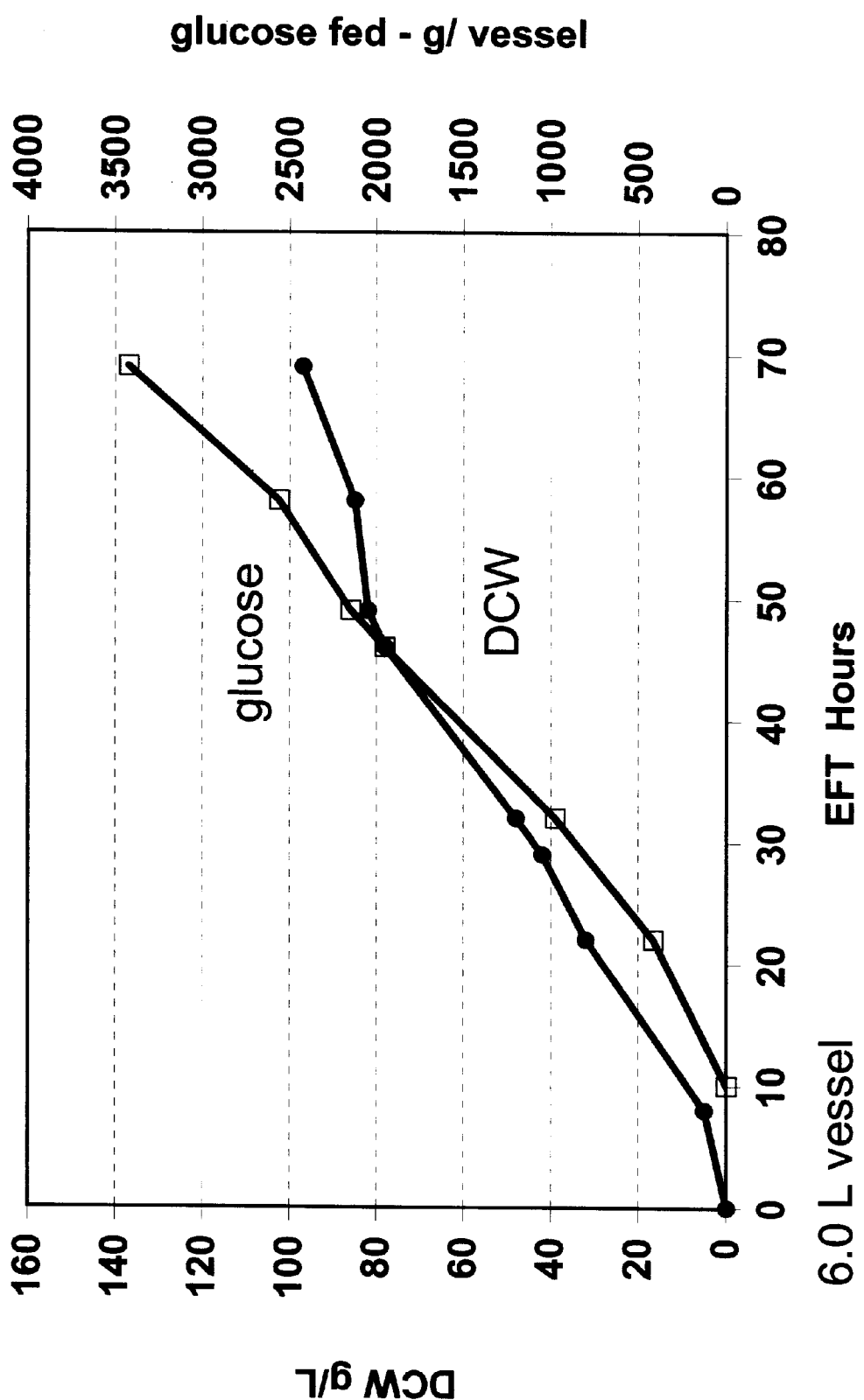
FIG. 7 shows a time course of Pichia methanolica fermentation with glucose feeding in the absence of an alcohol feeding. "DCW" refers to dry cell weight, while "EFT" refers to elapsed fermentation time.

Fed Batch Fermentation with Glucose Feeding in the Absence of an Alcohol Feeding P. methanolica PMAD16-OBNEE was grown in a fed batch fermentation in a glucose only feeding mode. The fermentation was started in a batch mode on 2.5% glucose using a 250 ml inoculum from a 16 hour shake flask culture grown in YEPD broth (Difco). The illustrative minimal medium, described above, was supplemented with additional nitrogen by adding ammonium sulfate to 21.5 grams/liter. The fermentation was run in a 6.0 liter vessel with a 3.0 liter starting volume. The fermentation was performed at 30° C. with pH controlled at 4.5 though the addition of 5 N $NH_4OH$. Dissolved oxygen was maintained above 30% though the use of an agitation speed increase/oxygen sparging cascade. At 10 hours elapsed fermentation time, a glucose feed was initiated. The feed rate was doubled at 28 hours into the run and increased again at 40 hours EFT to the final feed rate of 42.5 grams glucose feed/hour/vessel. This feed rate was maintained until the end of the fermentation at 70 hours. Leptin expression was detected at an EFT of 28 hours and increased as the fermentation progressed and biomass was increased. See FIG. 7.

Example 8

Figure 8:
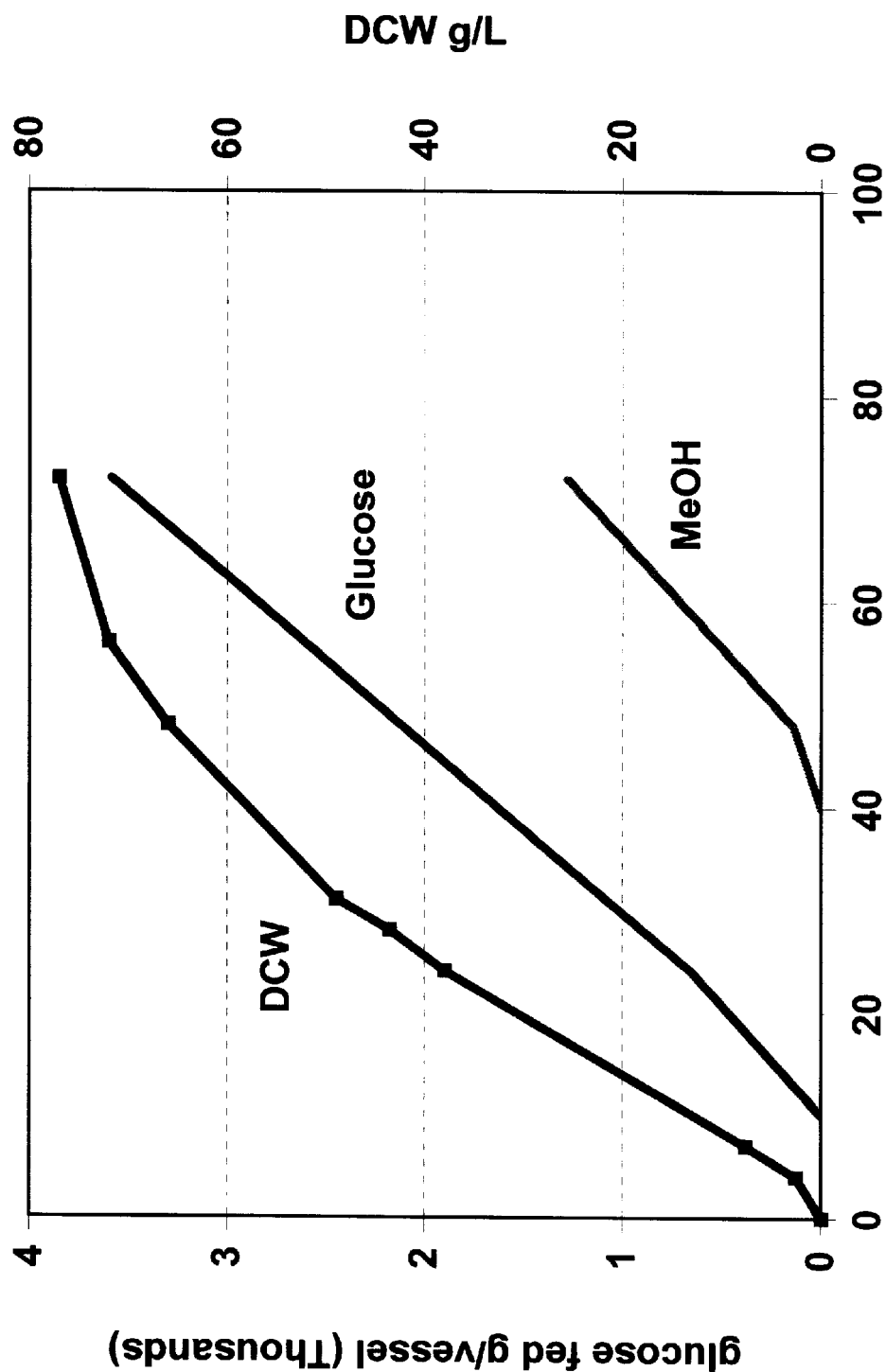
FIG. 8 shows a time course of *Pichia methanolica* fermentation with increased methanol feeding and lowered glucose feeding. "DCW" refers to dry cell weight, while "EFT" refers to elapsed fermentation time.

Fed Batch Fermentation with Increased Methanol Feeding and Lowered Glucose Feeding P. methanolica PMAD16-OBNEE was grown in a fed batch fermentation in a glucose—methanol co-feeding mode. The fermentation was started in a batch mode on 2.5% glucose using a 250 ml inoculum from a 16 hour shake flask culture grown in YEPD broth (Difco). The fermentation was run in a 14.0 liter vessel with a 6.0 liter starting volume, using the illustrative minimal medium, described above. The fermentation was performed at 30° C. with pH controlled at 4.5 though the addition of 5 N $NH_4OH$. Dissolved oxygen was maintained above 30% though the use of an agitation speed increase/oxygen sparging cascade. At 10 hours elapsed fermentation time, a glucose feed was initiated and supplied to the fermentor using stepped rate increases for the next 30 hours (40 hours EFT). At 40 hours EFT, a slow feed of 100% methanol was introduced to the fermentation culture. At 48 hours EFT, the glucose feed rate was lowered by 75% and the ethanol feed rate was tripled for the remainder of the run. A total of 1275 grams of 100% methanol and 3585 grams of glucose feed were delivered to the vessel. The ratio of glucose (53%) to methanol (100%) fed was 1.5:1. The normal glucose:methanol ratio was 2.75. Leptin expression started upon the initiation of methanol dosing and was produced until the fermentation was ended. The final biomass was 76.9 grams dry cell weight/liter. See FIG. 8.

Example 9

Fed Batch Fermentation with a Low Salt Medium

P. methanolica PMAD16-OBNEE was grown in a fed batch fermentation in a glucose—methanol co-feeding mode. The fermentation was started in a batch mode on 2.5% glucose, but with a starting minimal medium ("solution 1") recipe that contained half of the salt concentrations, as described in Table 1. The fermentation was run in a 6.0 liter vessel with a 3.0 liter starting volume. The fermentation was performed at 30° C. with pH controlled at 4.5 though the addition of 5 N $NH_4OH$. Dissolved oxygen was maintained above 30% though the use of an agitation speed increase/oxygen sparging cascade. At approximately 10 hours into the run, a glucose feed ("feed 1") was initiated and supplied to the fermentor using stepped rate increases for the next 30 hours (40 hours EFT). At 40 hours EFT, a slow feed of 100% methanol was introduced to the fermentation culture. At 48 hours EFT, the glucose feed rate was lowered by 50% and the ethanol feed rate was doubled for the remainder of the run. A total of 550 grams of 100% methanol and 2400 grams of feed 1 were delivered to the vessel. Leptin expression started upon the initiation of methanol dosing and was produced until the fermentation was ended. The final dry cell weight was 79.95 g/L.

Example 10

Fed Batch Fermentation with a High Salt Medium

P. methanolica PMAD16-OBNEE was grown in a fed batch fermentation in a glucose—methanol co-feeding mode. The fermentation was started in a batch mode on 2.5% glucose, but with a starting minimal medium ("solution 1") recipe that contained 50% higher concentrations of salt, as described in Table 1. The fermentation was run in a 6.0 liter vessel with a 3.0 liter starting volume. The fermentation was performed at 30° C. with pH controlled at 4.5 though the addition of 5 N $NH_4OH$. Dissolved oxygen was maintained above 30% though the use of an agitation speed increase/oxygen sparging cascade. At approximately 10 hours into the run, a glucose feed ("feed 1") was initiated and supplied to the fermentor using stepped rate increases for the next 30 hours (40 hours EFT). At 40 hours EFT, a slow feed of 100% methanol was introduced to the fermentation culture. At 48 hours EFT, the glucose feed rate was lowered by 50% and the ethanol feed rate was doubled for the remainder of the run. A total of 575 grams of 100% methanol and 2200 grams of feed 1 were delivered to the vessel. Leptin expression started upon the initiation of methanol dosing and was produced until the fermentation was ended. The final dry cell weight of the biomass was 90.58 g/L in a 76 hour ferment.

Example 11

Fed Batch Fermentation with a Glucose Feed that Lacked Trace Metals

*P. methanolica* PMAD16-OBNEE was grown in a fed batch fermentation in a glucose—methanol co-feeding mode. The fermentation was started in a batch mode on 2.5% glucose with the illustrative minimal medium. The fermentation was run in a 6.0 liter vessel with a 3.0 liter starting volume. The fermentation was performed at 30° C. with pH controlled at 4.5 though the addition of 5 N $NH_4OH$. Dissolved oxygen was maintained above 30% though the use of an agitation speed increase/oxygen sparging cascade. At approximately 10 hours into the run, a glucose feed ("feed 1") was initiated and supplied to the fermentor using stepped rate increases for the next 30 hours (40 hours EFT). This feed was different from the glucose feeds described above, in that the trace metals, magnesium sulfate and ammonium sulfate additions were omitted. The feed received only the normal vitamin solution (2 ml/L feed) and enough water to lower the glucose concentration to about 53% w/v. At 40 hours EFT, a slow feed of 100% methanol was introduced to the fermentation culture. At 48 hours EFT, the glucose feed rate was lowered by 50% and the ethanol feed rate was doubled for the remainder of the run. A total of 500 grams of 100% methanol and 2600 grams of feed 1 were delivered to the vessel. Leptin expression started upon the initiation of methanol dosing and was produced until the fermentation was ended. The glucose:methanol ratio was 2.75. The final dry cell weight of the biomass was 79.31 g/L.

Example 12

Fed Batch Fermentation with Only Glucose Feeding

In this example, leptin expression was under the control of an AUG1 promoter. *P. methanolica* PMAD16-OBNEE-AUG1 was grown in a fed batch fermentation in a glucose only feeding mode. The fermentation was started in a batch mode on 2.5% glucose using a 250 ml inoculum from a 16 hour shake flask culture grown in YEPD broth (Difco). The illustrative minimal medium was supplemented with additional nitrogen by adding ammonium sulfate (10.0 g/L). The fermentation was run in a 6.0 liter vessel with a 3.0 liter starting volume. The fermentation was performed at 30° C. with pH controlled at 4.5 though the addition of 5 N $NH_4OH$. Dissolved oxygen was maintained above 30% though the use of an agitation speed increase/oxygen sparging cascade. At 10 hours into the run, a glucose feed was initiated. The feed rate was doubled at 28 hours into the run and increased again at 40 hours EFT to the final feed rate of 42.5 grams glucose feed/hour/vessel. This feed rate was maintained until the end of the fermentation at 70 hours. Leptin expression was detected at an EFT of 28 hours and increased during as the fermentation progressed and biomass was increased.

Example 13

Fed Batch Fermentation With Glucose-Ethanol Co-Feeding

*P. methanolica* PMAD16-OBNEE-AUG1 was grown in a fed batch fermentation in a glucose-ethanol co-feeding mode. The fermentation was started in a batch mode on 2.5% glucose, using a 250 ml inoculum from a 16 hour shake flask culture grown in YEPD broth (Difco). The basal fermentation recipe was supplemented with additional nitrogen by adding ammonium sulfate (10.0 g/L). The fermentation was run in a 6.0 liter vessel with a 3.0 liter starting volume. The fermentation was performed at 30° C. with pH controlled at 4.0 though the addition of 5 N $NH_4OH$. Dissolved oxygen was maintained above 30% though the use of an agitation speed increase/oxygen sparging cascade. At approximately 10 hours into the run, a glucose feed (feed 1) was initiated and supplied to the fermentor using stepped rate increases for the next 30 hours (40 hours EFT). At 40 hours EFT, a slow feed of 100% ethanol was introduced to the ethanol feed rate was doubled for the remainder of the run. A total of 500 grams of 100% ethanol and 2600 grams of feed 1 were delivered to the vessel. Leptin expression started upon the initiation of ethanol dosing, and leptin was produced until the fermentation was ended.

Example 14

Semi-Fed Batch Fermentation with Methanol as Carbon Source

In this example, *P. methanolica* PMAD16-pGNIN1-AUG was grown in a batch fermentation with methanol as the carbon source. Here, the expression of a test protein was under the control of an AUG promoter. The basal recipe contained 200 mM citrate phosphate buffer for pH maintenance, 1.35% yeast nitrogen base, 0.1% yeast extract, and 2% methanol at the start. The fermentation was run in a batch mode using a 250 ml inoculum from a 16 hour shake flask culture grown in YEPD broth (Difco). The fermentation was run in a 14.0 liter vessel with a 10.0 liter starting volume and was performed at 30° C. At 24 hours elapsed fermentation time, the culture was fed with 10 ml/liter of 100% methanol. This was repeated again at 40 hours. The fermentation was harvested at 48 hours. Western blot analysis showed the production of the test protein was approximately 2 mg/L.

Example 15

Continuous Culture with Methanol as Carbon Source

*P. methanolica* PMAD16-pVRM13-AUGI was grown in continuous culture for production of a test protein under the control of an AUG1 promoter. The fermentation was started in a batch mode on 1.0% methanol using a 60 ml inoculum from a 16–20 hour shake flask culture grown in YEPD broth (Difco). The fermentation was run in a 1.50 liter vessel with a 1.25 liter starting volume. The fermentation was performed at 30° C. with pH controlled at 5.5 though the addition of 100 mM citrate phosphate buffer to the illustrative minimal medium. Dissolved oxygen was maintained above 30% though the use of an agitation speed increase/oxygen sparging cascade. At 10 hours into the run, a 1% methanol salts feed was initiated at a dilution rate of $0.0650^{h-1}$. The methanol feed rate was increased to $D=0.10^{h-1}$ at 80 hours EFT. The methanol concentration in the feed was changed to 2% at 150 hours EFT, while the dilution rate was maintained at $D=0.10^{h-1}$. Test protein expression was detected at an EFT of 23 hours and increased when the methanol feed was increased to 2% methanol.

Example 16

Fed Batch Fermentation with Glucose

In this example, *P. methanolica* PMADI 6-OBNEE-GAP was grown in a fed batch fermentation in a glucose only feeding mode. Here, leptin gene expression was regulated by a GAP promoter. The fermentation was started in a batch mode on 2–5% glucose using a 250 ml inoculum from a 16 hour shake flask culture grown in YEPD broth (Difco). The fermentation was run in a 6.0 liter vessel with a 3.0 liter starting volume. The fermentation was performed at 30° C. with pH controlled at 4.5 though the addition of 5 N NH$_4$OH. Dissolved oxygen was maintained above 30% though the use of an agitation speed increase/oxygen sparging cascade. At 10 hours into the run, a glucose feed was initiated. The feed rate was increased by 50% at 18 hours, 30 hours, and 40 hours EFT to the final feed rate of 42.5 grams glucose feed/hour/vessel. This feed rate was maintained until the end of the fermentation at 70 hours. Leptin expression was detected at an EFT of 14 hours and increased throughout the run.

Example 17

Variation of Fed Batch Fermentation with Glucose

*P. methanolica* PMAD16-pCZR249-GAP was grown in a fed batch fermentation in a glucose only feeding mode to observe the production of a test protein controlled by a GAP promoter. The fermentation was started in a batch mode on 2.5% glucose using a 250 ml inoculum from a 16 hour shake flask culture grown in YEPD broth (Difco). The fermentation was run in a 6.0 liter vessel with a 3.0 liter starting volume. The fermentation was performed at 30° C. with pH controlled at 4.5 though the addition of 5 N NH$_4$OH. Dissolved oxygen was maintained above 30% though the use of an agitation speed increase/oxygen sparging cascade. At 10 hours into the run a glucose feed was initiated. The feed rate was increased by 50% at 18 hours, 30 hours and 40 hours EFT to the final feed rate of 42.5 grams glucose feed/hour/vessel. This feed rate was maintained until the end of the fermentation at 72 hours. Test protein expression was detected at an EFT of 32 hours and increased throughout the run. Production of test protein, as determined by western blot analysis, was 80 mg/L.

Example 18

Fed Batch Fermentation with Fructose

*P. methanolica* PMAD16-pCZR249-GAP was grown in a fed batch fermentation in a fructose only feeding mode. The fermentation was started in a batch mode on 2.5% fructose using a 250 ml inoculum from a 16 hour shake flask culture grown in YEPD broth (Difco). The fermentation was run in a 6.0 liter vessel with a 3.0 liter starting volume. The fermentation was performed at 30° C. with pH controlled at 4.5 though the addition of 5 N NH$_4$OH. Dissolved oxygen was maintained above 30% though the use of and agitation speed increase/oxygen sparging cascade. At 10 hours into the run a fructose feed was initiated. The feed rate was increased by 50% at 18 hours, 30 hours, and 40 hours EFT to the final feed rate of 42.5 grams glucose feed/hour/vessel. This feed rate was maintained until the end of the fermentation at 72 hours. Test protein expression was detected at an EFT of 32 hours, and increased throughout the run. Production of the test protein, as determined by western blot analysis, was 80 mg/L.

Example 19

Continuous Culture Fermentation with Glucose

In this example, *P. methanolica* PMAD16-OBNEE-GAP was grown in a continuous culture fermentation in a glucose only feeding mode. The fermentation was started in a batch mode on 2.0% glucose using a 60 ml inoculum from a 16 hour shake flask culture grown in YEPD broth (Difco). The fermentation was run in a 1.50 liter vessel with a 1.25 liter starting volume. The fermentation was performed at 30° C. with pH controlled at 4.5 though the addition of 5 N NH$_4$OH. Dissolved oxygen was maintained above 30% though the use of an agitation speed increase/oxygen sparging cascade. At 10 hours into the run a 2% glucose salts feed was initiated at a dilution rate of $0.10^{h-1}$. The glucose feed was increased to 4% at 80 hours EFT, while the dilution rate was kept at $D=0.10^{h-1}$. Leptin expression was detected at an EFT of 22 hours and increased when the glucose feed was increased to 4% glucose. From the foregoing, it will be appreciated that, although specific embodiments of the invention have been described herein for purposes of illustration, various modifications may be made without deviating from the spirit and scope of the invention. Accordingly, the invention is not limited except as by the appended claims.

I claim:

1. A method for producing a peptide or polypeptide by a recombinant *Pichia methanolica* host, comprising the step of incubating the recombinant *Pichia methanolica* host in a medium to produce a *Pichia methanolica* culture, wherein the cultured *Pichia methanolica* express the peptide or polypeptide under the control of an alcohol-inducible promoter, wherein the medium comprises sugar but is not supplemented with alcohol, and wherein the incubated *Pichia methanolica* produce the peptide or polypeptide.

2. The method of claim 1, wherein the medium is a minimal medium.

3. The method of claim 2, wherein the minimal medium consists essentially of water, sugar, inorganic ammonia, potassium, phosphate, iron, biotin, and citric acid.

4. The method of claim 1, wherein the medium is a rich medium.

5. The method of claim 1, wherein the sugar is selected from the group consisting of glucose, fructose, and mannose.

6. The method of claim 5, wherein the sugar is fructose.

7. The method of claim 5, wherein the sugar is mannose.

8. The method of claim 5, wherein the sugar is glucose.

9. The method of claim 8, wherein the medium is a minimal medium.

10. The method of claim 8, wherein the alcohol-inducible promoter is a methanol-inducible promoter.

11. The method of claim 10, wherein the medium is a minimal medium.

12. The method of claim 11, further comprising the step of isolating the peptide or polypeptide either from the culture medium, or from the cultured Pichia host.

13. The method of claim 8, further comprising the step of isolating the peptide or polypeptide either from the culture medium, or from the cultured Pichia host.

14. The method of claim 10, wherein the methanol-inducible promoter is a *Pichia methanolica* AUG1 promoter.

15. The method of claim 10, further comprising the step of isolating the peptide or polypeptide either from the culture medium, or from the cultured Pichia host.

16. The method of claim 1, wherein the alcohol-inducible promoter is a methanol-inducible promoter.

17. The method of claim 16, wherein the medium is a minimal medium.

18. The method of claim 16, wherein the methanol-inducible promoter is a *Pichia methanolica* AUG1 promoter.

19. The method of claim 18, further comprising the step of isolating the peptide or polypeptide either from the culture medium, or from the cultured Pichia host.

20. The method of claim 1, wherein incubation is performed by batch fermentation.

21. The method of claim 1, wherein incubation is performed by fed-batch fermentation.

22. The method of claim 21, wherein the medium is a minimal medium.

23. The method of claim 1, wherein incubation is performed by continuous fermentation.

24. A method for producing a peptide or polypeptide by a recombinant *Pichia methanolica* host, comprising the step of incubating the recombinant *Pichia methanolica* host in a medium to produce a *Pichia methanolica* culture, wherein the cultured *Pichia methanolica* express the peptide or polypeptide under the control of a methanol-inducible promoter, wherein the medium comprises sugar but is not supplemented with alcohol, wherein the sugar is selected from the group consisting of glucose, fructose, and mannose, wherein the incubated *Pichia methanolica* produce the peptide or polypeptide, and wherein the incubation step is performed by fed batch fermentation.

25. The method of claim 24, wherein the medium is a minimal medium.

26. The method of claim 25, wherein the minimal medium consists essentially of water, sugar, inorganic ammonia, potassium, phosphate, iron, biotin, and citric acid.

27. The method of claim 25, further comprising the step of isolating the peptide or polypeptide either from the culture medium, or from the cultured Pichia host.

28. The method of claim 24, wherein the methanol-inducible promoter is a *Pichia methanolica* AUG1 promoter.

29. The method of claim 28, wherein the medium is a minimal medium.

30. The method of claim 29, further comprising the step of isolating the peptide or polypeptide either from the culture medium, or from the cultured Pichia host.

31. The method of claim 28, further comprising the step of isolating the peptide or polypeptide either from the culture medium, or from the cultured Pichia host.

32. The method of claim 24, further comprising the step of isolating the peptide or polypeptide either from the culture medium, or from the cultured Pichia host.

33. A method for producing a peptide or polypeptide by a recombinant *Pichia methanolica* host, comprising the step of incubating the recombinant *Pichia methanolica* host in a medium to produce a *Pichia methanolica* culture, wherein the cultured *Pichia methanolica* express the peptide or polypeptide under the control of a methanol-inducible promoter, wherein the medium comprises glucose but is not supplemented with alcohol, wherein the incubated *Pichia methanolica* produce the peptide or polypeptide, and wherein the incubation step is performed by fed batch fermentation.

34. The method of claim 33, wherein the medium is a minimal medium.

35. The method of claim 34, wherein the minimal medium consists essentially of water, sugar, inorganic ammonia, potassium, phosphate, iron, biotin, and citric acid.

36. The method of claim 34, further comprising the step of isolating the peptide or polypeptide either from the culture medium, or from the cultured Pichia host.

37. The method of claim 33, wherein the methanol-inducible promoter is a *Pichia methanolica* AUG1 promoter.

38. The method of claim 37, wherein the medium is a minimal medium.

39. The method of claim 38, further comprising the step of isolating the peptide or polypeptide either from the culture medium, or from the cultured Pichia host.

40. The method of claim 37, further comprising the step of isolating the peptide or polypeptide either from the culture medium, or from the cultured Pichia host.

41. The method of claim 33, further comprising the step of isolating the peptide or polypeptide either from the culture medium, or from the cultured Pichia host.

* * * * *

SEQUENCE LISTING

<160> NUMBER OF SEQ ID NOS: 11

<210> SEQ ID NO 1
<211> LENGTH: 3077
<212> TYPE: DNA
<213> ORGANISM: Pichia methanolica

<400> SEQUENCE: 1

```
cagctgctct gctccttgat tcgtaattaa tgttatcctt ttactttgaa ctcttgtcgg      60
tccccaacag ggattccaat cggtgctcag cgggatttcc catgaggttt ttgacaactt     120
tattgatgct gcaaaaactt ttttagccgg gtttaagtaa ctgggcaata tttccaaagg     180
ctgtgggcgt tccacactcc ttgcttttca taatctctgt gtattgtttt attcgcattt     240
tgattctctt attaccagtt atgtagaaag atcggcaaac aaaatatcaa cttttatctt     300
```

```
gaacgctgac ccacggtttc aaataactat cagaactcta tagctatagg ggaagtttac    360
tgcttgctta aagcggctaa aaagtgtttg gcaaattaaa aaagctgtga caagtaggaa    420
ctcctgtaaa gggccgattc gacttcgaaa gagcctaaaa acagtgacta ttggtgacgg    480
aaaattgcta aaggagtact agggctgtag taataaataa tggaacagtg gtacaacaat    540
aaaagaatga cgctgtatgt cgtagcctgc acgagtagct cagtggtaga gcagcagatt    600
gcaaatctgt tggtcaccgg ttcgatccgg tctcgggctt cctttttgc tttttcgata     660 tttgcgggta ggaagcaagg tctagttttc gtcgtttcgg atggtttacg aaagtatcag    720
ccatgagtgt ttccctctgg ctacctaata tatttattga tcggtctctc atgtgaatgt    780
ttctttccaa gttcggcttt cagctcgtaa atgtgcaaga aatatttgac tccagcgacc    840
tttcagagtc aaattaattt tcgctaacaa tttgtgtttt tctggagaaa cctaaagatt    900
taactgataa gtcgaatcaa catctttaaa tcctttagtt aagatctctg cagcggccag    960
tattaaccaa tagcatattc acaggcatca catcggaaca ttcagaatgg actcgcaaac   1020
tgtcgggatt ttaggtggtg gccaacttgg tcgtatgatc gttgaagctg cacacagatt   1080
gaatatcaaa actgtgattc tcgaaaatgg agaccaggct ccagcaaagc aaatcaacgc   1140
tttagatgac catattgacg gctcattcaa tgatccaaaa gcaattgccg aattggctgc   1200
caagtgtgat gttttaaccg ttgagattga acatgttgac actgatgcgt tggttgaagt   1260
tcaaaaggca actggcatca aaatcttccc atcaccagaa actatttcat tgatcaaaga   1320
taaatacttg caaaaagagc atttgattaa gaatggcatt gctgttgccg aatcttgtag   1380
tgttgaaagt agcgcagcat ctttagaaga agttggtgcc aaatacggct tcccatacat   1440
gctaaaatct agaacaatgg cctatgacgg aagaggtaat tttgttgtca agacaagtc    1500 atatatacct gaagctttga agttttaga tgacaggccg ttatacgccg agaaatgggc   1560
tccattttca aaggagttag ctgttatggt tgtgagatca atcgatggcc aagtttattc   1620
ctacccaact gttgaaacca tccaccaaaa caacatctgt cacactgtct ttgctccagc   1680
tagagttaac gatactgtcc aaaagaaggc ccaaattttg gctgacaacg ctgtcaaatc   1740
tttcccaggt gctggtatct ttggtgttga aatgttttta ttacaaaatg gtgacttatt   1800
agtcaacgaa attgccccaa gacctcacaa ttctggtcac tataccatcg acgcttgtgt   1860
cacctcgcaa tttgaagctc atgttagggc cattactggt ctaccatgc cgaagaactt    1920 cacttgtttg tcgactccat ctacccaagc tattatgttg aacgttttag gtggcgatga   1980
gcaaaacggt gagttcaaga tgtgtaaaag agcactagaa actcctcatg cttctgttta   2040
cttatacggt aagactacaa gaccaggcag aaaaatgggt cacattaata tagttttctca  2100 atcaatgact gactgtgagc gtagattaca ttacatagaa ggtacgacta acagcatccc   2160
tctcgaagaa cagtacacta cagattccat tccgggcact tcaagcaagc cattagtcgg   2220
tgtcatcatg ggttccgatt cggacctacc agtcatgtct ctaggttgta atatattgaa   2280
gcaatttaac gttccatttg aagtcactat cgtttccgct catagaaccc cacaaagaat   2340
ggccaagtat gccattgatg ctccaaagag agggttgaag tgcatcattg ctggtgctgg   2400
tggtgccgct catttaccgg gaatggttgc ggcgatgacg ccgctgcctg ttattggtgt   2460
ccctgttaaa ggctctactt tggatggtgt tgattcacta cactccatcg ttcaaatgcc   2520
aagaggtatt cctgttgcta ctgtggctat taacaatgct actaacgctg ccttgctagc   2580
tatcacaatc ttaggtgccg gcgatccaaa tacttgtctg caatggaagt ttatatgaac   2640
```

-continued

| aatatggaaa atgaagtttt gggcaaggct gaaaaattgg aaaatggtgg atatgaagaa | 2700 |
| tacttgagta catacaagaa gtagaacctt ttatatttga tatagtactt actcaaagtc | 2760 |
| ttaattgttc taactgttaa tttctgcttt gcatttctga aagtttaag acaagaaatc | 2820 |
| ttgaaatttc tagttgctcg taagaggaaa cttgcattca ataacatta acaataaatg | 2880 |
| acaataatat attatttcaa cactgctata tggtagtttt ataggtttgg ttaggatttg | 2940 |
| agatattgct agcgcttatc attatcctta attgttcatc gacgcaaatc gacgcatttc | 3000 |
| cacaaaaatt ttccgaacct gttttcact tctccagatc ttggtttagt atagcttttg | 3060 |
| acacctaata cctgcag | 3077 |

<210> SEQ ID NO 2
<211> LENGTH: 3386
<212> TYPE: DNA
<213> ORGANISM: Pichia methanolica

<400> SEQUENCE: 2

| gaattcctgc agcccggggg atcgggtagt ggaatgcacg ttatacccca ctccaaataa | 60 |
| aagtgtagta gccggactga aaggttttag gagtctgttt gtttgttcat gtgcatcatt | 120 |
| ccctaatctg ttaacagtct cggagtatac aaaaaagtaa gtcaaatatc aaggtggccg | 180 |
| ggggcagcat cgagactcga gatggtacat acttaaaagc tgccatattg aggaacttca | 240 |
| aagtttatc tgttttaga attaaaagac gattgttgta acaaaacgtt gtgcctacat | 300 |
| aaactcaaat taatggaaat agcctgtttt gaaaataca ccttcttaag tactgacaaa | 360 |
| gttttgttaa atgactatcg aacaagccat gaaatagcac atttctgcca gtcacttta | 420 |
| acactttcct gcttgctggt tgactctcct catacaaaca cccaaaaggg aaactttcag | 480 |
| tgtggggaca cttgacatct cacatgcacc ccagattaat ttccccagac gatgcggaga | 540 |
| caagacaaaa caacccttg tcctgctctt ttctttctca caccgcgtgg gtgtgtgcgc | 600 |
| aggcaggcag gcaggcagcg ggctgcctgc catctctaat cgctgctcct cccccctggc | 660 |
| ttcaaataac agcctgctgc tatctgtgac cagattggga caccccctc cctccgaat | 720 |
| gatccatcac ctttgtcgt actccgacaa tgatccttcc ctgtcatctt ctggcaatca | 780 |
| gctccttcaa taattaaatc aaataagcat aaatagtaaa atcgcataca aacgtcatga | 840 |
| aaagtttat ctctatggcc aacggatagt ctatctgctt aattccatcc actttgggaa | 900 |
| ccgctctctc tttaccccag attctcaaag ctaaatctg cccttgtct attgtccttt | 960 |
| ctccgtgtac aagcggagct tttgcctccc atcctcttgc tttgtttcgg ttatttttt | 1020 |
| ttcttttgaa actcttggtc aaatcaaatc aaacaaaacc aaaccttcta ttccatcaga | 1080 |
| tcaaccttgt tcaacattct ataaatcgat ataaatataa ccttatccct cccttgtttt | 1140 |
| ttaccaatta atcaatcttc aaatttcaaa tattttctac ttgctttatt actcagtatt | 1200 |
| aacatttgtt taaaccaact ataacttta actggcttta gaagttttat ttaacatcag | 1260 |
| tttcaattta catctttatt tattaacgaa atctttacga attaactcaa tcaaaacttt | 1320 |
| tacgaaaaaa aaatcttact attaatttct caaaatggct attccagatg aatttgatat | 1380 |
| tattgttgtc ggtggtggtt ccaccggttg tgctcttgct ggtagattag gtaacttgga | 1440 |
| cgaaaacgtc acagttgctt taatcgaagg tggtgaaaac aacatcaaca acccatgggt | 1500 |
| ttacttacca ggtgtttatc caagaaacat gagattagac tcaaagactg ctactttta | 1560 |
| ctcttcaaga ccatcaccac acttgaacgg tagaagagct attgttccat gtgctaacat | 1620 |
| cttgggtggt ggttcttcca tcaacttctt gatgtacacc agagcctctg cctccgatta | 1680 |

```
cgatgattgg gaatctgaag gttggactac cgatgaatta ttaccactaa tgaagaagat    1740
tgaaacttat caaagaccat gtaacaacag agaattgcac ggtttcgatg gtccaattaa    1800
ggtttcattt ggtaactata cttatccaaa cggtcaagat ttcattagag ctgccgaatc    1860
tcaaggtatt ccatttgttg atgatgctga agatttgaaa tgttcccacg gtgctgagca    1920
ctggttgaag tggatcaaca gagacttagg tagaagatcc gattctgctc atgcttacat    1980
tcacccaacc atgagaaaca agcaaaactt gttcttgatt acttccacca agtgtgaaaa    2040
gattatcatt gaaaacggtg ttgctactgg tgttaagact gttccaatga agccaactgg    2100
ttctccaaag acccaagttg ctagaacttt caaggctaga agcaaaatta ttgtttcttg    2160
tggtactatc tcatcaccat tagttttgca agatctggat atcggttccg ctcacaagtt    2220
gagacaagtt ggtattaaac caattgttga cttaccaggt gttggtatga acttccaaga    2280
tcactactgt ttcttcactc cataccatgt caagccagat actccatcat cgatgactt    2340 tgttagaggt gataaagctg ttcaaaaatc tgctttcgac caatggtatg ctaacaagga    2400
tggtccatta accactaatg gtattgaggc aggtgttaag attagaccaa ctgaagaaga    2460
attagccact gctgatgacg aattcagagc tgcttatgat gactactttg gtaacaagcc    2520
agataagcca ttaatgcact actctctaat ttctggtttc tttggtgacc acaccaagat    2580
tccaaacggt aagtacatgt gcatgttcca cttcttggaa tatccattct ccagaggttt    2640
cgttcacgtt gtttctccaa acccatacga tgctcctgac tttgatccag gtttcatgaa    2700
cgatccaaga gatatgtggc aatggttttg gtcttacaag aagtccagag aaactgccag    2760
aagaatggac tgttttgccg gtgaagttac ttctcaccac ccacactacc catacgactc    2820
accagccaga gctgctgaca tggacttgga aactactaaa gcttatgctg gtccagacca    2880
ctttactgct aacttgtacc acggttcatg gactgttcca attgaaaagc caactccaaa    2940
gaacgctgct cacgttactt ctaaccaagt tgaaaaacat cgtgacatcg aatacaccaa    3000
ggaggatgat gctgctatcg aagattacat cagagaacac actgaaaacca catggcattg    3060 tcttggtact tgttcaatgg ctccaagaga aggttctaag gttgtcccaa ctggtggtgt    3120
tgttgactcc agattaaacg tttacggtgt tgaaaagttg aaggttgctg atttatcaat    3180
ttgcccagat aatgttggtt gtaacactta ctctactgct ttgttaatcg gtgaaaaggc    3240
ttctacctta gttgctgaag acttgggcta ctctggtgat gctttgaaga tgactgttcc    3300
aaacttcaaa ttgggtactt atgaagaagc tggtctagct agattctagg gctgcctgtt    3360
tggatatttt tataattttt gagagt                                        3386
```

<210> SEQ ID NO 3
<211> LENGTH: 329
<212> TYPE: DNA
<213> ORGANISM: Pichia methanolica

<400> SEQUENCE: 3

```
gaccatgatt acgccaagcg cgcaattaac cctcactaaa gggaacaaaa gctgggtacc    60
gggccccccc tcgaggtcga cggtatcgat aagcttatt ataacattaa tatactattt     120
tataacagga ttgaaaatta tatttatcta tctaaaacta aaattcaaaa tggctattcc    180
tgaagaattc gatatcattg ttgtcggtgg tggttctgcc ggctgtccta ctgctggtag    240
attggctaac ttagacccaa atttaactgt tgctttaatc gaagctggtg aaaacaacat    300
taacaaccca tgggtctact taccaggcg                                     329
```

-continued

```
<210> SEQ ID NO 4
<211> LENGTH: 368
<212> TYPE: DNA
<213> ORGANISM: Pichia methanolica
<220> FEATURE:
<221> NAME/KEY: CDS
<222> LOCATION: (1)...(366)
<221> NAME/KEY: misc_feature
<222> LOCATION: (1)...(368)
<223> OTHER INFORMATION: n = A,T,C or G

<400> SEQUENCE: 4 ggg tcc gna cnc atg gtg ttt cta aga att gcc cac att gtt gcc gtc        48
Gly Ser Xaa Xaa Met Val Phe Leu Arg Ile Ala His Ile Val Ala Val
1               5                   10                  15 aaa gtt tta aga tct aac ggt tca ggt tct atg ccc gat gtt gtc aag        96
Lys Val Leu Arg Ser Asn Gly Ser Gly Ser Met Pro Asp Val Val Lys
            20                  25                  30 ggt gtt gaa tat gct ccc aat gct cac ctt gcg gaa gcc aag gct aac       144
Gly Val Glu Tyr Ala Pro Asn Ala His Leu Ala Glu Ala Lys Ala Asn
        35                  40                  45 aag agt ggt ttt aaa ggt tct acc gcg aac atg tca tta ggt ggt ggt       192
Lys Ser Gly Phe Lys Gly Ser Thr Ala Asn Met Ser Leu Gly Gly Gly
    50                  55                  60 aaa tct cca gct tta gat atg tct gtt aac gct cct gtt aaa gca ggt       240
Lys Ser Pro Ala Leu Asp Met Ser Val Asn Ala Pro Val Lys Ala Gly
65                  70                  75                  80 tta cac ttt gcc gtt acc gct ggt aac gat aac act gat gca tgt aac       288
Leu His Phe Ala Val Thr Ala Gly Asn Asp Asn Thr Asp Ala Cys Asn
                85                  90                  95 tat tct cca gcc act act gaa aat act gtc act gtt gtt gct tcc act       336
Tyr Ser Pro Ala Thr Thr Glu Asn Thr Val Thr Val Val Ala Ser Thr
            100                 105                 110 tta tct gat tcg aga gct gac atg tct aac tc                           368
Leu Ser Asp Ser Arg Ala Asp Met Ser Asn
        115                 120

<210> SEQ ID NO 5
<211> LENGTH: 420
<212> TYPE: DNA
<213> ORGANISM: Pichia methanolica
<220> FEATURE:
<221> NAME/KEY: CDS
<222> LOCATION: (1)...(420)

<400> SEQUENCE: 5 gaa ggt aac gtt tct cag gat act tta gct tta ggt gat tta gtt att        48
Glu Gly Asn Val Ser Gln Asp Thr Leu Ala Leu Gly Asp Leu Val Ile
1               5                   10                  15 cca aaa caa gac ttt gcc gaa gct act tct gag cca ggt tta gca ttc        96
Pro Lys Gln Asp Phe Ala Glu Ala Thr Ser Glu Pro Gly Leu Ala Phe
            20                  25                  30 gca ttt ggt aaa ttt gat ggt att tta ggt tta gct tac gat agc att       144
Ala Phe Gly Lys Phe Asp Gly Ile Leu Gly Leu Ala Tyr Asp Ser Ile
        35                  40                  45 tcg gtc aac aag att gtt cct cct att tat aat gct tta aac ttg ggt       192
Ser Val Asn Lys Ile Val Pro Pro Ile Tyr Asn Ala Leu Asn Leu Gly
    50                  55                  60 tta tta gat gaa cct caa ttt gcc ttc tac cta ggt gat act aac acc       240
Leu Leu Asp Glu Pro Gln Phe Ala Phe Tyr Leu Gly Asp Thr Asn Thr
65                  70                  75                  80 aat gaa gaa gat ggt ggt ctt gcc act ttt ggt ggt gtt gat gag tcc       288
Asn Glu Glu Asp Gly Gly Leu Ala Thr Phe Gly Gly Val Asp Glu Ser
```

```
                    85                  90                  95
aag tat act ggt aaa gtt aca tgg tta cca gtc aga aga aag gct tac     336
Lys Tyr Thr Gly Lys Val Thr Trp Leu Pro Val Arg Arg Lys Ala Tyr
            100                 105                 110 tgg gaa gtt tca tta gac ggt att tca tta ggt gat gaa tac gcg cca     384
Trp Glu Val Ser Leu Asp Gly Ile Ser Leu Gly Asp Glu Tyr Ala Pro
        115                 120                 125 tta gaa ggc cat gga gct gcc att gat aca ggt acc                     420
Leu Glu Gly His Gly Ala Ala Ile Asp Thr Gly Thr
    130                 135                 140
```

<210> SEQ ID NO 6
<211> LENGTH: 140
<212> TYPE: PRT
<213> ORGANISM: Pichia methanolica

<400> SEQUENCE: 6

```
Glu Gly Asn Val Ser Gln Asp Thr Leu Ala Leu Gly Asp Leu Val Ile
 1               5                  10                  15

Pro Lys Gln Asp Phe Ala Glu Ala Thr Ser Glu Pro Gly Leu Ala Phe
            20                  25                  30

Ala Phe Gly Lys Phe Asp Gly Ile Leu Gly Leu Ala Tyr Asp Ser Ile
        35                  40                  45

Ser Val Asn Lys Ile Val Pro Pro Ile Tyr Asn Ala Leu Asn Leu Gly
    50                  55                  60

Leu Leu Asp Glu Pro Gln Phe Ala Phe Tyr Leu Gly Asp Thr Asn Thr
65                  70                  75                  80

Asn Glu Glu Asp Gly Gly Leu Ala Thr Phe Gly Gly Val Asp Glu Ser
                85                  90                  95

Lys Tyr Thr Gly Lys Val Thr Trp Leu Pro Val Arg Arg Lys Ala Tyr
            100                 105                 110

Trp Glu Val Ser Leu Asp Gly Ile Ser Leu Gly Asp Glu Tyr Ala Pro
        115                 120                 125

Leu Glu Gly His Gly Ala Ala Ile Asp Thr Gly Thr
    130                 135                 140
```

<210> SEQ ID NO 7
<211> LENGTH: 146
<212> TYPE: PRT
<213> ORGANISM: Homo sapiens

<400> SEQUENCE: 7

```
Val Pro Ile Gln Lys Val Gln Asp Asp Thr Lys Thr Leu Ile Lys Thr
 1               5                  10                  15

Ile Val Thr Arg Ile Asn Asp Ile Ser His Thr Gln Ser Val Ser Ser
            20                  25                  30

Lys Gln Lys Val Thr Gly Leu Asp Phe Ile Pro Gly Leu His Pro Ile
        35                  40                  45

Leu Thr Leu Ser Lys Met Asp Gln Thr Leu Ala Val Tyr Gln Gln Ile
    50                  55                  60

Leu Thr Ser Met Pro Ser Arg Asn Val Ile Gln Ile Ser Asn Asp Leu
65                  70                  75                  80

Glu Asn Leu Arg Asp Leu Leu His Val Leu Ala Phe Ser Lys Ser Cys
                85                  90                  95

His Leu Pro Glu Ala Ser Gly Leu Glu Thr Leu Asp Ser Leu Gly Gly
            100                 105                 110

Val Leu Glu Ala Ser Gly Tyr Ser Thr Glu Val Val Ala Leu Ser Arg
```

```
        115                 120                 125
Leu Gln Gly Ser Leu Gln Asp Met Leu Trp Gln Leu Asp Leu Ser Pro
    130                 135                 140
Gly Cys
145

<210> SEQ ID NO 8
<211> LENGTH: 4409
<212> TYPE: DNA
<213> ORGANISM: Pichia methanolica
<220> FEATURE:
<221> NAME/KEY: CDS
<222> LOCATION: (1733)...(2734)

<400> SEQUENCE: 8
cccgggggat cttattttct gcaagaactt aaccgaggga catgtcaaac caagcatact      60
gtaaaagaaa tagccgatgg tttatatata tatacttg cgttagtaga aacagtttat      120
gcatgcatgg atgcaagaac tcagatatca ggttatcaag aaacatggag aaattcctaa    180
acagaaacgg aattaatccg aaattctcgg tctcccaaag aaaatagatg cacaagctaa    240
tacagcttgc taactagctt caactttcaa aaaaaattct aagctattga atattcatca    300
agataatagt ctatataaag atgtaaagtc attattattg ggatatataa acgtcctata    360
tattgctgaa atgttaggtg tatgtactga aaacaatcag tttgagtttta ccagagagag    420
acgatggatc tacagatcaa tagagagaga ataagatgag aataagatga ttaatagtga    480
gaggtagtag ccactggcgg gaggatgaaa atatcccgga taaacttaga aagaaattaa    540
ttacacgtat aggtaacatt tgttattgtc gaatctcaga tcagttgatg cctggaacag    600
atcgacttat agatattatc agatcataat catgaggcga ggtgcgacta gtaccaggtg    660
atgatatatt gtttccggtt atttcaaata gttgacgtcg ttgtgtgatt gggaaggcgt    720
cggagtaaca gaaacagtaa cggtacaagc atcattatga gttgagggta tgtagggaag    780
cagttgtttg taagcatgtt tacaaatgca atgcatgtta cgattggact acaattaaat    840
ccgaatgtac ctatataacg tgttgtacgt gttgtgccgt aagtagcccg atactagatg    900
cttactacgt cactgatctg ttcggatctc agtccattca tgtgtcaaaa tagttagtag    960
ctaaggggga tacaggaag atgtttggta cgattatcgg agggatgtgt cttctgaggg   1020
gggaggagag agggcgtgta aggagtttgt ttgtttgttt gtttgttgag agaaggggggg   1080
gagaagaggg ggtggtgggc tgatggcaat tgatatagag ggagagtgtg cgttaactgt   1140
ttagtgtggt ggcggtacgg ggtacactgt agaggggggac attataatgg ttatgtgtat   1200
atgctgtata tatgaataca agtagggagt gactacacat tgcaattgat aatatgtgta   1260
tgtgtgcgca tcagtatata cactcggagg ttctgaaagc catcattgta ttggacgttt   1320
gaatggtatt agatgacttg ttgtactaga ggacggagaa tgggtgagtg aagcaatag    1380
ataataatgg aaagtttgct cggtggtgga cattggcccg gagtagtgat accgtcacct   1440
taaaattgca gttaggggat gatgctccgg ggcacgacct gccaactaat ttaatagtcg   1500
tctaacgctg gaacaggtgt tgttccacaa gtagatgagt tgttggttg gctggtcaaa    1560
tgctgccttg atccatcgtt ttatatataa agactcactc tcctcctcct tgttcaattg   1620
tttcacactc aactgcttct cccttatctt tttttttttcc ctgtttttat ccccattgaa   1680
ctagatcaca tcttttcata ttacacactt ttatttatta taattacaca aa atg gct   1738
                                                         Met Ala
                                                           1
```

-continued

| | | |
|---|---|---|
| att aac gtt ggt att aac ggt ttc ggt aga atc ggt aga tta gtc ttg<br>Ile Asn Val Gly Ile Asn Gly Phe Gly Arg Ile Gly Arg Leu Val Leu<br>5                         10                 15 | | 1786 |
| aga gtt gct tta tca aga aag gac atc aac att gtt gct gtc aat gat<br>Arg Val Ala Leu Ser Arg Lys Asp Ile Asn Ile Val Ala Val Asn Asp<br>20               25                30 | | 1834 |
| cct ttc att gct gct gaa tac gct gct tac atg ttc aag tac gat tcc<br>Pro Phe Ile Ala Ala Glu Tyr Ala Ala Tyr Met Phe Lys Tyr Asp Ser<br>35               40              45            50 | | 1882 |
| act cac ggt aag tac gcc ggc gaa gtt tcc agt gac ggt aaa tac tta<br>Thr His Gly Lys Tyr Ala Gly Glu Val Ser Ser Asp Gly Lys Tyr Leu<br>              55                60               65 | | 1930 |
| atc att gat ggt aag aag att gaa gtt ttc caa gaa aga gac cca gtt<br>Ile Ile Asp Gly Lys Lys Ile Glu Val Phe Gln Glu Arg Asp Pro Val<br>       70                   75                80 | | 1978 |
| aac atc cca tgg ggt aaa gaa ggt gtc caa tac gtt att gac tcc act<br>Asn Ile Pro Trp Gly Lys Glu Gly Val Gln Tyr Val Ile Asp Ser Thr<br>           85                   90               95 | | 2026 |
| ggt gtt ttc act acc ttg gct ggt gct caa aag cac att gat gcc ggt<br>Gly Val Phe Thr Thr Leu Ala Gly Ala Gln Lys His Ile Asp Ala Gly<br>100                    105              110 | | 2074 |
| gct gaa aag gtt atc atc act gct cca tct gct gat gct cca atg ttc<br>Ala Glu Lys Val Ile Ile Thr Ala Pro Ser Ala Asp Ala Pro Met Phe<br>115                  120              125            130 | | 2122 |
| gtt gtt ggt gtt aac gaa aag gaa tac act tct gac ttg aag att gtt<br>Val Val Gly Val Asn Glu Lys Glu Tyr Thr Ser Asp Leu Lys Ile Val<br>                 135              140              145 | | 2170 |
| tct aac gct tca tgt acc acc aac tgt ttg gct cca tta gct aag gtt<br>Ser Asn Ala Ser Cys Thr Thr Asn Cys Leu Ala Pro Leu Ala Lys Val<br>           150                  155              160 | | 2218 |
| gtt aac gac aac ttt ggt att gaa tca ggt tta atg acc act gtc cac<br>Val Asn Asp Asn Phe Gly Ile Glu Ser Gly Leu Met Thr Thr Val His<br>165                    170              175 | | 2266 |
| tcc att acc gct acc caa aag acc gtc gat ggt cca tca cac aag gac<br>Ser Ile Thr Ala Thr Gln Lys Thr Val Asp Gly Pro Ser His Lys Asp<br>180                  185              190 | | 2314 |
| tgg aga ggt ggt aga act gct tcc ggt aac att atc cca tca tct act<br>Trp Arg Gly Gly Arg Thr Ala Ser Gly Asn Ile Ile Pro Ser Ser Thr<br>195                  200              205            210 | | 2362 |
| ggt gct gct aag gct gtt ggt aag gtt tta cct gtc tta gct ggt aag<br>Gly Ala Ala Lys Ala Val Gly Lys Val Leu Pro Val Leu Ala Gly Lys<br>                 215              220              225 | | 2410 |
| tta acc ggt atg tct tta aga gtt cct act acc gat gtt tcc gtt gtt<br>Leu Thr Gly Met Ser Leu Arg Val Pro Thr Thr Asp Val Ser Val Val<br>           230                  235              240 | | 2458 |
| gat tta acc gtt aac tta aag act cca acc act tac gaa gct att tgt<br>Asp Leu Thr Val Asn Leu Lys Thr Pro Thr Thr Tyr Glu Ala Ile Cys<br>245                    250              255 | | 2506 |
| gct gct atg aag aag gct tct gaa ggt gaa tta aag ggt gtt tta ggt<br>Ala Ala Met Lys Lys Ala Ser Glu Gly Glu Leu Lys Gly Val Leu Gly<br>260                  265              270 | | 2554 |
| tac act gaa gac gct gtt gtt tcc act gat ttc tta acc gat aac aga<br>Tyr Thr Glu Asp Ala Val Val Ser Thr Asp Phe Leu Thr Asp Asn Arg<br>275                  280              285            290 | | 2602 |
| tca tct atc ttt gat gct aag gct ggt atc tta tta acc cca act ttc<br>Ser Ser Ile Phe Asp Ala Lys Ala Gly Ile Leu Leu Thr Pro Thr Phe<br>                 295              300              305 | | 2650 |
| gtt aag tta atc tct tgg tac gat aac gaa tac ggt tac tcc acc aga<br>Val Lys Leu Ile Ser Trp Tyr Asp Asn Glu Tyr Gly Tyr Ser Thr Arg<br>           310                  315              320 | | 2698 |

-continued

```
gtt gtt gat tta cta caa cac gtt gct tcc gct taa atcttacaat           2744
Val Val Asp Leu Leu Gln His Val Ala Ser Ala
        325                 330 ctagattgtg aagtataagt aagcaaaaat tatatatata tttgtctttc atagtataag    2804
tatagttttc atgagaaata cagataaaca acaaaaaata agttctttt gaaaagtta     2864 gattttattc ttgaacttag taaaagcctt ccttttacag ctgcttactt acaaccttga    2924
aggctattgc ataagctcaa ttgaaaacga gtataatata ctgatttcaa ggtttaatta    2984
tctgtaattt tcaagtactt ccatacgtgg aaacctccca caattaacag caacacgaaa    3044
catccatcat ccaacaaccg agatgcggat taggcccgga gagataatat ttttcggtgt    3104
ggcggtggtt tcaactccga acgcagcgca gccaaaagca aacagatgat ttagtgaact    3164
cttcttatga tagattttg gctgattgag ttgatctgac ctgtgtggtt cgatcgaatt     3224
ctattgtgtt tgatgccctg gtagtggtgt gcttcatctt attgtgaagt gtgaatccta    3284
gcgattatgg catttggacg ccaactacta gctctgacgg tagtggcttc tacgaatgta    3344
acttacaatt ctgctcaatt cgaacatctt ttcagtaaga gaagttatat atgtatgtgt    3404
gtatgtgtat gtaaatatac ataaccgctt gtgggggtga ttttggttt gtactgatgt     3464 gaaactcagt gctatcggat gatgctgtca ccaacaacag ctgcttaacc ttcttttac    3524 tattctgata cagaattagg aaagtttccg gatttgtgat gtgcggcttt ggttgccatt    3584
agtctccttt ttttggaggg aggagtgaag tggtgcgtta tgtgccctga tccaatggtt    3644
ttgaaagagg gagctaggga tagttaatgg gtagacctat gaacattgtg tattaatata    3704
ttgaaatata caaacataac ggctgaaaac agcaagaaat caaaaaggca caatttcaat    3764
ggtatataac ttcaataatg atagtaatag taatggtagt agttattaca ggaggaataa    3824
tatcaagaaa ggaaaactaa aagtacacca acgtattcag aaatacaaaa acagcgaaca    3884
aaatcgtcga ttagtaattc atatcatgat tgccatccaa acagctttct ttcattgaac    3944
tcacgagggc ttgcactatt ttccctgctt gatgagtaat ccatcatttc aaactcggtt    4004
gaacctgtag caccagaagc gccatttgac gtaattggcc ttgtaatttg ctgttgttgt    4064
tgggatatgt ttgattcatt ttggaaacgt tcatgatgcc ctcttttttt gttgtttgtt    4124
gttggtatcg gtgaattcga tctagatgca gaactgccac tattgttgtt attgccgttg    4184
ttcgcattat tgttatcgtc aaagtcaaag tcaagtaatg gaagaccaag ggaagcatca    4244
acaccaaaat cattcaacat cagtaaatcc gagtacgact taatggtatc tgcctgaatc    4304
gttgcttgct gctgattatg ctgttgttgg ttttgttgtt gctgtttcgc agtcagttgg    4364
aaatgatcca ctagttctag agcggccgcc accgcggtgg agctc               4409
```

<210> SEQ ID NO 9
<211> LENGTH: 333
<212> TYPE: PRT
<213> ORGANISM: Pichia methanolica

<400> SEQUENCE: 9

```
Met Ala Ile Asn Val Gly Ile Asn Gly Phe Gly Arg Ile Gly Arg Leu
 1               5                  10                  15

Val Leu Arg Val Ala Leu Ser Arg Lys Asp Ile Asn Ile Val Ala Val
            20                  25                  30

Asn Asp Pro Phe Ile Ala Ala Glu Tyr Ala Ala Tyr Met Phe Lys Tyr
        35                  40                  45

Asp Ser Thr His Gly Lys Tyr Ala Gly Glu Val Ser Ser Asp Gly Lys
```

```
              50                  55                  60
Tyr Leu Ile Ile Asp Gly Lys Lys Ile Glu Val Phe Gln Glu Arg Asp
 65                  70                  75                  80

Pro Val Asn Ile Pro Trp Gly Lys Glu Gly Val Gln Tyr Val Ile Asp
                 85                  90                  95

Ser Thr Gly Val Phe Thr Thr Leu Ala Gly Ala Gln Lys His Ile Asp
            100                 105                 110

Ala Gly Ala Glu Lys Val Ile Ile Thr Ala Pro Ser Ala Asp Ala Pro
        115                 120                 125

Met Phe Val Val Gly Val Asn Glu Lys Glu Tyr Thr Ser Asp Leu Lys
130                 135                 140

Ile Val Ser Asn Ala Ser Cys Thr Thr Asn Cys Leu Ala Pro Leu Ala
145                 150                 155                 160

Lys Val Val Asn Asp Asn Phe Gly Ile Glu Ser Gly Leu Met Thr Thr
                165                 170                 175

Val His Ser Ile Thr Ala Thr Gln Lys Thr Val Asp Gly Pro Ser His
            180                 185                 190

Lys Asp Trp Arg Gly Gly Arg Thr Ala Ser Gly Asn Ile Ile Pro Ser
        195                 200                 205

Ser Thr Gly Ala Ala Lys Ala Val Gly Lys Val Leu Pro Val Leu Ala
210                 215                 220

Gly Lys Leu Thr Gly Met Ser Leu Arg Val Pro Thr Thr Asp Val Ser
225                 230                 235                 240

Val Val Asp Leu Thr Val Asn Leu Lys Thr Pro Thr Thr Tyr Glu Ala
                245                 250                 255

Ile Cys Ala Ala Met Lys Lys Ala Ser Glu Gly Glu Leu Lys Gly Val
            260                 265                 270

Leu Gly Tyr Thr Glu Asp Ala Val Val Ser Thr Asp Phe Leu Thr Asp
        275                 280                 285

Asn Arg Ser Ser Ile Phe Asp Ala Lys Ala Gly Ile Leu Leu Thr Pro
290                 295                 300

Thr Phe Val Lys Leu Ile Ser Trp Tyr Asp Asn Glu Tyr Gly Tyr Ser
305                 310                 315                 320

Thr Arg Val Val Asp Leu Leu Gln His Val Ala Ser Ala
                325                 330

<210> SEQ ID NO 10
<211> LENGTH: 3333
<212> TYPE: DNA
<213> ORGANISM: Pichia methanolica
<220> FEATURE:
<221> NAME/KEY: CDS
<222> LOCATION: (1093)...(2094)

<400> SEQUENCE: 10
cataaaccat aatagtataa tttgttagac aagttcaaag aatttccaat aaaagtgtaa      60
ttttcacatg catttcaacc cggagaataa aatttttaaga atccgattg gatagtgtag    120 aattattgtt catattgtgt tataataatt gcaattaccc aacaaaactt gcattggtta    180
gtcatcgtat ttcatgctat tagctgaaag tagggtaatc gagcggtttg aatggctctg    240
taaatctaaa ctctttatct gaaatgtata ttagatccga catgatgcat ttggaggttc    300
tgagaggtac cgcattgaat ttctgtgtgg aattagatga gttgttgtac cagaagaggg    360
aaaatgggca agtggtggca atagtaaatt atggaagta tggtggatat tggcccggcg    420
tagtgacatc ctcaccttaa aattgcctta ggggataatg tgccgggcac gtccagctaa    480
```

```
ctaatttagt agtcgtctaa aactggggaa catttgttgt tcctttgata gttatacgaa    540
actgattgaa taaaaagttt atattcttct tgatgatcct tctgtctaat tgatagaata    600
ggaatttaga tagaaatatg gaaatacaca aaatatatgt aataaaatca aaagggggaac   660 aattcaaagg attcagcaat caaaagggat gagtgattct gggtaataaa tgagcaataa    720
attagtaata aattagtaac aagttagtaa taaattagta ataaattagc aacaaatgaa    780
caatagtaaa agctaaaaga taaaacaaaa ggtaggagat aagcagtaaa gtccgaaagt    840
aatcaggtga ctagagtaag gatgagaatg aaggacagat tccttacagc tacataagta    900
gatgagctgt tgacggtcag atggtgcctt ggtccatggt ttcatatata aagaccctct    960
tcgtctcctt ttgttcgctt gtttcacact caactgtttc tgattttacc ttttttcccc   1020
tgcttgattc ccccattgaa tcagatcaag tgttttcata gaacccactt ttatttattt   1080
```
tagttgcaca aa atg gcc att aac gtt ggt att aac ggt ttc ggg aga atc    1131
          Met Ala Ile Asn Val Gly Ile Asn Gly Phe Gly Arg Ile
            1               5                  10 ggc aga tta gtc ttg aga gtt gcc tta tcg aga aaa gac atc aac gtc     1179
Gly Arg Leu Val Leu Arg Val Ala Leu Ser Arg Lys Asp Ile Asn Val
 15                  20                  25 gtt gct gtc aac gat cct ttc att gct cct gat tac gct gct tac atg    1227
Val Ala Val Asn Asp Pro Phe Ile Ala Pro Asp Tyr Ala Ala Tyr Met
 30                  35                  40                  45 ttc aag tac gat tcc act cac ggt aag tac act ggt gaa gtt tca agt    1275
Phe Lys Tyr Asp Ser Thr His Gly Lys Tyr Thr Gly Glu Val Ser Ser
                 50                  55                  60 gat ggt aaa tac tta atc att gat ggt aag aag att gaa gtt ttc caa    1323
Asp Gly Lys Tyr Leu Ile Ile Asp Gly Lys Lys Ile Glu Val Phe Gln
             65                  70                  75 gaa aga gat cca gcc aac atc cca tgg ggg aaa gaa ggt gtt cag tac    1371
Glu Arg Asp Pro Ala Asn Ile Pro Trp Gly Lys Glu Gly Val Gln Tyr
         80                  85                  90 gtt att gaa tcc act ggc gtt ttc acc acc ttg gct ggt gct caa aag    1419
Val Ile Glu Ser Thr Gly Val Phe Thr Thr Leu Ala Gly Ala Gln Lys
     95                  100                 105 cac att gat gct ggt gcg gaa aag gtt atc atc act gct cca tct tct    1467
His Ile Asp Ala Gly Ala Glu Lys Val Ile Ile Thr Ala Pro Ser Ser
110                 115                 120                 125 gat gct cca atg ttt gtt gtt ggt gtt aac gaa aag gaa tac act cct    1515
Asp Ala Pro Met Phe Val Val Gly Val Asn Glu Lys Glu Tyr Thr Pro
                 130                 135                 140 gac ttg aag att gtt tca aat gcc tca tgt acc acc aac tgc gtg gct    1563
Asp Leu Lys Ile Val Ser Asn Ala Ser Cys Thr Thr Asn Cys Val Ala
             145                 150                 155 aca tta gct aaa gtt gtt gac gat aac ttt gga att gaa tct ggg tta    1611
Thr Leu Ala Lys Val Val Asp Asp Asn Phe Gly Ile Glu Ser Gly Leu
         160                 165                 170 atg acc gct gtt cac gcc att act gct tcc caa aag atc gtc gat ggt    1659
Met Thr Ala Val His Ala Ile Thr Ala Ser Gln Lys Ile Val Asp Gly
     175                 180                 185 ccc tcc cac aag gac tgg aga ggt ggt aga acc gct tcc ggc aac att    1707
Pro Ser His Lys Asp Trp Arg Gly Gly Arg Thr Ala Ser Gly Asn Ile
190                 195                 200                 205 atc cca tca tca act ggt gct gct aag gct gtt ggt aag gtt ttg cca    1755
Ile Pro Ser Ser Thr Gly Ala Ala Lys Ala Val Gly Lys Val Leu Pro
                 210                 215                 220 gct tta gct ggc aag cta acc ggt atg tct ata agg gtt cct act act    1803
Ala Leu Ala Gly Lys Leu Thr Gly Met Ser Ile Arg Val Pro Thr Thr

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     | 225 |     |     |     |     | 230 |     |     |     |     | 235 |     |     |      |
| gat | gtt | tcc | gtt | gct | gat | tta | acc | gtt | aac | tta | aag | act | gct | acc | acc | 1851 |
| Asp | Val | Ser | Val | Ala | Asp | Leu | Thr | Val | Asn | Leu | Lys | Thr | Ala | Thr | Thr |      |
|     |     | 240 |     |     |     |     | 245 |     |     |     |     | 250 |     |     |     |      |
| tac | cag | gaa | att | tgc | gct | gct | ata | aag | aag | gct | tct | gaa | ggt | gaa | tta | 1899 |
| Tyr | Gln | Glu | Ile | Cys | Ala | Ala | Ile | Lys | Lys | Ala | Ser | Glu | Gly | Glu | Leu |      |
|     | 255 |     |     |     |     | 260 |     |     |     |     | 265 |     |     |     |     |      |
| aag | ggt | att | tta | ggt | tac | act | gaa | gat | gcc | gtt | gtt | tca | acc | gac | ttc | 1947 |
| Lys | Gly | Ile | Leu | Gly | Tyr | Thr | Glu | Asp | Ala | Val | Val | Ser | Thr | Asp | Phe |      |
| 270 |     |     |     |     | 275 |     |     |     |     | 280 |     |     |     |     | 285 |      |
| tta | acc | gat | agc | aga | tcg | tct | atc | ttc | gat | gcc | aaa | gct | ggt | atc | tta | 1995 |
| Leu | Thr | Asp | Ser | Arg | Ser | Ser | Ile | Phe | Asp | Ala | Lys | Ala | Gly | Ile | Leu |      |
|     |     |     |     | 290 |     |     |     |     | 295 |     |     |     |     | 300 |     |      |
| tta | acc | cca | acc | ttc | gtt | aag | cta | atc | tct | tgg | tac | gat | aac | gaa | tac | 2043 |
| Leu | Thr | Pro | Thr | Phe | Val | Lys | Leu | Ile | Ser | Trp | Tyr | Asp | Asn | Glu | Tyr |      |
|     |     |     | 305 |     |     |     |     | 310 |     |     |     |     | 315 |     |     |      |
| ggt | tat | tcc | acc | aga | gtt | gtt | gac | tta | cta | caa | cat | gtt | gct | tcc | gcc | 2091 |
| Gly | Tyr | Ser | Thr | Arg | Val | Val | Asp | Leu | Leu | Gln | His | Val | Ala | Ser | Ala |      |
|     | 320 |     |     |     |     | 325 |     |     |     |     | 330 |     |     |     |     |      |

```
taa atcttccaac ctaaattgcg aaatataagc aagcaaaaat tatatgtata       2144
tttgtcttcc attgcataag tctatctttc ctgagaaata acaaaaatat gttcttttcg  2204
agacacttaa gttttatttt tgcccttagt acaaggcatc catttgcagt tgctgcttac  2264
agccctgaag gctattgcat cagcccaatt ggaaacaagt atagcatact gatttgaggg  2324
tttaattatc tgtaatattc aagtacttat atgcgtagaa cctccaaata gcaacacgaa  2384
aatccatcat ccaacaatca aagatgtgga gcaggccaag caagatgata ttttctcggt  2444
ggtggcggtt tcaatttctg gggtgcgtta ttgtgtggct tgtaccttgc agggtaaacc  2504
ttcgccagca gttccagtgg tctcttcgac gaacaacagg ctgaaattcg gctgtttcag  2564
catggcttgt ttttcctcca tgggactagc gtagatttat ccccccagaa agtttctctt  2624
cttgaatatc tctggtaccg accactaact agattataga ttactgcgac atgttaaagc  2684
attgtcgggt tctttaagca tgctcaacca acaggttgcc tgaagagctg cgtactaacc  2744
tggaacaggg ttcacagaaa gagggcaacc cagaaaaaac actatttgtt aacccttata  2804
gtgaagagtg ggggtacaaa atctttgacc cgtactccac tacgcagtt ttgataaaca   2864 cttgcagatt acctaatttg gtatgtacaa tttctaggca tgggataagt atagctttta  2924
atccggaagg ttcggataaa tactgtgctg tgtgccaggc aaatgcgtcc cactggagaa  2984
aaaggtaaag ccgactaacc gaagacccac ctacaataaa tttaccgagc caccgaaaaa  3044
ctcacgttac tcaatatatg agtaatgtac tactataact atgtgtggaa tagaattgta  3104
ttgtatagta gctcagcttt cttcctggta tacggtcgac tttagcctaa acacttgttg  3164
gttcagtgaa tacagcctga ttagactaaa aggtagaagg actataaagg tgtacatacg  3224
gaaatcctac tccccactta aatagacaaa acccctctaa gtgttgtttc gacgtaaagc  3284
tttgtttact gacaagcctt ggcaccgatc ccccgggctg caggaattc              3333
```

```
<210> SEQ ID NO 11
<211> LENGTH: 333
<212> TYPE: PRT
<213> ORGANISM: Pichia methanolica

<400> SEQUENCE: 11
```

| Met | Ala | Ile | Asn | Val | Gly | Ile | Asn | Gly | Phe | Gly | Arg | Ile | Gly | Arg | Leu |
| --- | --- | --- | --- | --- | --- | --- | --- | --- | --- | --- | --- | --- | --- | --- | --- |
| 1   |     |     |     | 5   |     |     |     |     | 10  |     |     |     |     | 15  |     |

-continued

```
Val Leu Arg Val Ala Leu Ser Arg Lys Asp Ile Asn Val Val Ala Val
            20                  25                  30

Asn Asp Pro Phe Ile Ala Pro Asp Tyr Ala Ala Tyr Met Phe Lys Tyr
            35                  40                  45

Asp Ser Thr His Gly Lys Tyr Thr Gly Glu Val Ser Ser Asp Gly Lys
    50                  55                  60

Tyr Leu Ile Ile Asp Gly Lys Lys Ile Glu Val Phe Gln Glu Arg Asp
65                  70                  75                  80

Pro Ala Asn Ile Pro Trp Gly Lys Glu Gly Val Gln Tyr Val Ile Glu
                85                  90                  95

Ser Thr Gly Val Phe Thr Thr Leu Ala Gly Ala Gln Lys His Ile Asp
            100                 105                 110

Ala Gly Ala Glu Lys Val Ile Ile Thr Ala Pro Ser Ser Asp Ala Pro
            115                 120                 125

Met Phe Val Val Gly Val Asn Glu Lys Glu Tyr Thr Pro Asp Leu Lys
            130                 135                 140

Ile Val Ser Asn Ala Ser Cys Thr Thr Asn Cys Val Ala Thr Leu Ala
145                 150                 155                 160

Lys Val Val Asp Asp Asn Phe Gly Ile Glu Ser Gly Leu Met Thr Ala
                165                 170                 175

Val His Ala Ile Thr Ala Ser Gln Lys Ile Val Asp Gly Pro Ser His
            180                 185                 190

Lys Asp Trp Arg Gly Gly Arg Thr Ala Ser Gly Asn Ile Ile Pro Ser
            195                 200                 205

Ser Thr Gly Ala Ala Lys Ala Val Gly Lys Val Leu Pro Ala Leu Ala
            210                 215                 220

Gly Lys Leu Thr Gly Met Ser Ile Arg Val Pro Thr Thr Asp Val Ser
225                 230                 235                 240

Val Ala Asp Leu Thr Val Asn Leu Lys Thr Ala Thr Thr Tyr Gln Glu
            245                 250                 255

Ile Cys Ala Ala Ile Lys Lys Ala Ser Glu Gly Glu Leu Lys Gly Ile
            260                 265                 270

Leu Gly Tyr Thr Glu Asp Ala Val Val Ser Thr Asp Phe Leu Thr Asp
            275                 280                 285

Ser Arg Ser Ser Ile Phe Asp Ala Lys Ala Gly Ile Leu Leu Thr Pro
            290                 295                 300

Thr Phe Val Lys Leu Ile Ser Trp Tyr Asp Asn Glu Tyr Gly Tyr Ser
305                 310                 315                 320

Thr Arg Val Val Asp Leu Leu Gln His Val Ala Ser Ala
                325                 330
```